(12) United States Patent
Muci et al.

(10) Patent No.: US 8,293,761 B2
(45) Date of Patent: *Oct. 23, 2012

(54) CERTAIN CHEMICAL ENTITIES, COMPOSITIONS AND METHODS

(75) Inventors: Alex Muci, San Francisco, CA (US); Jeffrey T. Finer, Foster City, CA (US); Pu-Ping Lu, Foster City, CA (US); Alan James Russell, San Francisco, CA (US); Bradley P. Morgan, Moraga, CA (US); David J. Morgans, Jr., Los Altos, CA (US)

(73) Assignee: Cytokinetics, Inc., South San Francisco, CA (US)

( * ) Notice: Subject to any disclaimer, the term of this patent is extended or adjusted under 35 U.S.C. 154(b) by 83 days.

This patent is subject to a terminal disclaimer.

(21) Appl. No.: 12/765,820

(22) Filed: Apr. 22, 2010

(65) Prior Publication Data

US 2010/0210645 A1    Aug. 19, 2010

Related U.S. Application Data

(63) Continuation of application No. 12/573,730, filed on Oct. 5, 2009, now Pat. No. 7,956,056, which is a continuation of application No. 11/888,902, filed on Aug. 1, 2007, now Pat. No. 7,598,248.

(60) Provisional application No. 60/835,272, filed on Aug. 2, 2006, provisional application No. 60/921,054, filed on Mar. 30, 2007.

(51) Int. Cl.
  *A61K 31/44* (2006.01)
(52) U.S. Cl. ......................................... 514/283
(58) Field of Classification Search .................. 514/283
  See application file for complete search history.

(56) References Cited

U.S. PATENT DOCUMENTS

| | | | |
|---|---|---|---|
| 3,507,866 A | 4/1970 | Jones et al. | |
| 4,195,088 A | 3/1980 | Barzaghi et al. | |
| 4,943,573 A | 7/1990 | Meanwell | |
| 5,354,759 A | 10/1994 | Oku et al. | |
| 6,162,804 A | 12/2000 | Bilodeau et al. | |
| 6,232,320 B1 | 5/2001 | Stewart et al. | |
| 6,579,882 B2 | 6/2003 | Stewart et al. | |
| 6,638,933 B2 | 10/2003 | Gerlach et al. | |
| 6,657,064 B2 | 12/2003 | Gerlach et al. | |
| 7,279,580 B2 | 10/2007 | Goodacre et al. | |
| 7,348,339 B2 | 3/2008 | Bailey et al. | |
| 7,598,248 B2 | 10/2009 | Muci et al. | |
| 7,851,484 B2 | 12/2010 | Morgan et al. | |
| 7,956,056 B2 | 6/2011 | Muci et al. | |
| 2003/0220365 A1 | 11/2003 | Stewart et al. | |
| 2004/0023972 A1 | 2/2004 | Sundermann et al. | |
| 2004/0166137 A1 | 8/2004 | Lackey | |
| 2005/0197328 A1 | 9/2005 | Bailey et al. | |
| 2005/0250794 A1 | 11/2005 | Napper et al. | |
| 2006/0019952 A1 | 1/2006 | Distefano et al. | |
| 2006/0148805 A1 | 7/2006 | Chen et al. | |
| 2007/0197507 A1 | 8/2007 | Morgan et al. | |
| 2007/0275984 A1 | 11/2007 | Imogai et al. | |
| 2008/0096903 A1 | 4/2008 | Chen et al. | |
| 2008/0146561 A1 | 6/2008 | Muci et al. | |
| 2008/0242695 A1 | 10/2008 | Morgan et al. | |
| 2009/0023724 A1 | 1/2009 | Mortensen et al. | |
| 2009/0029345 A1 | 1/2009 | Russell et al. | |
| 2009/0082370 A1 | 3/2009 | Thompson et al. | |
| 2009/0247538 A1 | 10/2009 | Berdini et al. | |
| 2009/0247571 A1 | 10/2009 | Muci et al. | |
| 2010/0022564 A1 | 1/2010 | Davies et al. | |

FOREIGN PATENT DOCUMENTS

| | | |
|---|---|---|
| DE | 22 41 575 | 3/1973 |
| GB | 2 174 987 A | 11/1986 |
| GB | 2 190 676 A | 11/1987 |
| GB | 2 400 101 A | 10/2004 |
| IL | 40080 A | 2/1975 |
| JP | 06-041134 A | 2/1994 |
| WO | WO 99/62908 A2 | 12/1999 |
| WO | WO-2004/092166 A2 | 10/2004 |
| WO | WO 2005/002520 A2 | 1/2005 |
| WO | WO-2005/013894 A2 | 2/2005 |
| WO | WO 2005/060711 A2 | 7/2005 |
| WO | WO 2005/072412 A2 | 8/2005 |
| WO | WO 2005/108374 A1 | 11/2005 |
| WO | WO 2006/030031 A1 | 3/2006 |
| WO | WO 2006/036883 A2 | 4/2006 |
| WO | WO 2006/046024 A1 | 5/2006 |
| WO | WO-2006/088836 A2 | 8/2006 |
| WO | WO 2007/125310 A2 | 11/2007 |
| WO | WO 2007/125321 A2 | 11/2007 |
| WO | WO 2008/016648 A2 | 2/2008 |
| WO | WO 2008/049105 A2 | 4/2008 |
| WO | WO/2008/051493 A3 | 5/2008 |
| WO | WO-2008-075007 A1 | 6/2008 |

(Continued)

OTHER PUBLICATIONS

Advisory Action for U.S. Appl. No. 12/573,730 mailed Dec. 21, 2010.
Bianchi et al., Compounds with Antiulcer and antisecretory activity. III. N-substituted imidazolones condensed with nitrogen-containing heteroaromatic rigns, European Journal of Medical Chemistry (1983), 18(6), 501-6.
Bjoerk et al., Synthesis of Novel 2-Aminoimidazo [4,5-b] Pyridines, Including the Thieno Analogue of the Cooked-Food Mutagen IFP, Journal of Heterocyclic Chemistry, 43(1): 101-109 (2006).
Bonnet et al: "Synthesis and antibronchospastic activity of 8-alkoxy- and 8-(alkylamino)imidazo(1,2-a)pyrazines" Journal of Medicinal Chemistry, vol. 35, No. 18, Jan. 1, 1992, pp. 3353-3358.

(Continued)

*Primary Examiner* — Brandon Fetterolf
*Assistant Examiner* — Christopher R Stone
(74) *Attorney, Agent, or Firm* — Foley & Lardner LLP

(57) ABSTRACT

Provided are certain chemical entities, and methods of use to modulate skeletal myosin, skeletal actin, skeletal tropomyosin, skeletal troponin C, skeletal troponin I, skeletal troponin T, and skeletal muscle, including fragments and isoforms thereof, as well as the skeletal sarcomere, and methods of use in the treatment of obesity, sarcopenia, wasting syndrome, frailty, cachexia, muscle spasm, post-surgical and post-traumatic muscle weakness, neuromuscular disease, and other indications.

20 Claims, No Drawings

FOREIGN PATENT DOCUMENTS

| WO | WO-2008/089459 A1 | 7/2008 |
| WO | WO-2010/068483 A2 | 6/2010 |

OTHER PUBLICATIONS

Iupac Ed—Alan D McNaught and Andrew Wilkinson: "alkyl groups" [Online]Jan. 1, 1997, Compendium of Chemical Terminology: , Iupac Recommendations; [Iupac Chemical Data Series], Blackwell Science, Oxford [U.A.], XP002585005 ISBN: 978-0-86542-684-9 Retrieved from the Internet: URL:http://www.iupac.org/goldbook/A00228.pdf.

Iupac Ed. Alan D. McNaught and Andrew Wilkinson "cycloalkyl groups" [Online] Jan. 1, 1997, Compendium of Chemical Terminology: Iupac Recommendations; [Iupac Chemical Data Series], Blackwell Science, Oxford [U.A.] , XP002585006 ISBN: 978-0-86542-684-9 Retrieved from the Internet: URL: http://www.iupac.org/goldbook/C01498.pdf.

Li et al., Skeletal Muscle Respiratory Uncoupling Prevents Diet-Induced Obesity and Insulin Resistance in Mice, Nature Medicine, vol. 6(10), (2000), pp. 115-1120.

Lindstroem et al., Synthesis of the mutagenic 2-Amino-1,6-Dimethyl-Imidazo[4,5-b]Pyridine (1,6-DMIP) and Five of Its Isomers, Heterocycles, Elsevier Science Publishers B.V. (1994), 38(3), 529-40.

Meanwell et al., 1,3 Dihydro-2H-Imidazo[4,5-b]quinolin-2-ones—Inhibitors of Blood Platelet cAMP Phosphodiesterase and Induced Aggregation Journal of Medicinal Chemistry (1991), 34(9), 2906-16.

Meanwell et al., Inhibitors of Blood Platelet cAMP Phosphodiesterase. 3. 1,3-Dihydro-2H-imidazo[4,5-b]quinolin-2-one derivates with enhanced aqueous solubility, Journal of Medicinal Chemistry, 35(14): 2688-96 (1992).

Meanwell et al., Inhibitors of Blood Platelet cAMP Phosphodiesterase.2. Structure-activity Relationships Associated with 1,3-dihydro-2H-imidazo[4,5-b]quinolin-2-ones substituted with functionalized side chains, Journal of Medicinal Chemistry, 35(14):2672-87 (1992).

Morimoto et al., "Ca2+ binding to skeletal muscle troponic C in skeletal and cardiac myofibrils", J. biochem., 105,435-439 (1989).

Niel et al., Sexual Differentiation of the Spinal Nucleus of the Bulbocavernosus is not Medicated Solely by Adrogen Receptors in Muscle Fibers, Endocrinology, (2009), 150(7), pp. 3207-3213.

Notice of Allowance for U.S. Appl. No. 12/058,127 mailed Aug. 9, 2010.

Notice of Allowance for U.S. Appl. No. 12/058,127 mailed Nov. 10, 2010.

Notice of Allowance for U.S. Appl. No. 12/359,186 mailed Apr. 11, 2011.

Notice of Allowance for U.S. Appl. No. 12/364,394 mailed Mar. 22, 2011.

Notice of Allowance for U.S. Appl. No. 12/573,730 mailed Feb. 1, 2011.

Office Action for U.S. Appl. No. 11/888,902 mailed Mar. 5, 2009.
Office Action for U.S. Appl. No. 12/058,127 mailed Feb. 25, 2010.
Office Action for U.S. Appl. No. 12/165,498 mailed Oct. 25, 2010.
Office Action for U.S. Appl. No. 12/359,186 mailed Dec. 2, 2010.
Office Action for U.S. Appl. No. 12/573,730 mailed Jul. 8, 2010.
Office Action for U.S. Appl. No. 12/573,730 mailed Oct. 13, 2010.
Restriction Requirement for U.S. Appl. No. 12/058,127 mailed Nov. 23, 2009.
Restriction Requirement for U.S. Appl. No. 12/359,186 mailed Sep. 14, 2010.
Restriction Requirement for U.S. Appl. No. 12/364,394 mailed Jan. 5, 2011.
Restriction Requirement for U.S. Appl. No. 12/573,730 mailed Apr. 29, 2010.
Restriction Requirement for U.S. Appl. No. 12/780,644 mailed Jan. 6, 2012.

Shirai et al,, "New syntheses and spectral properties of pteridine-related heterocycles from 2,5-diamino-36-dicyanopyridine" Journal of Heterocyclic Chemistry, vol. 37, 2000, pp. 1151-1156.

Supplementary European Search Report for EPO Application No. 08742350.5 mailed Apr. 8, 2010.

Vitse et al: "New Imidazo(1 ,2-a)pyrazine Derivatives with Bronchodilatory and Cyclic Nucleotide Phosphodiesterase Inhibitory Activities" Bioorganic & Medicinal Chemistry, vol. 7, Jan. 1, 1999, pp. 1059-1065.

Yutilov et al., Halogenation of 2-Unsubstituted and 2-Methylimidazo[4,5-b]Pyridine Derivatives, Russian Journal of Organic Chemistry (2005), 41(3), 450-454.

Yutilov et al., Halogenation of Imidazo[4,5-b]Pyridin-2-one , Russian Journal of Organic Chemistry (2005), 41(4), 575-579.

Zhu et al., "Synthesis of inidazo[4,5-b]quinoxaline Ribonucleosides as Linear Dimensional Analogs of Antiviral Polyhalogenated Benzimidazole Ribonucleosides" Journal of the Chinese Chemical Society, Chinese Electronic Periodical Services, China, vol. 45, No. 4, pp. 465-474.

International Search Report and Written Opinion mailed Aug. 8, 2008 for PCT/US2007/017191.

International Search Report and Written Opinion mailed Oct. 1, 2008 for PCT/US2007/017235.

International Search Report and Written Opinion mailed Jul. 1, 2008 for PCT/US2008/004075.

International Search Report and Written Opinion mailed Apr. 8, 2009 for PCT/US2009/000686.

Office Action mailed Oct. 21, 2008 for U.S. Appl. No. 11/888,902, filed Aug. 1, 2007.

Office Action mailed Mar. 5, 2009 for U.S. Appl. No. 11/888,902, filed Aug. 1, 2007.

Notice of Allowance for U.S. Appl. No. 11/888,902, mailed Jun. 1, 2009.

Barlin, Aust. J. Chem., 35:2299-2306 (1982).

Dörwald, Side Reactions in Organic Synthesis: A Guide to Successful Synthesis Design, Weinheim: Wiley-VCH Verlag GmbH & Co., KGaA, Preface (2005).

Jordan, Nature Reviews, Drug Discovery 2:205-213 (Mar. 2003).
Lima et al., Current Medicinal Chemistry 12(1):23-49 (2005).
Almirante. Derivatives of Imidazole. I. Synthesis and reactions of Imidazo[1,2-a]pyridines with analgesic, anti-inflammatory, antipyretic and anticonvulsant activity. J. Med. Chem 1965, 8, 305-312.

Restriction Requirement for U.S. Appl. No. 12/519,518 mailed Feb. 13, 2012.

CERTAIN CHEMICAL ENTITIES, COMPOSITIONS AND METHODS

This application is a continuation of U.S. patent application No. 12/573,730, filed Oct. 5, 2009, now U.S. Pat. No. 7,956,056, which is a continuation of U.S. patent application Ser. No. 11/888,902, filed Aug. 1, 2007, now U.S. Pat. No. 7,598,248, which claims the benefit of U.S. Provisional Patent Application No. 60/835,272, filed Aug. 2, 2006, and U.S. Provisional Patent Application No. 60/921,054, filed Mar. 30, 2007, each of which is incorporated herein by reference for all purposes.

Provided are certain chemical entities that modulate skeletal myosin, skeletal actin, skeletal tropomyosin, skeletal troponin C, skeletal troponin I, skeletal troponin T, and skeletal muscle, including fragments and isoforms thereof, as well as the skeletal sarcomere. Also provided are certain chemical entities, pharmaceutical compositions and methods of treatment of one or more of obesity, sarcopenia, wasting syndrome, frailty, cachexia, muscle spasm, post-surgical and post-traumatic muscle weakness, and neuromuscular disease.

The cytoskeleton of skeletal and cardiac muscle cells is unique compared to that of all other cells. It consists of a nearly crystalline array of closely packed cytoskeletal proteins called the sarcomere. The sarcomere is elegantly organized as an interdigitating array of thin and thick filaments. The thick filaments are composed of myosin, the motor protein responsible for transducing the chemical energy of ATP hydrolysis into force and directed movement. The thin filaments are composed of actin monomers arranged in a helical array. There are four regulatory proteins bound to the actin filaments, which allows the contraction to be modulated by calcium ions. An influx of intracellular calcium initiates muscle contraction; thick and thin filaments slide past each other driven by repetitive interactions of the myosin motor domains with the thin actin filaments.

Myosin is the most extensively studied of all the motor proteins. Of the thirteen distinct classes of myosin in human cells, the myosin-II class is responsible for contraction of skeletal, cardiac, and smooth muscle. This class of myosin is significantly different in amino acid composition and in overall structure from myosin in the other twelve distinct classes. Myosin-II consists of two globular head domains linked together by a long alpha-helical coiled-coiled tail that assembles with other myosin-IIs to form the core of the sarcomere's thick filament. The globular heads have a catalytic domain where the actin binding and ATP functions of myosin take place. Once bound to an actin filament, the release of phosphate (cf. ATP to ADP) leads to a change in structural conformation of the catalytic domain that in turn alters the orientation of the light-chain binding lever arm domain that extends from the globular head; this movement is termed the powerstroke. This change in orientation of the myosin head in relationship to actin causes the thick filament of which it is a part to move with respect to the thin actin filament to which it is bound. Un-binding of the globular head from the actin filament (also $Ca^{2+}$ modulated) coupled with return of the catalytic domain and light chain to their starting conformation/orientation completes the contraction and relaxation cycle, responsible for intracellular movement and muscle contraction.

Tropomyosin and troponin mediate the calcium effect on the interaction on actin and myosin. The skeletal troponin complex regulates the action of several actin units at once, and is comprised of three polypepetide chains: skeletal troponin C, which binds calcium ions; troponin I, which binds to actin; and troponin T, which binds to tropomyosin.

Abnormal contraction of skeletal muscle is thought to be a pathogenetic cause of several disorders, including obesity, sarcopenia, wasting syndrome, frailty, cachexia, muscle spasm, post-surgical and post-traumatic muscle weakness, and neuromuscular disease, which pose serious health problems as adult diseases. The contraction and relaxation of skeletal muscle are mainly controlled by increases and decreases of intracellular calcium.

Accordingly, there is a need for the development of new compounds modulate skeletal muscle. There remains a need for agents that exploit new mechanisms of action and which may have better outcomes in terms of relief of symptoms, safety, and patient mortality, both short-term and long-term and an improved therapeutic index.

Provided is at least one chemical entity chosen from compounds of Formula I and compounds of Formula II:

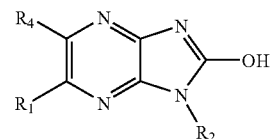

Formula I

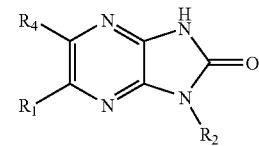

Formula II and pharmaceutically acceptable salts thereof, wherein $R_1$ and $R_4$ are independently selected from hydrogen, halo, hydroxy, optionally substituted acyl, optionally substituted alkyl, optionally substituted amino, optionally substituted alkenyl, optionally substituted alkynyl, optionally substituted cycloalkyl, optionally substituted heteroaryl, optionally substituted alkoxy, optionally substituted aminocarbonyl, sulfonyl, sulfanyl, sulfinyl, carboxy, optionally substituted alkoxycarbonyl, and cyano; and in the alternative, $R_4$ and $R_1$, taken together with any intervening atoms, form a fused ring system selected from optionally substituted fused aryl, optionally substituted fused heteroaryl, optionally substituted fused cycloalkyl, and optionally substituted fused heterocycloalkyl; and $R_2$ is is selected from optionally substituted alkyl, optionally substituted cycloalkyl, optionally substituted aryl, optionally substituted heteroaryl, and optionally substituted heterocycloalkyl;

provided that $R_1$ is not hex-1-enyl; and further provided that the compound of Formula I or the compound of Formula II is not (S)-6-bromo-1-(1-phenylethyl)-1H-imidazo[4,5-b]pyrazin-2(3H)-one;

1,5,6-trimethyl-1H-imidazo[4,5-b]pyrazin-2(3H)-one;

1-methyl-1H-imidazo[4,5-b]pyrazin-2(3H)-one;

6-bromo-1-(3-nitrobenzyl)-1H-imidazo[4,5-b]pyrazin-2(3H)-one;

5-(hydroxymethyl)-1,6-dimethyl-1H-imidazo[4,5-b]pyrazin-2(3H)-one; or 1-(piperidin-4-yl)-1H-imidazo[4,5-b]pyrazin-2(3H)-one.

Also provided is a pharmaceutically acceptable composition comprising a pharmaceutically acceptable carrier and at least one chemical entity described herein.

Also provided are methods for treating a patient having a disease chosen from obesity, sarcopenia, wasting syndrome, frailty, cachexia, muscle spasm, post-surgical and post-traumatic muscle weakness, and neuromuscular disease, comprising administering to the patient a therapeutically effective amount of at least one chemical entity described herein.

Also provided is a method of treating one or more of obesity, sarcopenia, wasting syndrome, frailty, cachexia, muscle spasm, post-surgical and post-traumatic muscle weakness, neuromuscular disease, and other indications in a mammal which method comprises administering to a mammal in need thereof a therapeutically effective amount of at least one chemical entity described herein or a pharmaceutical composition comprising a pharmaceutically acceptable excipient, carrier or adjuvant and at least one chemical entity described herein.

Also provided is a method for treating a patient having a disease responsive to modulation of one or more of skeletal myosin, skeletal actin, skeletal tropomyosin, skeletal troponin C, skeletal troponin I, skeletal troponin T, and skeletal muscle, including fragments and isoforms thereof, as well as the skeletal sarcomere in a mammal which method comprises administering to a mammal in need thereof a therapeutically effective amount of at least one chemical entity described herein or a pharmaceutical composition comprising a pharmaceutically acceptable excipient, carrier or adjuvant and at least one chemical entity described herein.

Also provided is a method for treating a patient having a disease responsive to potentiation of one or more of skeletal myosin, skeletal actin, skeletal tropomyosin, skeletal troponin C, skeletal troponin I, skeletal troponin T, and skeletal muscle, including fragments and isoforms thereof, as well as the skeletal sarcomere in a mammal which method comprises administering to a mammal in need thereof a therapeutically effective amount of at least one chemical entity described herein or a pharmaceutical composition comprising a pharmaceutically acceptable excipient, carrier or adjuvant and at least one chemical entity described herein.

Also provided is a method for treating a patient having a disease responsive to inhibition of one or more of skeletal myosin, skeletal actin, skeletal tropomyosin, skeletal troponin C, skeletal troponin I, skeletal troponin T, and skeletal muscle, including fragments and isoforms thereof, as well as the skeletal sarcomere in a mammal which method comprises administering to a mammal in need thereof a therapeutically effective amount of at least one chemical entity described herein or a pharmaceutical composition comprising a pharmaceutically acceptable excipient, carrier or adjuvant and at least one chemical entity described herein.

Other aspects and embodiments will be apparent to those skilled in the art from the following detailed description.

As used in the present specification, the following words and phrases are generally intended to have the meanings as set forth below, except to the extent that the context in which they are used indicates otherwise.

The following abbreviations and terms have the indicated meanings throughout:
Ac=acetyl
APCI=atmospheric pressure chemical ionization
atm=atomosphere
Boc=tert-butoxycarbonyl
c-=cyclo
CBZ=carbobenzyloxy=benzyloxycarbonyl
CDI=carbonyldiimidazole
DCM=dichloromethane=methylene chloride=$CH_2Cl_2$
DIEA=DIPEA=N,N-diisopropylethylamine
DMF=N,N-dimethylformamide
DMSO=dimethyl sulfoxide
(DPPF)$PdCl_2$=[1,1'-bis(diphenylphosphino)ferrocene] dichloropalladium(II)
Et=ethyl
EtOAc=ethyl acetate
EtOH=ethanol
g=gram
GC=gas chromatograghy
h or hr=hour
HPLC=high pressure liquid chromatography
i-=iso
kg or Kg=kilogram
l or L=liter
LCMS=liquid chromatography-mass spectrometry
m/z=mass-to-charge ratio
Me=methyl
NMP=1-methyl-2-pyrrolidinone
NMR=nuclear magnetic resonance
MPLC=medium pressure liquid chromatography
min=minute
mg=milligram
mL or ml=milliliter
MW=microwave
n-=normal
Ph=phenyl
$(Ph_3P)_4Pd$ =tetrakis(triphenylphosphine)palladium(0)
$(Ph_3P)_2PdCl_2$=dichlorobis(triphenylphosphine)palladium (II)
rt or RT=room temperature
s-=sec-=secondary
t-=tert-=tertiary
TES=triethylsilyl or triethylsilane
TMS=trimethylsilyl or trimethylsilane
TFA=trifluoroacetic acid
THF=tetrahydrofuran
TLC=thin layer chromatography
UV=ultraviolet
vol=volume equivalent in mL/g or L/Kg for the limiting reagent unless otherwise indicated By "optional" or "optionally" is meant that the subsequently described event or circumstance may or may not occur, and that the description includes instances where the event or circumstance occurs and instances in which it does not. For example, "optionally substituted alkyl" encompasses both "alkyl" and "substituted alkyl" as defined below. It will be understood by those skilled in the art, with respect to any group containing one or more substituents, that such groups are not intended to introduce any substitution or substitution patterns that are sterically impractical, synthetically non-feasible, and/or inherently unstable.

"Alkyl" encompasses straight chain and branched chain having the indicated number of carbon atoms, usually from 1 to 20 carbon atoms, for example 1 to 8 carbon atoms, such as 1 to 6 carbon atoms. For example $C_1$-$C_6$ alkyl encompasses both straight and branched chain alkyl of from 1 to 6 carbon atoms. When an alkyl residue having a specific number of carbons is named, all branched and straight chain versions having that number of carbons are intended to be encompassed; thus, for example, "butyl" is meant to include n-butyl, sec-butyl, isobutyl and t-butyl; "propyl" includes n-propyl and isopropyl. "Lower alkyl" refers to alkyl groups having one to seven carbons. In certain embodiments, "lower alkyl" refers to alkyl groups having one to six carbons. Examples of alkyl groups include methyl, ethyl, propyl, isopropyl, n-butyl, sec-butyl, tert-butyl, pentyl, 2-pentyl, isopentyl, neopentyl, hexyl, 2-hexyl, 3-hexyl, 3-methylpentyl, and the like. Alkylene is a subset of alkyl, referring to the same residues as alkyl, but having two points of attachment. Alkylene groups will usually have from 2 to 20 carbon atoms, for example 2 to 8 carbon atoms, such as from 2 to 6 carbon atoms. For example, $C_0$ alkylene indicates a covalent bond and $C_1$ alkylene is a methylene group.

"Alkenyl" refers to an unsaturated branched or straight-chain alkyl group having at least one carbon-carbon double bond derived by the removal of one molecule of hydrogen from adjacent carbon atoms of the parent alkyl. The group may be in either the cis or trans configuration about the double bond(s). Typical alkenyl groups include, but are not limited to, ethenyl; propenyls such as prop-1-en-1-yl, prop-1-en-2-yl, prop-2-en-1-yl (allyl), prop-2-en-2-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-dien-2-yl; and the like. In certain embodiments, an alkenyl group has from 2 to 20 carbon atoms and in other embodiments, from 2 to 6 carbon atoms. "Lower alkenyl" refers to alkenyl groups having two to six carbons.

"Alkynyl" refers to an unsaturated branched or straight-chain alkyl group having at least one carbon-carbon triple bond derived by the removal of two molecules of hydrogen from adjacent carbon atoms of the parent alkyl. Typical alkynyl groups include, but are not limited to, ethynyl; propynyls such as prop-1-yn-1-yl, prop-2-yn-1-yl; butynyls such as but-1-yn-1-yl, but-1-yn-3-yl, but-3-yn-1-yl; and the like. In certain embodiments, an alkynyl group has from 2 to 20 carbon atoms and in other embodiments, from 3 to 6 carbon atoms. "Lower alkynyl" refers to alkynyl groups having two to six carbons.

"Cycloalkyl" indicates a non-aromatic carbocyclic ring, usually having from 3 to 7 ring carbon atoms. The ring may be saturated or have one or more carbon-carbon double bonds. Examples of cycloalkyl groups include cyclopropyl, cyclobutyl, cyclopentyl, cyclopentenyl, cyclohexyl, and cyclohexenyl, as well as bridged and caged ring groups such as norbornane.

The term "alkoxy" refers to the group —O-alkyl, including from 1 to 8 carbon atoms of a straight, branched, cyclic configuration and combinations thereof attached to the parent structure through an oxygen. Examples include methoxy, ethoxy, propoxy, isopropoxy, cyclopropyloxy, cyclohexyloxy and the like. "Lower alkoxy" refers to alkoxy groups containing one to six carbons.

The term "substituted alkoxy" refers to alkoxy wherein the alkyl constituent is substituted (i.e., —O—(substituted alkyl)) wherein "substituted alkyl" refers to alkyl wherein one or more (such as up to 5, for example, up to 3) hydrogen atoms are replaced by a substituent independently chosen from:

—$R^a$, —$OR^b$, optionally substituted amino (including —$NR^cCOR^b$, —$NR^cCO_2R^a$, —$NR^cCONR^bR^c$, —$NR^bC(NR^c)NR^bR^c$, —$NR^bC(NCN)NR^bR^c$, and —$NR^cSO_2R^a$), halo, cyano, nitro, oxo (as a substitutent for cycloalkyl, heterocycloalkyl, and heteroaryl), optionally substituted acyl (such as —$COR^b$), optionally substituted alkoxycarbonyl (such as —$CO_2R^b$), aminocarbonyl (such as —$CONR^bR^c$), —$OCOR^b$, —$OCO_2R^a$, —$OCONR^bR^c$, —$OCONR^bR^c$, —$OP(O)(OR^b)OR^c$, sulfanyl (such as $SR^b$), sulfinyl (such as —$SOR^a$), and sulfonyl (such as —$SO_2R^a$ and —$SO_2NR^bR^c$), where $R^a$ is chosen from optionally substituted $C_1$-$C_6$ alkyl, optionally substituted alkenyl, optionally substituted alkynyl, optionally substituted aryl, and optionally substituted heteroaryl;

$R^b$ is chosen from H, optionally substituted $C_1$-$C_6$ alkyl, optionally substituted cycloalkyl, optionally substituted heterocycloalkyl, optionally substituted aryl, and optionally substituted heteroaryl; and $R^c$ is independently chosen from hydrogen and optionally substituted $C_1$-$C_4$ alkyl; or $R^b$ and $R^c$, and the nitrogen to which they are attached, form an optionally substituted heterocycloalkyl group; and where each optionally substituted group is unsubstituted or independently substituted with one or more, such as one, two, or three, substituents independently selected from $C_1$-$C_4$ alkyl, aryl, heteroaryl, aryl-$C_1$-$C_4$ alkyl-, heteroaryl-$C_1$-$C_4$ alkyl-, $C_1$-$C_4$ haloalkyl, —$OC_1$-$C_4$ alkyl, —$OC_1$-$C_4$ alkylphenyl, —$C_1$-$C_4$ alkyl-OH, —$OC_1$-$C_4$ haloalkyl, halo, —OH, —$NH_2$, —$C_1$-$C_4$ alkyl-$NH_2$, —$N(C_1$-$C_4$ alkyl)($C_1$-$C_4$ alkyl), —$NH(C_1$-$C_4$ alkyl), —$N(C_1$-$C_4$ alkyl)($C_1$-$C_4$ alkylphenyl), —$NH(C_1$-$C_4$ alkylphenyl), cyano, nitro, oxo (as a substitutent for cycloalkyl, heterocycloalkyl, or heteroaryl), —$CO_2H$, —$C(O)OC_1$-$C_4$ alkyl, —$CON(C_1$-$C_4$ alkyl)($C_1$-$C_4$ alkyl), —$CONH(C_1$-$C_4$ alkyl), —$CONH_2$, —$NHC(O)(C_1$-$C_4$ alkyl), —$NHC(O)(phenyl)$, —$N(C_1$-$C_4$ alkyl)$C(O)(C_1$-$C_4$ alkyl), —$N(C_1$-$C_4$ alkyl)$C(O)(phenyl)$, —$C(O)C_1$-$C_4$ alkyl, —$C(O)C_1$-$C_4$ alkylphenyl, —$C(O)C_1$-$C_4$ haloalkyl, —$OC(O)C_1$-$C_4$ alkyl, —$SO_2(C_1$-$C_4$ alkyl), —$SO_2(phenyl)$, —$SO_2(C_1$-$C_4$ haloalkyl), —$SO_2NH_2$, —$SO_2NH(C_1$-$C_4$ alkyl), —$SO_2NH(phenyl)$, —$NHSO_2(C_1$-$C_4$ alkyl), —$NHSO_2(phenyl)$, and —$NHSO_2(C_1$-$C_4$ haloalkyl).

In some embodiments, a substituted alkoxy group is "polyalkoxy" or —O— (optionally substituted alkylene)-(optionally substituted alkoxy), and includes groups such as —$OCH_2CH_2OCH_3$, and residues of glycol ethers such as polyethyleneglycol, and —$O(CH_2CH_2O)_xCH_3$, where x is an integer of 2-20, such as 2-10, and for example, Another substituted alkoxy group is hydroxyalkoxy or —$OCH_2(CH_2)_yOH$, where y is an integer of 1-10, such as 1-4.

The term "alkoxycarbonyl" refers to a group of the formula (alkoxy)(C=O)— attached through the carbonyl carbon wherein the alkoxy group has the indicated number of carbon atoms. Thus a $C_1$-$C_6$ alkoxycarbonyl group is an alkoxy group having from 1 to 6 carbon atoms attached through its oxygen to a carbonyl linker. "Lower alkoxycarbonyl" refers to an alkoxycarbonyl group wherein the alkoxy group is a lower alkoxy group.

The term "substituted alkoxycarbonyl" refers to the group (substituted alkyl)-O—C(O)— wherein the group is attached to the parent structure through the carbonyl functionality and wherein substituted refers to alkyl wherein one or more (such as up to 5, for example, up to 3) hydrogen atoms are replaced by a substituent independently chosen from:

—$R^a$, —$OR^b$, optionally substituted amino (including —$NR^cCOR^b$, —$NR^cCO_2R^a$, —$NR^cCONR^bR^c$, —$NR^bC(NR^c)NR^bR^c$, —$NR^bC(NCN)NR^bR^c$, and —$NR^cSO_2R^a$), halo, cyano nitro, oxo (as a substitutent for cycloalkyl, heterocycloalkyl, and heteroaryl), optionally substituted acyl (such as —$COR^b$), optionally substituted alkoxycarbonyl (such as —$CO_2R^b$), aminocarbonyl (such as —$CONR^bR^c$), —$OCOR^b$, —$OCO_2R^a$, —$OCONR^bR^c$, —$OCONR^bR^c$, —$OP(O)(OR^b)OR^c$, sulfanyl (such as $SR^b$), sulfinyl (such as —$SOR^a$), and sulfonyl (such as —$SO_2R^a$ and —$SO_2NR^bR^c$), where $R^a$ is chosen from optionally substituted $C_1$-$C_6$ alkyl, optionally substituted alkenyl, optionally substituted alkynyl, optionally substituted aryl, and optionally substituted heteroaryl;

$R^b$ is chosen from H, optionally substituted $C_1$-$C_6$ alkyl, optionally substituted cycloalkyl, optionally substituted heterocycloalkyl, optionally substituted aryl, and optionally substituted heteroaryl; and $R^c$ is independently chosen from hydrogen and optionally substituted $C_1$-$C_4$ alkyl; or $R^b$ and $R^c$, and the nitrogen to which they are attached, form an optionally substituted heterocycloalkyl group; and where each optionally substituted group is unsubstituted or independently substituted with one or more, such as one, two, or three, substituents independently selected from $C_1$-$C_4$ alkyl, aryl, heteroaryl, aryl-$C_1$-$C_4$ alkyl-, heteroaryl-$C_1$-$C_4$ alkyl-, $C_1$-$C_4$ haloalkyl, —$OC_1$-$C_4$ alkyl, —$OC_1$-$C_4$ alkylphenyl, —$C_1$-$C_4$ alkyl-OH, —$OC_1$-$C_4$ haloalkyl, halo, —OH, —$NH_2$, —$C_1$-$C_4$ alkyl-$NH_2$, —$N(C_1$-$C_4$ alkyl)($C_1$-$C_4$ alkyl), —$NH(C_1$-$C_4$ alkyl), —$N(C_1$-$C_4$ alkyl)($C_1$-$C_4$ alkylphenyl), —$NH(C_1$-$C_4$ alkylphenyl), cyano, nitro, oxo (as a substituent for cycloalkyl, heterocycloalkyl, or heteroaryl), —$CO_2H$, —C(O)O$C_1$-$C_4$ alkyl, —CON($C_1$-$C_4$ alkyl)($C_1$-$C_4$ alkyl), —CONH($C_1$-$C_4$ alkyl), —$CONH_2$, —NHC(O)($C_1$-$C_4$ alkyl), —NHC(O)(phenyl), —N($C_1$-$C_4$ alkyl)C(O)($C_1$-$C_4$ alkyl), —N($C_1$-$C_4$ alkyl)C(O)(phenyl), —C(O)$C_1$-$C_4$ alkyl, —C(O)$C_1$-$C_4$ alkylphenyl, —C(O)$C_1$-$C_4$ haloalkyl, —OC(O)$C_1$-$C_4$ alkyl, —$SO_2$($C_1$-$C_4$ alkyl), —$SO_2$(phenyl), —$SO_2$($C_1$-$C_4$ haloalkyl), —$SO_2NH_2$, —$SO_2NH$($C_1$-$C_4$ alkyl), —$SO_2NH$(phenyl), —$NHSO_2$($C_1$-$C_4$ alkyl), —$NHSO_2$(phenyl), and —$NHSO_2$($C_1$-$C_4$ haloalkyl).

"Acyl" refers to the groups H—C(O)—, (alkyl)-C(O)—, (aryl)-C(O)—, (heteroaryl)-C(O)—, and (heterocycloalkyl)-C(O)—, wherein the group is attached to the parent structure through the carbonyl functionality, and wherein alkyl, aryl, heteroaryl, and heterocycloalkyl are optionally substituted as described herein. Examples include acetyl, benzoyl, propionyl, isobutyryl, t-butoxycarbonyl, benzyloxycarbonyl and the like. "Lower-acyl" refers to groups containing one to six carbons and "acyloxy" refers to the group O-acyl.

The term "amino" refers to the group —$NH_2$.

The term "substituted amino" refers to the group —$NHR^d$ or —$NR^dR^e$ wherein $R^d$ is chosen from hydroxy, optionally substituted alkoxy, optionally substituted alkyl, optionally substituted cycloalkyl, optionally substituted acyl, optionally substituted carbamimidoyl, aminocarbonyl, optionally substituted aryl, optionally substituted heteroaryl, optionally substituted heterocycloalkyl, optionally substituted alkoxycarbonyl, sulfinyl and sulfonyl, and $R^e$ is chosen from optionally substituted alkyl, optionally substituted cycloalkyl, optionally substituted aryl, optionally substituted heteroaryl, and optionally substituted heterocycloalkyl, and wherein substituted alkyl, cycloalkyl, aryl, heterocycloalkyl, and heteroaryl refer respectively to alkyl, cycloalkyl, aryl, heterocycloalkyl, and heteroaryl wherein one or more (such as up to 5, for example, up to 3) hydrogen atoms are replaced by a substituent independently chosen from:

—$R^a$, —$OR^b$, optionally substituted amino (including —$NR^cCOR^b$, —$NR^cCO_2R^a$, —$NR^cCONR^bR^c$, —$NR^bC(NR^c)NR^bR^c$, —$NR^bC(NCN)NR^bR^c$, and —$NR^cSO_2R^a$), halo, cyano, nitro, oxo (as a substituent for cycloalkyl, heterocycloalkyl, and heteroaryl), optionally substituted acyl (such as —$COR^b$), optionally substituted alkoxycarbonyl (such as —$CO_2R^b$), aminocarbonyl (such as —$CONR^bR^c$), —$OCOR^b$, —$OCO_2R^a$, —$OCONR^bR^c$, —$OCONR^bR^c$, —$OP(O)(OR^b)OR^c$, sulfanyl (such as $SR^b$), sulfinyl (such as —$SOR^a$), and sulfonyl (such as —$SO_2R^a$ and —$SO_2NR^bR^c$), where $R^a$ is chosen from optionally substituted $C_1$-$C_6$ alkyl, optionally substituted alkenyl, optionally substituted alkynyl, optionally substituted aryl, and optionally substituted heteroaryl;

$R^b$ is chosen from H, optionally substituted $C_1$-$C_6$ alkyl, optionally substituted cycloalkyl, optionally substituted heterocycloalkyl, optionally substituted aryl, and optionally substituted heteroaryl; and $R^c$ is independently chosen from hydrogen and optionally substituted $C_1$-$C_4$ alkyl; or $R^b$ and $R^c$, and the nitrogen to which they are attached, form an optionally substituted heterocycloalkyl group; and where each optionally substituted group is unsubstituted or independently substituted with one or more, such as one, two, or three, substituents independently selected from $C_1$-$C_4$ alkyl, aryl, heteroaryl, aryl-$C_1$-$C_4$ alkyl-, heteroaryl-$C_1$-$C_4$ alkyl-, $C_1$-$C_4$ haloalkyl, —$OC_1$-$C_4$ alkyl, —$OC_1$-$C_4$ alkylphenyl, —$C_1$-$C_4$ alkyl-OH, —$OC_1$-$C_4$ haloalkyl, halo, —OH, —$NH_2$, —$C_1$-$C_4$ alkyl-$NH_2$, —$N(C_1$-$C_4$ alkyl)($C_1$-$C_4$ alkyl), —$NH(C_1$-$C_4$ alkyl), —$N(C_1$-$C_4$ alkyl)($C_1$-$C_4$ alkylphenyl), —$NH(C_1$-$C_4$ alkylphenyl), cyano, nitro, oxo (as a substituent for cycloalkyl, heterocycloalkyl, or heteroaryl), —$CO_2H$, —C(O)O$C_1$-$C_4$ alkyl, —CON($C_1$-$C_4$ alkyl)($C_1$-$C_4$ alkyl), —CONH($C_1$-$C_4$ alkyl), —$CONH_2$, —NHC(O)($C_1$-$C_4$ alkyl), —NHC(O)(phenyl), —N($C_1$-$C_4$ alkyl)C(O)($C_1$-$C_4$ alkyl), —N($C_1$-$C_4$ alkyl)C(O)(phenyl), —C(O)$C_1$-$C_4$ alkyl, —C(O)$C_1$-$C_4$ alkylphenyl, —C(O)$C_1$-$C_4$ haloalkyl, —OC(O)$C_1$-$C_4$ alkyl, —$SO_2$($C_1$-$C_4$ alkyl), —$SO_2$(phenyl), —$SO_2$($C_1$-$C_4$ haloalkyl), —$SO_2NH_2$, —$SO_2NH$($C_1$-$C_4$ alkyl), —$SO_2NH$(phenyl), —$NHSO_2$($C_1$-$C_4$ alkyl), —$NHSO_2$(phenyl), and —$NHSO_2$($C_1$-$C_4$ haloalkyl); and wherein optionally substituted acyl, optionally substituted alkoxycarbonyl, sulfinyl and sulfonyl are as defined herein.

The term "substituted amino" also refers to N-oxides of the groups —$NHR^d$, and $NR^dR^d$ each as described above. N-oxides can be prepared by treatment of the corresponding amino group with, for example, hydrogen peroxide or m-chloroperoxybenzoic acid. The person skilled in the art is familiar with reaction conditions for carrying out the N-oxidation.

The term "aminocarbonyl" refers to the group —$CONR^bR^c$, where $R^b$ is chosen from H, optionally substituted $C_1$-$C_6$ alkyl, optionally substituted cycloalkyl, optionally substituted heterocycloalkyl, optionally substituted aryl, and optionally substituted heteroaryl; and $R^c$ is independently chosen from hydrogen and optionally substituted $C_1$-$C_4$ alkyl; or $R^b$ and $R^c$ taken together with the nitrogen to which they are bound, form an optionally substituted 5- to 7-membered nitrogen-containing heterocycloalkyl which optionally includes 1 or 2 additional heteroatoms selected from O, N, and S in the heterocycloalkyl ring;

where each substituted group is independently substituted with one or more substituents independently selected from $C_1$-$C_4$ alkyl, aryl, heteroaryl, aryl-$C_1$-$C_4$ alkyl-, heteroaryl-$C_1$-$C_4$ alkyl-, $C_1$-$C_4$ haloalkyl, -$OC_1$-$C_4$ alkyl, -$OC_1$-$C_4$ alkylphenyl, —$C_1$-$C_4$ alkyl-OH, —$OC_1$-$C_4$ haloalkyl, halo, —OH, —$NH_2$, —$C_1$-$C_4$ alkyl-$NH_2$, —$N(C_1$-$C_4$ alkyl)($C_1$-$C_4$ alkyl), —$NH(C_1$-$C_4$ alkyl), —$N(C_1$-$C_4$ alkyl)($C_1$-$C_4$ alkylphenyl), —$NH(C_1$-$C_4$ alkylphenyl), cyano, nitro, oxo (as a substituent for cycloalkyl, heterocycloalkyl, or heteroaryl), —$CO_2H$, —C(O)O$C_1$-$C_4$ alkyl, —CON($C_1$-$C_4$ alkyl)($C_1$-$C_4$ alkyl), —CONH($C_1$-$C_4$ alkyl), —$CONH_2$, —NHC(O)($C_1$-$C_4$ alkyl), —NHC(O)(phenyl), —N($C_1$-$C_4$ alkyl)C(O)($C_1$-$C_4$ alkyl), —N($C_1$-$C_4$ alkyl)C(O)(phenyl), —C(O)$C_1$-$C_4$ alkyl, —C(O)$C_1$-$C_4$ alkylphenyl, —C(O)$C_1$-$C_4$ haloalkyl, —OC(O)$C_1$-$C_4$ alkyl, —$SO_2$($C_1$-$C_4$ alkyl), —$SO_2$(phenyl), —$SO_2$($C_1$-$C_4$ haloalkyl), —$SO_2NH_2$, —$SO_2NH$($C_1$-$C_4$ alkyl), —$SO_2NH$(phenyl), —$NHSO_2$($C_1$-$C_4$ alkyl), —$NHSO_2$(phenyl), and —$NHSO_2$($C_1$-$C_4$ haloalkyl).

"Aryl" encompasses:

6-membered carbocyclic aromatic rings, for example, benzene;

bicyclic ring systems wherein at least one ring is carbocyclic and aromatic, for example, naphthalene, indane, and tetralin; and tricyclic ring systems wherein at least one ring is carbocyclic and aromatic, for example, fluorene.

For example, aryl includes 6-membered carbocyclic aromatic rings fused to a 5- to 7-membered heterocycloalkyl ring containing 1 or more heteroatoms chosen from N, O, and S. For such fused, bicyclic ring systems wherein only one of the rings is a carbocyclic aromatic ring, the point of attachment may be at the carbocyclic aromatic ring or the heterocycloalkyl ring. Bivalent radicals formed from substituted benzene derivatives and having the free valences at ring atoms are named as substituted phenylene radicals. Bivalent radicals derived from univalent polycyclic hydrocarbon radicals whose names end in "-yl" by removal of one hydrogen atom from the carbon atom with the free valence are named by adding "-idene" to the name of the corresponding univalent radical, e.g., a naphthyl group with two points of attachment is termed naphthylidene. Aryl, however, does not encompass or overlap in any way with heteroaryl, separately defined below. Hence, if one or more carbocyclic aromatic rings is fused with a heterocycloalkyl aromatic ring, the resulting ring system is heteroaryl, not aryl, as defined herein.

"Aralkoxy" refers to the group —O-aralkyl. Similarly, "heteroaralkoxy" refers to the group —O-heteroaralkyl; "aryloxy" refers to —O-aryl; and "heteroaryloxy" refers to the group —O-heteroaryl.

"Aralkyl" refers to a residue in which an aryl moiety is attached to the parent structure via an alkyl residue. Examples include benzyl, phenethyl, phenylvinyl, phenylallyl and the like. "Heteroaralkyl" refers to a residue in which a heteroaryl moiety is attached to the parent structure via an alkyl residue. Examples include furanylmethyl, pyridinylmethyl, pyrimidinylethyl and the like.

"Halogen" or "halo" refers to fluorine, chlorine, bromine or iodine. Dihaloaryl, dihaloalkyl, trihaloaryl etc. refer to aryl and alkyl substituted with a plurality of halogens, but not necessarily a plurality of the same halogen; thus 4-chloro-3-fluorophenyl is within the scope of dihaloaryl.

"Heteroaryl" encompasses:

5- to 7-membered aromatic, monocyclic rings containing one or more, for example, from 1 to 4, or in certain embodiments, from 1 to 3, heteroatoms chosen from N, O, and S, with the remaining ring atoms being carbon;

bicyclic heterocycloalkyl rings containing one or more, for example, from 1 to 4, or in certain embodiments, from 1 to 3, heteroatoms chosen from N, O, and S, with the remaining ring atoms being carbon and wherein at least one heteroatom is present in an aromatic ring; and tricyclic heterocycloalkyl rings containing one or more, for example, from 1 to 5, or in certain embodiments, from 1 to 4, heteroatoms chosen from N, O, and S, with the remaining ring atoms being carbon and wherein at least one heteroatom is present in an aromatic ring.

For example, heteroaryl includes a 5- to 7-membered heterocycloalkyl, aromatic ring fused to a 5- to 7-membered cycloalkyl or heterocycloalkyl ring. For such fused, bicyclic heteroaryl ring systems wherein only one of the rings contains one or more heteroatoms, the point of attachment may be at either ring. When the total number of S and O atoms in the heteroaryl group exceeds 1, those heteroatoms are not adjacent to one another. In certain embodiments, the total number of S and O atoms in the heteroaryl group is not more than 2. In certain embodiments, the total number of S and O atoms in the aromatic heterocycle is not more than 1. Examples of heteroaryl groups include, but are not limited to, (as numbered from the linkage position assigned priority 1), 2-pyridyl, 3-pyridyl, 4-pyridyl, 2,3-pyrazinyl, 3,4-pyrazinyl, 2,4-pyrimidinyl, 3,5-pyrimidinyl, 2,3-pyrazolyl, 2,4-imidazolinyl, isoxazolinyl, oxazolinyl, thiazolinyl, thiadiazolinyl, tetrazolyl, thienyl, benzothiophenyl, furanyl, benzofuranyl, benzoimidazolinyl, indolinyl, pyridazinyl, triazolyl, quinolinyl, pyrazolyl, and 5,6,7,8-tetrahydroisoquinolinyl. Bivalent radicals derived from univalent heteroaryl radicals whose names end in "-yl" by removal of one hydrogen atom from the atom with the free valence are named by adding "-idene" to the name of the corresponding univalent radical, e.g., a pyridyl group with two points of attachment is a pyridylidene. Heteroaryl does not encompass or overlap with aryl, cycloalkyl, or heterocycloalkyl, as defined herein Substituted heteroaryl also includes ring systems substituted with one or more oxide (—O$^-$) substituents, such as pyridinyl N-oxides.

By "heterocycloalkyl" is meant a single, non-aromatic ring, usually with 3 to 7 ring atoms, containing at least 2 carbon atoms in addition to 1-3 heteroatoms independently selected from oxygen, sulfur, and nitrogen, as well as combinations comprising at least one of the foregoing heteroatoms. The ring may be saturated or have one or more carbon-carbon double bonds. Suitable heterocycloalkyl groups include, for example (as numbered from the linkage position assigned priority 1), 2-pyrrolidinyl, 2,4-imidazolidinyl, 2,3-pyrazolidinyl, 2-piperidyl, 3-piperidyl, 4-piperidyl, and 2,5-piperizinyl. Morpholinyl groups are also contemplated, including 2-morpholinyl and 3-morpholinyl (numbered wherein the oxygen is assigned priority 1). Substituted heterocycloalkyl also includes ring systems substituted with one or more oxo (=O) or oxide (—O$^-$) substituents, such as piperidinyl N-oxide, morpholinyl-N-oxide, 1-oxo-1-thiomorpholinyl and 1,1-dioxo-1-thiomorpholinyl.

"Heterocycloalkyl" also includes bicyclic ring systems wherein one non-aromatic ring, usually with 3 to 7 ring atoms, contains at least 2 carbon atoms in addition to 1-3 heteroatoms independently selected from oxygen, sulfur, and nitrogen, as well as combinations comprising at least one of the foregoing heteroatoms; and the other ring, usually with 3 to 7 ring atoms, optionally contains 1-3 heteratoms independently selected from oxygen, sulfur, and nitrogen and is not aromatic.

"Isomers" are different compounds that have the same molecular formula. "Stereoisomers" are isomers that differ only in the way the atoms are arranged in space. "Enantiomers" are a pair of stereoisomers that are non-superimposable mirror images of each other. A 1:1 mixture of a pair of enantiomers is a "racemic" mixture. The term "(.±.)" is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R-S system. When a compound is a pure enantiomer the stereochemistry at each chiral carbon can be specified by either R or S. Resolved compounds whose absolute configuration is unknown can be designated (+) or (−) depending on the direction (dextro- or levorotatory) which they rotate plane polarized light at the wavelength of the sodium D line. Certain of the compounds described herein contain one or more asymmetric centers and can thus give rise to enantiomers, diastereomers, and other stereoisomeric forms that can be defined, in terms of absolute stereochemistry, as (R)- or (S)-. The present invention is meant to include all such possible isomers, including racemic mixtures, optically pure forms and intermediate mixtures. Optically active (R)- and (S)-isomers can be prepared using chiral synthons or chiral reagents, or resolved using conventional techniques. When the compounds described herein contain olefinic double bonds or other centers of geometric asymmetry, and unless specified otherwise, it is intended that the compounds include both E and Z geometric isomers.

"Tautomers" are structurally distinct isomers that interconvert by tautomerization. "Tautomerization" is a form of isomerization and includes prototropic or proton-shift tautomerization, which is considered a subset of acid-base chemistry. "Prototropic tautomerization" or "proton-shift tautomerization" involves the migration of a proton accompanied by changes in bond order, often the interchange of a single bond with an adjacent double bond. Where tautomerization is possible (e.g. in solution), a chemical equilibrium of tautomers can be reached. An example of tautomerization is keto-enol tautomerization. A specific example of keto-enol tautomerization is the interconverision of pentane-2,4-dione and 4-hydroxypent-3-en-2-one tautomers. Another example of tautomerization is phenol-keto tautomerization. A specific example of phenol-keto tautomerization is the interconverision of pyridin-4-ol and pyridin-4(1H)-one tautomers. Compounds of Formula I and compounds of Formula II are tautomeric.

A leaving group or atom is any group or atom that will, under the reaction conditions, cleave from the starting material, thus promoting reaction at a specified site. Suitable examples of such groups unless otherwise specified are halogen atoms, mesyloxy, p-nitrobenzensulphonyloxy and tosyloxy groups.

The term "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

Protecting group has the meaning conventionally associated with it in organic synthesis, i.e. a group that selectively blocks one or more reactive sites in a multifunctional compound such that a chemical reaction can be carried out selectively on another unprotected reactive site and such that the group can readily be removed after the selective reaction is complete. A variety of protecting groups are disclosed, for example, in T. H. Greene and P. G. M. Wuts, Protective Groups in Organic Synthesis, Third Edition, John Wiley & Sons, New York (1999). For example, a hydroxy protected form is where at least one of the hydroxy groups present in a compound is protected with a hydroxy protecting group. Likewise, amines and other reactive groups may similarly be protected.

The term "pharmaceutically acceptable salt" refers to salts that retain the biological effectiveness and properties of the compounds described herein and, which are not biologically or otherwise undesirable. In many cases, the compounds described herein are capable of forming acid and/or base salts by virtue of the presence of amino and/or carboxyl groups or groups similar thereto. Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, aluminum, and the like. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine. In some embodiments, the pharmaceutically acceptable base addition salt is chosen from ammonium, potassium, sodium, calcium, and magnesium salts.

The term "solvate" refers to a compound (e.g., a compound selected from Formula I and Formula II, or a pharmaceutically acceptable salt thereof) in physical association with one or more molecules of a pharmaceutically acceptable solvent. It will be understood that "a compound of Formula I" and "a compound of Formula II" encompass the compound of Formula I and the compound of Formula II, and solvates of those compounds, as well as mixtures thereof.

The terms "substituted" alkyl, cycloalkyl, aryl, heterocycloalkyl, and heteroaryl, unless otherwise expressly defined, refer respectively to alkyl, cycloalkyl, aryl, heterocycloalkyl, and heteroaryl wherein one or more (such as up to 5, for example, up to 3) hydrogen atoms are replaced by a substituent independently chosen from:

—$R^a$, —$OR^b$, optionally substituted amino (including —$NR^cCOR^b$, —$NR^cCO_2R^a$, —$NR^cCONR^bR^c$, —$NR^bC(NR^c)NR^bR^c$, —$NR^bC(NCN)NR^bR^c$, and —$NR^cSO_2R^a$), halo, cyano, nitro, oxo (as a substitutent for cycloalkyl, heterocycloalkyl, and heteroaryl), optionally substituted acyl (such as —$COR^b$), optionally substituted alkoxycarbonyl (such as —$CO_2R^b$), aminocarbonyl (such as —$CONR^bR^c$), —$OCOR^b$, —$OCO_2R^a$, —$OCONR^bR^c$, —$OCONR^bR^c$, —$OP(O)(OR^b)OR^c$, sulfanyl (such as $SR^b$), sulfinyl (such as —$SOR^a$), and sulfonyl (such as —$SO_2R^a$ and —$SO_2NR^bR^c$), where $R^a$ is chosen from optionally substituted $C_1$-$C_6$ alkyl, optionally substituted cycloalkyl, optionally substituted heterocycloalkyl, optionally substituted alkenyl, optionally substituted alkynyl, optionally substituted aryl, and optionally substituted heteroaryl;

$R^b$ is chosen from hydrogen, optionally substituted $C_1$-$C_6$ alkyl, optionally substituted cycloalkyl, optionally substituted heterocycloalkyl, optionally substituted aryl, and optionally substituted heteroaryl; and $R^c$ is independently chosen from hydrogen and optionally substituted $C_1$-$C_4$ alkyl; or $R^b$ and $R^c$, and the nitrogen to which they are attached, form an optionally substituted heterocycloalkyl group; and where each optionally substituted group is unsubstituted or independently substituted with one or more, such as one, two, or three, substituents independently selected from $C_1$-$C_4$ alkyl, aryl, heteroaryl, aryl-$C_1$-$C_4$ alkyl-, heteroaryl-$C_1$-$C_4$ alkyl-, $C_1$-$C_4$ haloalkyl, —$OC_1$-$C_4$ alkyl, —$OC_1$-$C_4$ alkylphenyl, —$C_1$-$C_4$ alkyl-OH, —$OC_1$-$C_4$ haloalkyl, halo, —OH, —$NH_2$, —$C_1$-$C_4$ alkyl-$NH_2$, —$N(C_1$-$C_4$ alkyl)($C_1$-$C_4$ alkyl), —$NH(C_1$-$C_4$ alkyl), —$N(C_1$-$C_4$ alkyl)($C_1$-$C_4$ alkylphenyl), —$NH(C_1$-$C_4$ alkylphenyl), cyano, nitro, oxo (as a substitutent for cycloalkyl or heterocycloalkyl), —$CO_2H$, —$C(O)OC_1$-$C_4$ alkyl, —$CON(C_1$-$C_4$ alkyl)($C_1$-$C_4$ alkyl), —$CONH(C_1$-$C_4$ alkyl), —$CONH_2$, —$NHC(O)(C_1$-$C_4$ alkyl), —$NHC(O)(phenyl)$, —$N(C_1$-$C_4$ alkyl)$C(O)(C_1$-$C_4$ alkyl), —$N(C_1$-$C_4$ alkyl)$C(O)(phenyl)$, —$C(O)C_1$-$C_4$ alkyl, —$C(O)C_1$-$C_4$ alkylphenyl, —$C(O)C_1$-$C_4$ haloalkyl, —OC (O)$C_1$-$C_4$ alkyl, —$SO_2$($C_1$-$C_4$ alkyl), —$SO_2$(phenyl), —$SO_2$($C_1$-$C_4$ haloalkyl), —$SO_2NH_2$, —$SO_2$NH($C_1$-$C_4$ alkyl), —$SO_2$NH(phenyl), —NHSO$_2$($C_1$-$C_4$ alkyl), —NHSO$_2$(phenyl), and —NHSO$_2$($C_1$-$C_4$ haloalkyl).

The term "sulfanyl" refers to the groups: —S-(optionally substituted alkyl), —S-(optionally substituted cycloalkyl), —S-(optionally substituted aryl), —S-(optionally substituted heteroaryl), and —S-(optionally substituted heterocycloalkyl).

The term "sulfinyl" refers to the groups: —S(O)—H, —S(O)-(optionally substituted alkyl), —S(O)-(optionally substituted cycloalkyl), —S(O)-(optionally substituted amino), —S(O)-(optionally substituted aryl), —S(O)-(optionally substituted heteroaryl), and —S(O)-(optionally substituted heterocycloalkyl).

The term "sulfonyl" refers to the groups: —S($O_2$)—H, —S($O_2$)-(optionally substituted alkyl), —S($O_2$)-(optionally substituted cycloalkyl), —S($O_2$)-(optionally substituted amino), —S($O_2$)-(optionally substituted aryl), —S($O_2$)-(optionally substituted heteroaryl), and —S($O_2$)-(optionally substituted heterocycloalkyl).

The term "therapeutically effective amount" or "effective amount" refers to that amount of a compound selected from Formula I and Formula II that is sufficient to effect treatment, as defined below, when administered to a mammal in need of such treatment. The therapeutically effective amount will vary depending upon the subject and disease condition being treated, the weight and age of the subject, the severity of the disease condition, the particular compound selected from Formula I and Formula II, the dosing regimen to be followed, timing of administration, the manner of administration and the like, all of which can readily be determined by one of ordinary skill in the art.

"ATPase" refers to an enzyme that hydrolyzes ATP. ATPases include proteins comprising molecular motors such as the myosins.

As used herein, "frailty" is a syndrome characterized by meeting three of the of the following five attributes: unintentional weight loss, muscle weakness, slow walking speed, exhaustion, and low physical activity.

As used herein, "cachexia" means a metabolic defect often associated with cancer that is characterized by progressive weight loss due to the deletion of adipose tissue and skeletal muscle.

As used herein, "muscle spasm" means an involuntary contraction of a muscle. Muscle spasms may lead to cramps.

As used herein, "post-surgical muscle weakness" refers to a reduction in the strength of one or more muscles following surgical procedure. Weakness may be generalized (i.e. total body weakness) or localized to a specific area, side of the body, limb, or muscle.

As used herein, "post-traumatic muscle weakness" refers to a reduction in the strength of one or more muscles following a traumatic episode (e.g. bodily injury). Weakness may be generalized (i.e. total body weakness) or localized to a specific area, side of the body, limb, or muscle.

As used herein, "neuromuscular disease" means any disease that affects any part of the nerve and muscle. Neuromuscular disease encompasses critical illness polyneuropathy, prolonged neuromuscular blockade, acute myopathy as well as acute inflammatory demyelinating polyradiculoneuropathy, amyotrophic lateral sclerosis (ALS), autonomic neuropathy, Charcot-Marie-Tooth disease and other hereditary motor and sensory neuropathies, chronic inflammatory demyelinating polyradiculoneuropathy, dermatomyositis/polymyositis, diabetic neuropathy, dystrophinopathies, endocrine myopathies, focal muscular atrophies, hemifacial spasm, hereditary neuropathies of the Charcot-Marie-Tooth disease type, inclusion body myositis, Kennedy disease, Lambert-Eaton myasthenic syndrome, muscular dystrophy (e.g., limb-girdle, Duchenne, Becker, myotonic, facioscapulohumeral, etc.), metabolic myopathies, metabolic neuropathy, multifocal motor neuropathy with conduction blocks, myasthenia gravis, neuropathy of Friedreich Ataxia, neuropathy of leprosy, nutritional neuropathy, periodic paralyses, primary lateral sclerosis, restrictive lung disease, sarcoidosis and neuropathy, Schwartz-Jampel Syndrome, spinal muscle atrophy, stiff person syndrome, thyroid disease, traumatic peripheral nerve lesions, vasculitic neuropathy, among others.

As used herein "obesity" means having a body mass index (BMI) greater than or equal to 30 kg/m$^2$. BMI is defined as weight (kg) divided by height (m$^2$). Obesity encompasses hyperplastic obesity, an increase in the number of fat cells, and hypertrophic obesity, an increase in the size of the fat cells. Overweight is defined as having a BMI from 25 up to 30 kg/m$^2$; obesity as a BMI greater than or equal to 30 kg/m$^2$, as stated above, and severe (or morbid) obesity is defined as a BMI greater than or quality to 40 kg/m$^2$.

As used herein, "sarcopenia" means a loss of skeletal muscle mass, quality, and strength. Often sarcopenia is attributed to ageing, but is also associated with HIV infection. Sarcopenia may lead to frailty, for example, in the elderly.

As used herein, "wasting syndrome" means a condition characterized by involuntary weight loss associated with chronic fever and diarrhea. In some instances, patients with wasting syndrome lose 10% of baseline body weight within one month.

Compounds of Formula I and compounds of Formula II also include crystalline and amorphous forms of those compounds, including, for example, polymorphs, pseudopolymorphs, solvates, hydrates, unsolvated polymorphs (including anhydrates), conformational polymorphs, and amorphous forms of the compounds, as well as mixtures thereof. "Crystalline form," "polymorph," and "novel form" may be used interchangeably herein, and are meant to include all crystalline and amorphous forms of the compound, including, for example, polymorphs, pseudopolymorphs, solvates, hydrates, unsolvated polymorphs (including anhydrates), conformational polymorphs, and amorphous forms, as well as mixtures thereof, unless a particular crystalline or amorphous form is referred to.

Chemical entities include, but are not limited to, compounds of Formula I, compounds of Formula II, and all pharmaceutically acceptable forms thereof. Pharmaceutically acceptable forms of the compounds recited herein include pharmaceutically acceptable salts, chelates, non-covalent complexes, prodrugs, and mixtures thereof. In certain embodiments, the compounds described herein are in the form of pharmaceutically acceptable salts. Hence, the terms "chemical entity" and "chemical entities" also encompass pharmaceutically acceptable salts, chelates, non-covalent complexes, prodrugs, and mixtures.

"Pharmaceutically acceptable salts" include, but are not limited to salts with inorganic acids, such as hydrochlorate, phosphate, diphosphate, hydrobromate, sulfate, sulfinate, nitrate, and like salts; as well as salts with an organic acid, such as malate, maleate, fumarate, tartrate, succinate, citrate, acetate, lactate, methanesulfonate, p-toluenesulfonate, 2-hydroxyethylsulfonate, benzoate, salicylate, stearate, and alkanoate such as acetate, HOOC—(CH$_2$)$_n$—COON where n ranges from 0 to 4, and like salts. Similarly, pharmaceutically acceptable cations include, but are not limited to sodium, potassium, calcium, aluminum, lithium, and ammonium.

In addition, if the compound of Formula I or the compound of Formula II is obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used to prepare non-toxic pharmaceutically acceptable addition salts.

As noted above, prodrugs also fall within the scope of chemical entities, for example, ester or amide derivatives of the compounds selected from Formula I and Formula II. The term "prodrug" includes any compound that becomes a compound of Formula I or a compound of Formula II when administered to a patient, e.g., upon metabolic processing of the prodrug. Examples of prodrugs include, but are not limited to, acetate, formate, benzoate, and like derivatives of functional groups (such as alcohol or amine groups) in the compounds selected from Formula I and Formula II.

The term "chelate" refers to the chemical entity formed by the coordination of a compound to a metal ion at two (or more) points.

The term "non-covalent complex" refers to the chemical entity formed by the interaction of a compound and another molecule wherein a covalent bond is not formed between the compound and the molecule. For example, complexation can occur through van der Waals interactions, hydrogen bonding, and electrostatic interactions (also called ionic bonding).

The term "active agent" is used to indicate a chemical entity which has biological activity. In certain embodiments, an "active agent" is a compound having pharmaceutical utility.

The term "therapeutically effective amount" of a chemical entity means an amount effective, when administered to a human or non-human patient, to treat a disease, e.g., a therapeutically effective amount may be an amount sufficient to treat a disease or disorder responsive to myosin activation. The therapeutically effective amount may be ascertained experimentally, for example by assaying blood concentration of the chemical entity, or theoretically, by calculating bioavailability.

By "significant" is meant any detectable change that is statistically significant in a standard parametric test of statistical significance such as Student's T-test, where p<0.05.

"Patient" refers to an animal, such as a mammal, for example a human, that has been or will be the object of treatment, observation or experiment. The methods described herein can be useful in both human therapy and veterinary applications. In some embodiments, the patient is a mammal, and in some embodiments, the patient is human.

"Treatment" or "treating" means any treatment of a disease in a patient, including:
(a) preventing the disease, that is, causing the clinical symptoms of the disease not to develop;
(b) inhibiting the disease;
(c) slowing or arresting the development of clinical symptoms; and/or
(d) relieving the disease, that is, causing the regression of clinical symptoms.

As used herein, "modulation" refers to a change in one or more of skeletal myosin, skeletal actin, skeletal tropomyosin, skeletal troponin C, skeletal troponin I, skeletal troponin T, and skeletal muscle, including fragments and isoforms thereof, as well as the skeletal sarcomere as a direct or indirect response to the presence of at least one chemical entity described herein, relative to the activity of the myosin or sarcomere in the absence of the compound. The change may be an increase in activity (potentiation) or a decrease in activity (inhibition), and may be due to the direct interaction of the compound with myosin or the sarcomere, or due to the interaction of the compound with one or more other factors that in turn effect one or more of skeletal myosin, skeletal actin, skeletal tropomyosin, skeletal troponin C, skeletal troponin I, skeletal troponin T, and skeletal muscle, including fragments and isoforms thereof, as well as the skeletal sarcomere.

Provided is at least one chemical entity chosen from compounds of Formula I and compounds of Formula II:

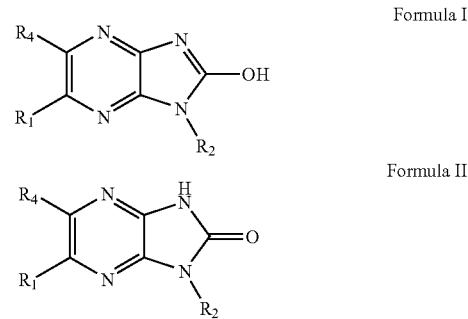

Formula I

Formula II and pharmaceutically acceptable salts thereof, wherein
$R_1$ and $R_4$ are independently selected from hydrogen, halo, hydroxy, optionally substituted acyl, optionally substituted alkyl, optionally substituted amino, optionally substituted alkenyl, optionally substituted alkynyl, optionally substituted cycloalkyl, optionally substituted heteroaryl, optionally substituted alkoxy, optionally substituted aminocarbonyl, sulfonyl, sulfanyl, sulfinyl, carboxy, optionally substituted alkoxycarbonyl, and cyano; and in the alternative, $R_4$ and $R_1$, taken together with any intervening atoms, form a fused ring system selected from optionally substituted fused aryl, optionally substituted fused heteroaryl, optionally substituted fused cycloalkyl, and optionally substituted fused heterocycloalkyl; and $R_2$ is is selected from optionally substituted alkyl, optionally substituted cycloalkyl, optionally substituted aryl, optionally substituted heteroaryl, and optionally substituted heterocycloalkyl;
provided that
$R_1$ is not hex-1-enyl; and further provided that
the compound of Formula I or the compound of Formula II is not
(S)-6-bromo-1-(1-phenylethyl)-1H-imidazo[4,5-b]pyrazin-2(3H)-one;
1,5,6-trimethyl-1H-imidazo[4,5-b]pyrazin-2(3H)-one;
1-methyl-1H-imidazo[4,5-b]pyrazin-2(3H)-one;
6-bromo-1-(3-nitrobenzyl)-1H-imidazo[4,5-b]pyrazin-2(3H)-one;
5-(hydroxymethyl)-1,6-dimethyl-1H-imidazo[4,5-b]pyrazin-2(3H)-one; or
1-(piperidin-4-yl)-1H-imidazo[4,5-b]pyrazin-2(3H)-one.

In some embodiments, $R_2$ is selected from optionally substituted lower alkyl, optionally substituted cycloalkyl, optionally substituted alkoxy, and optionally substituted heterocycloalkyl.

In some embodiments, $R_2$ is selected from heterocycloalkyl, cycloalkyl, lower alkyl, and lower alkyl substituted with optionally substituted phenyl, hydroxy, optionally substituted alkoxy, optionally substituted amino and optionally substituted heterocycloalkyl.

In some embodiments, $R_2$ is selected from 1-(R)-phenylethyl, 1-(S)-phenylethyl, benzyl, 3-pentyl, 4-heptyl, 4-methyl-1-morpholinopentan-2-yl isobutyl, cyclohexyl, cyclopropyl, sec-butyl, tert-butyl, isopropyl, 1-hydroxybutan-2-yl, tetrahydro-2H-pyran-4-yl, 1-methoxybutan-2-yl, 1-aminobutan-2-yl, and 1-morpholinobutan-2-yl.

In some embodiments, $R_1$ is selected from hydrogen, halo, acyl, optionally substituted lower alkyl, optionally substituted amino, optionally substituted pyrazolyl, optionally substituted alkenyl, optionally substituted alkynyl, optionally substituted lower alkoxy, and -S-(optionally substituted lower alkyl).

In some embodiments, $R_1$ is selected from hydrogen, halo, acyl, optionally substituted lower alkyl, dialkylamino, amino substituted with an alkyl group and with a group chosen from acyl, aminocarbonyl, alkoxycarbonyl, and sulfonyl; optionally substituted pyrazolyl, optionally substituted alkenyl, optionally substituted alkynyl, optionally substituted lower alkoxy, and —S-(optionally substituted lower alkyl).

In some embodiments, $R_1$ is selected from hydrogen, halo, acyl, alkenyl, alkynyl, lower alkoxy, optionally substituted amino, pyrazolyl substituted with lower alkyl, —S-(optionally substituted lower alkyl), lower alkyl, and lower alkyl substituted with halo.

In some embodiments, $R_1$ is selected from hydrogen, halo, acyl, alkenyl, alkynyl, lower alkoxy, dialkylamino, amino substituted with an alkyl group and with a group chosen from acyl, aminocarbonyl, alkoxycarbonyl, and sulfonyl, pyrazolyl substituted with lower alkyl, —S-(optionally substituted lower alkyl), lower alkyl, and lower alkyl substituted with halo.

In some embodiments, $R_1$ is selected from hydrogen, bromo, chloro, fluoro, methyl, ethyl, propyl, hexenyl, butenyl, propenyl, vinyl, ethynyl, methoxy, ethoxy, methylsulfanyl, dimethylamino, and methyl substituted with up to three fluoro groups.

In some embodiments, $R_1$ is selected from hydrogen, bromo, chloro, fluoro, methyl, ethyl, n-propyl, isopropyl, dimethylamino, isobuten-1-yl, (Z)-propen-1-yl, (E)-propen-1-yl, propen-2-yl, vinyl, ethynyl, methoxy, ethoxy, methylsulfanyl, and trifluoromethyl.

In some embodiments, $R_4$ is selected from hydrogen, halo, acyl, optionally substituted alkyl, alkenyl, optionally substituted cycloalkyl, optionally substituted aminocarbonyl, sulfanyl, optionally substituted amino, and optionally substituted alkoxycarbonyl.

In some embodiments, $R_4$ is selected from hydrogen, halo, acyl, optionally substituted lower alkyl, lower alkenyl, optionally substituted cycloalkyl, optionally substituted aminocarbonyl, sulfanyl, optionally substituted amino, and optionally substituted lower alkoxycarbonyl.

In some embodiments, $R_4$ is selected from hydrogen, halo, acyl, lower alkyl, lower alkenyl, cycloalkyl, optionally substituted aminocarbonyl, sulfanyl, and lower alkoxycarbonyl.

In some embodiments, $R_4$ is selected from hydrogen, bromo, chloro, fluoro, acetyl, methyl, ethyl, vinyl, cyclohexen-1-yl, methylcarbamoyl, dimethylcarbamoyl, methylsulfanyl, and methoxycarbonyl.

In some embodiments, $R_4$ is hydrogen.

In some embodiments, $R_4$ and $R_1$, taken together with any intervening atoms, form a fused ring system selected from optionally substituted fused aryl, optionally substituted fused cycloalkyl, and optionally substituted fused heterocycloalkyl.

In some embodiments, $R_4$ and $R_1$ are taken together to form an optionally substituted benzo group.

In some embodiments, $R_4$ and $R_1$ are taken together to form a benzo group.

In some embodiments, the compound of Formula I is chosen from 1-((1R)-1-methyl-2-morpholin-4-ylethyl)-6-bromoimidazo[4,5-b]pyrazin-2-ol;
1-(ethylpropyl)-6-ethynylimidazo[4,5-b]pyrazin-2-ol;
1-(ethylpropyl)-6-methoxyimidazo[4,5-b]pyrazin-2-ol;
1-(1,1-dimethyl-2-morpholin-4-ylethyl)-6-bromoimidazo[4,5-b]pyrazin-2-ol;
6-(1H-1,2,3-triazol-4-yl)-1-(ethylpropyl)imidazo[4,5-b]pyrazin-2-ol;
1-(ethylpropyl)-6-(trifluoromethyl)imidazo[4,5-b]pyrazin-2-ol;
1-[(1R)-1-(morpholin-4-ylmethyl)propyl]-6-ethynylimidazo[4,5-b]pyrazin-2-ol;
1-(ethylpropyl)-6-{2-[1-(ethylpropyl)-2-hydroxyimidazo[4,5-e]pyrazin-6-yl]ethynyl}imidazo[4,5-b]pyrazin-2-ol;
6-(dimethylamino)-1-(ethylpropyl)imidazo[4,5-b]pyrazin-2-ol;
6-ethyl-1-(ethylpropyl)imidazo[4,5-b]pyrazin-2-ol;
(E)-1-(pentan-3-yl)-6-(prop-1-enyl)-1H-imidazo[4,5-b]pyrazin-2-ol;
(E)-1-cyclohexyl-6-(prop-1-enyl)-1H-imidazo[4,5-b]pyrazin-2-ol;
(E)-1-cyclopropyl-6-(prop-1-enyl)-1H-imidazo[4,5-b]pyrazin-2-ol;
(E)-1-isopropyl-6-(prop-1-enyl)-1H-imidazo[4,5-b]pyrazin-2-ol;
(E)-6-(prop-1-enyl)-1-(tetrahydro-2H-pyran-4-yl)-1H-imidazo[4,5-b]pyrazin-2-ol;
(R)-6-(methylthio)-1-(1-phenylethyl)-1H-imidazo[4,5-b]pyrazin-2-ol;
(R)-6-bromo-1-(1-hydroxybutan-2-yl)-1H-imidazo[4,5-b]pyrazin-2-ol;
(R)-6-bromo-1-(1-morpholinobutan-2-yl)-1H-imidazo[4,5-b]pyrazin-2-ol;
(R)-6-bromo-1-(1-morpholinopropan-2-yl)-1H-imidazo[4,5-b]pyrazin-2-ol;
(R)-6-bromo-1-(1-phenylethyl)-1H-imidazo[4,5-b]pyrazin-2-ol;
(R)-6-bromo-1-sec-butyl-1H-imidazo[4,5-b]pyrazin-2-ol;
(S)-(2-hydroxy-1-(1-phenylethyl)-1H-imidazo[4,5-b]pyrazin-6-yl)(4-methylpiperazin-1-yl)methanone;
(S)-(2-hydroxy-1-(1-phenylethyl)-1H-imidazo[4,5-b]pyrazin-6-yl)(morpholino)methanone;
(S)-(2-hydroxy-1-(1-phenylethyl)-1H-imidazo[4,5-b]pyrazin-6-yl)(piperidin-1-yl)methanone;
(S)-1-(1-phenylethyl)-1H-imidazo[4,5-b]pyrazin-2-ol;
(S)-1-(1-phenylethyl)-1H-imidazo[4,5-b]quinoxalin-2-ol;
(S)-1-(1-phenylethyl)-6-(piperidin-1-ylmethyl)-1H-imidazo[4,5-b]pyrazin-2-ol;
(S)-1-(1-phenylethyl)-6-propyl-1H-imidazo[4,5-b]pyrazin-2-ol;
(S)-1-(1-phenylethyl)-6-vinyl-1H-imidazo[4,5-b]pyrazin-2-ol;
(S)-1-(2-hydroxy-1-(1-phenylethyl)-1H-imidazo[4,5-b]pyrazin-6-yl)ethanone;
(S)-2-hydroxy-1-(1-phenylethyl)-1H-imidazo[4,5-b]pyrazine-6-carbonitrile;
(S)-2-hydroxy-1-(1-phenylethyl)-1H-imidazo[4,5-b]pyrazine-6-carboxamide;
(S)-2-hydroxy-1-(1-phenylethyl)-1H-imidazo[4,5-b]pyrazine-6-carboxylic acid;

(S)-2-hydroxy-N,N-dimethyl-1-(1-phenylethyl)-1H-imidazo[4,5-b]pyrazine-6-carboxamide;
(S)-2-hydroxy-N-methyl-1-(1-phenylethyl)-1H-imidazo[4,5-b]pyrazine-6-carboxamide;
(S)-6-((4-methylpiperazin-1-yl)methyl)-1-(1-phenylethyl)-1H-imidazo[4,5-b]pyrazin-2-ol;
(S)-6-((dimethylamino)methyl)-1-(1-phenylethyl)-1H-imidazo[4,5-b]pyrazin-2-ol;
(S)-6-(2-hydroxypropan-2-yl)-1-(1-phenylethyl)-1H-imidazo[4,5-b]pyrazin-2-ol;
(S)-6-(2-methylprop-1-enyl)-1-(1-phenylethyl)-1H-imidazo[4,5-b]pyrazin-2-ol;
(S)-6-(methylsulfonyl)-1-(1-phenylethyl)-1H-imidazo[4,5-b]pyrazin-2-ol;
(S)-6-(methylthio)-1-(1-phenylethyl)-1H-imidazo[4,5-b]pyrazin-2-ol;
(S)-6-(morpholinomethyl)-1-(1-phenylethyl)-1H-imidazo[4,5-b]pyrazin-2-ol;
(S)-6-bromo-1-(1-hydroxybutan-2-yl)-1H-imidazo[4,5-b]pyrazin-2-ol;
(S)-6-bromo-1-(1-morpholinobutan-2-yl)-1H-imidazo[4,5-b]pyrazin-2-ol;
(S)-6-bromo-1-(1-morpholinopropan-2-yl)-1H-imidazo[4,5-b]pyrazin-2-ol;
(S)-6-bromo-1-(1-phenylethyl)-1H-imidazo[4,5-b]pyrazin-2-ol;
(S)-6-bromo-1-sec-butyl-1H-imidazo[4,5-b]pyrazin-2-ol;
(S)-6-cyclohexenyl-1-(1-phenylethyl)-1H-imidazo[4,5-b]pyrazin-2-ol;
(S)-6-cyclohexyl-1-(1-phenylethyl)-1H-imidazo[4,5-b]pyrazin-2-ol;
(S)-6-ethoxy-1-(1-phenylethyl)-1H-imidazo[4,5-b]pyrazin-2-ol;
(S)-6-ethyl-1-(1-phenylethyl)-1H-imidazo[4,5-b]pyrazin-2-ol;
(S)-6-hexyl-1-(1-phenylethyl)-1H-imidazo[4,5-b]pyrazin-2-ol;
(S)-6-isobutyl-1-(1-phenylethyl)-1H-imidazo[4,5-b]pyrazin-2-ol;
(S)-6-methoxy-1-(1-phenylethyl)-1H-imidazo[4,5-b]pyrazin-2-ol;
(S)-methyl 2-hydroxy-1-(1-phenylethyl)-1H-imidazo[4,5-b]pyrazine-6-carboxylate;
(S)—N,N-diethyl-2-hydroxy-1-(1-phenylethyl)-1H-imidazo[4,5-b]pyrazine-6-carboxamide;
(S)—N-benzyl-2-hydroxy-1-(1-phenylethyl)-1H-imidazo[4,5-b]pyrazine-6-carboxamide;
(S,E)-1-(1-phenylethyl)-6-(prop-1-enyl)-1H-imidazo[4,5-b]pyrazin-2-ol;
(S,Z)-1-(1-phenylethyl)-6-(prop-1-enyl)-1H-imidazo[4,5-b]pyrazin-2-ol;
(S,Z)-6-(hex-2-enyl)-1-(1-phenylethyl)-1H-imidazo[4,5-b]pyrazin-2-ol;
(Z)-1-(pentan-3-yl)-6-(prop-1-enyl)-1H-imidazo[4,5-b]pyrazin-2-ol;
(Z)-1-cyclohexyl-6-(prop-1-enyl)-1H-imidazo[4,5-b]pyrazin-2-ol;
(Z)-1-cyclopropyl-6-(prop-1-enyl)-1H-imidazo[4,5-b]pyrazin-2-ol;
(Z)-1-isopropyl-6-(prop-1-enyl)-1H-imidazo[4,5-b]pyrazin-2-ol;
(Z)-6-(prop-1-enyl)-1-(tetrahydro-2H-pyran-4-yl)-1H-imidazo[4,5-b]pyrazin-2-ol;
1-(1-aminobutan-2-yl)-6-bromo-1H-imidazo[4,5-b]pyrazin-2-ol;
1-(1-morpholinobutan-2-yl)-1H-imidazo[4,5-b]pyrazin-2-ol;
1-(2-hydroxy-1-(pentan-3-yl)-1H-imidazo[4,5-b]pyrazin-5-yl)ethanone;
1-(pentan-3-yl)-1H-imidazo[4,5-b]pyrazin-2-ol;
1-(pentan-3-yl)-1H-imidazo[4,5-b]pyrazine-2,6-diol;
1-(pentan-3-yl)-1H-imidazo[4,5-b]quinoxalin-2-ol;
1-(pentan-3-yl)-5-vinyl-1H-imidazo[4,5-b]pyrazin-2-ol;
1-(pentan-3-yl)-6-(prop-1-ynyl)-1H-imidazo[4,5-b]pyrazin-2-ol;
1-(pentan-3-yl)-6-(trifluoromethyl)-1H-imidazo[4,5-b]pyrazin-2-ol;
1-benzyl-6-(methylthio)-1H-imidazo[4,5-b]pyrazin-2-ol;
1-benzyl-6-bromo-1H-imidazo[4,5-b]pyrazin-2-ol;
1-cyclohexyl-6-(methylthio)-1H-imidazo[4,5-b]pyrazin-2-ol;
1-cyclopropyl-6-(methylthio)-1H-imidazo[4,5-b]pyrazin-2-ol;
1-isopropyl-6-(methylthio)-1H-imidazo[4,5-b]pyrazin-2-ol;
2-(6-bromo-2-hydroxy-1H-imidazo[4,5-b]pyrazin-1-yl)-1-morpholinobutan-1-one;
2-(6-bromo-2-hydroxy-1H-imidazo[4,5-b]pyrazin-1-yl)butanoic acid;
2-(6-bromo-2-hydroxy-1H-imidazo[4,5-b]pyrazin-1-yl)propane-1,3-diol;
2-hydroxy-1-(pentan-3-yl)-1H-imidazo[4,5-b]pyrazine-5-carboxylic acid;
2-hydroxy-1-(pentan-3-yl)-1H-imidazo[4,5-b]pyrazine-6-carbonitrile;
2-hydroxy-N,N-dimethyl-1-(pentan-3-yl)-1H-imidazo[4,5-b]pyrazine-5-carboxamide;
2-hydroxy-N-methyl-1-(pentan-3-yl)-1H-imidazo[4,5-b]pyrazine-5-carboxamide;
5-(methylthio)-1-(pentan-3-yl)-1H-imidazo[4,5-b]pyrazin-2-ol;
5-bromo-1-(pentan-3-yl)-1H-imidazo[4,5-b]pyrazin-2-ol;
5-ethyl-1-(pentan-3-yl)-1H-imidazo[4,5-b]pyrazin-2-ol;
6-(methylsulfinyl)-1-((S)-1-phenylethyl)-1H-imidazo[4,5-b]pyrazin-2-ol;
6-(methylthio)-1-(pentan-3-yl)-1H-imidazo[4,5-b]pyrazin-2-ol;
6-(methylthio)-1-(tetrahydro-2H-pyran-4-yl)-1H-imidazo[4,5-b]pyrazin-2-ol;
6-bromo-1-(1-(4-(methylsulfonyl)piperazin-1-yl)butan-2-yl)-1H-imidazo[4,5-b]pyrazin-2-ol;
6-bromo-1-(1-(4-methylpiperazin-1-yl)butan-2-yl)-1H-imidazo[4,5-b]pyrazin-2-ol;
6-bromo-1-(1-(dimethylamino)butan-2-yl)-1H-imidazo[4,5-b]pyrazin-2-ol;
6-bromo-1-(1-(methylamino)butan-2-yl)-1H-imidazo[4,5-b]pyrazin-2-ol;
6-bromo-1-(1-methoxybutan-2-yl)-1H-imidazo[4,5-b]pyrazin-2-ol;
6-bromo-1-(2-methyl-1-morpholinopropan-2-yl)-1H-imidazo[4,5-b]pyrazin-2-ol;
6-bromo-1-(2-morpholinoethyl)-1H-imidazo[4,5-b]pyrazin-2-ol;
6-bromo-1-(pentan-3-yl)-1H-imidazo[4,5-b]pyrazin-2-ol;
6-bromo-1-(tetrahydro-2H-pyran-4-yl)-1H-imidazo[4,5-b]pyrazin-2-ol;
6-bromo-1-cyclohexyl-1H-imidazo[4,5-b]pyrazin-2-ol;
6-bromo-1-cyclopropyl-1H-imidazo[4,5-b]pyrazin-2-ol;
6-bromo-1-isopropyl-1H-imidazo[4,5-b]pyrazin-2-ol;
6-bromo-1-tert-butyl-1H-imidazo[4,5-b]pyrazin-2-ol;
6-cyclopropyl-1-(pentan-3-yl)-1H-imidazo[4,5-b]pyrazin-2-ol;
6-ethynyl-1-(pentan-3-yl)-1H-imidazo[4,5-b]pyrazin-2-ol;

6-methoxy-1-(pentan-3-yl)-1H-imidazo[4,5-b]pyrazin-2-ol;
6-methyl-1-(pentan-3-yl)-1H-imidazo[4,5-b]pyrazin-2-ol;
methyl 2-hydroxy-1-(pentan-3-yl)-1H-imidazo[4,5-b]pyrazine-5-carboxylate;
methyl 4-(2-(6-bromo-2-hydroxy-1H-imidazo[4,5-b]pyrazin-1-yl)butyl)piperazine-1-carboxylate;
1-(ethylpropyl)-6-(1-methylpyrazol-4-yl)imidazo[4,5-b]pyrazin-2-ol;
6-bromo-1-(propylbutyl)imidazo[4,5-b]pyrazin-2-ol;
1-[(1R)-3-methyl-1-(morpholin-4-ylmethyl)buty1]-6-bromoimidazo[4,5-b]pyrazin-2-ol;
1-(ethylpropyl)-6-vinylimidazo[4,5-b]pyrazin-2-ol;
1-(ethylpropyl)-6-(1-methylvinyl)imidazo[4,5-b]pyrazin-2-ol;
1-(ethylpropyl)-6-(methylethyl)imidazo[4,5-b]pyrazin-2-ol;
6-chloro-1-(ethylpropyl)imidazo[4,5-b]pyrazin-2-ol; and
6-(dimethylamino)-1-(ethylpropyl)imidazo[4,5-b]pyrazin-2-ol.

In some embodiments, the compound of Formula II is chosen from the following tautomers of compounds of Formula I:

(R)-6-bromo-1-(1-morpholinopropan-2-yl)-1H-imidazo[4,5-b]pyrazin-2(3H)-one;
6-ethynyl-1-(pentan-3-yl)-1H-imidazo[4,5-b]pyrazin-2(3H)-one;
6-methoxy-1-(pentan-3-yl)-1H-imidazo[4,5-b]pyrazin-2(3H)-one;
6-bromo-1-(2-methyl-1-morpholinopropan-2-yl)-1H-imidazo[4,5-b]pyrazin-2(3H)-one;
1-(pentan-3-yl)-6-(1H-1,2,3-triazol-4-yl)-1H-imidazo[4,5-b]pyrazin-2(3H)-one;
1-(pentan-3-yl)-6-(trifluoromethyl)-1H-imidazo[4,5-b]pyrazin-2(3H)-one;
(R)-6-ethynyl-1-(1-morpholinobutan-2-yl)-1H-imidazo[4,5-b]pyrazin-2(3H)-one;
6-((2-hydroxy-1-(pentan-3-yl)-1H-imidazo[4,5-b]pyrazin-6-yl)ethynyl)-1-(pentan-3-yl)-1H-imidazo[4,5-b]pyrazin-2(3H)-one;
6-(dimethylamino)-1-(pentan-3-yl)-1H-imidazo[4,5-b]pyrazin-2(3H)-one;
6-ethyl-1-(pentan-3-yl)-1H-imidazo[4,5-b]pyrazin-2(3H)-one;
(E)-1-(pentan-3-yl)-6-(prop-1-enyl)-1H-imidazo[4,5-b]pyrazin-2(3H)-one;
(E)-1-cyclohexyl-6-(prop-1-enyl)-1H-imidazo[4,5-b]pyrazin-2(3H)-one;
(E)-1-cyclopropyl-6-(prop-1-enyl)-1H-imidazo[4,5-b]pyrazin-2(3H)-one;
(E)-1-isopropyl-6-(prop-1-enyl)-1H-imidazo[4,5-b]pyrazin-2(3H)-one;
(E)-6-(prop-1-enyl)-1-(tetrahydro-2H-pyran-4-yl)-1H-imidazo[4,5-b]pyrazin-2(3H)-one;
(R)-6-(methylthio)-1-(1-phenylethyl)-1H-imidazo[4,5-b]pyrazin-2(3H)-one;
(R)-6-bromo-1-(1-hydroxybutan-2-yl)-1H-imidazo[4,5-b]pyrazin-2(3H)-one;
(R)-6-bromo-1-(1-morpholinobutan-2-yl)-1H-imidazo[4,5-b]pyrazin-2(3H)-one;
(R)-6-bromo-1-(1-morpholinopropan-2-yl)-1H-imidazo[4,5-b]pyrazin-2(3H)-one;
(R)-6-bromo-1-(1-phenylethyl)-1H-imidazo[4,5-b]pyrazin-2(3H)-one;
(R)-6-bromo-1-sec-butyl-1H-imidazo[4,5-b]pyrazin-2(3H)-one;
(S)-1-(1-phenylethyl)-1H-imidazo[4,5-b]pyrazin-2(3H)-one;
(S)-1-(1-phenylethyl)-1H-imidazo[4,5-b]quinoxalin-2(3H)-one;
(S)-1-(1-phenylethyl)-6-(piperidin-1-ylmethyl)-1H-imidazo[4,5-b]pyrazin-2(3H)-one;
(S)-1-(1-phenylethyl)-6-(piperidine-1-carbonyl)-1H-imidazo[4,5-b]pyrazin-2(3H)-one;
(S)-1-(1-phenylethyl)-6-propyl-1H-imidazo[4,5-b]pyrazin-2(3H)-one;
(S)-1-(1-phenylethyl)-6-vinyl-1H-imidazo[4,5-b]pyrazin-2(3H)-one;
(S)-2-oxo-3-(1-phenylethyl)-2,3-dihydro-1H-imidazo[4,5-b]pyrazine-5-carbonitrile;
(S)-2-oxo-3-(1-phenylethyl)-2,3-dihydro-1H-imidazo[4,5-b]pyrazine-5-carboxamide;
(S)-2-oxo-3-(1-phenylethyl)-2,3-dihydro-1H-imidazo[4,5-b]pyrazine-5-carboxylic acid;
(S)-6-((4-methylpiperazin-1-yl)methyl)-1-(1-phenylethyl)-1H-imidazo[4,5-b]pyrazin-2(3H)-one;
(S)-6-((dimethylamino)methyl)-1-(1-phenylethyl)-1H-imidazo[4,5-b]pyrazin-2(3H)-one;
(S)-6-(2-hydroxypropan-2-yl)-1-(1-phenylethyl)-1H-imidazo[4,5-b]pyrazin-2(3H)-one;
(S)-6-(2-methylprop-1-enyl)-1-(1-phenylethyl)-1H-imidazo[4,5-b]pyrazin-2(3H)-one;
(S)-6-(4-methylpiperazine-1-carbonyl)-1-(1-phenylethyl)-1H-imidazo[4,5-b]pyrazin-2(3H)-one;
(S)-6-(methylsulfonyl)-1-(1-phenylethyl)-1H-imidazo[4,5-b]pyrazin-2(3H)-one;
(S)-6-(methylthio)-1-(1-phenylethyl)-1H-imidazo[4,5-b]pyrazin-2(3H)-one;
(S)-6-(morpholine-4-carbonyl)-1-(1-phenylethyl)-1H-imidazo[4,5-b]pyrazin-2(3H)-one;
(S)-6-(morpholinomethyl)-1-(1-phenylethyl)-1H-imidazo[4,5-b]pyrazin-2(3H)-one;
(S)-6-acetyl-1-(1-phenylethyl)-1H-imidazo[4,5-b]pyrazin-2(3H)-one;
(S)-6-bromo-1-(1-hydroxybutan-2-yl)-1H-imidazo[4,5-b]pyrazin-2(3H)-one;
(S)-6-bromo-1-(1-morpholinobutan-2-yl)-1H-imidazo[4,5-b]pyrazin-2(3H)-one;
(S)-6-bromo-1-(1-morpholinopropan-2-yl)-1H-imidazo[4,5-b]pyrazin-2(3H)-one;
(S)-6-bromo-1-(1-phenylethyl)-1H-imidazo[4,5-b]pyrazin-2(3H)-one;
(S)-6-bromo-1-sec-butyl-1H-imidazo[4,5-b]pyrazin-2(3H)-one;
(S)-6-cyclohexenyl-1-(1-phenylethyl)-1H-imidazo[4,5-b]pyrazin-2(3H)-one;
(S)-6-cyclohexyl-1-(1-phenylethyl)-1H-imidazo[4,5-b]pyrazin-2(3H)-one;
(S)-6-ethoxy-1-(1-phenylethyl)-1H-imidazo[4,5-b]pyrazin-2(3H)-one;
(S)-6-ethyl-1-(1-phenylethyl)-1H-imidazo[4,5-b]pyrazin-2(3H)-one;
(S)-6-hexyl-1-(1-phenylethyl)-1H-imidazo[4,5-b]pyrazin-2(3H)-one;
(S)-6-isobutyl-1-(1-phenylethyl)-1H-imidazo[4,5-b]pyrazin-2(3H)-one;
(S)-6-methoxy-1-(1-phenylethyl)-1H-imidazo[4,5-b]pyrazin-2(3H)-one;
(S)-methyl 2-oxo-3-(1-phenylethyl)-2,3-dihydro-1H-imidazo[4,5-b]pyrazine-5-carboxylate;
(S)—N,N-diethyl-2-oxo-3-(1-phenylethyl)-2,3-dihydro-1H-imidazo[4,5-b]pyrazine-5-carboxamide;

(S)—N,N-dimethyl-2-oxo-3-(1-phenylethyl)-2,3-dihydro-1H-imidazo[4,5-b]pyrazine-5-carboxamide;
(S)—N-benzyl-2-oxo-3-(1-phenylethyl)-2,3-dihydro-1H-imidazo[4,5-b]pyrazine-5-carboxamide;
(S)—N-methyl-2-oxo-3-(1-phenylethyl)-2,3-dihydro-1H-imidazo[4,5-b]pyrazine-5-carboxamide;
(S,E)-1-(1-phenylethyl)-6-(prop-1-enyl)-1H-imidazo[4,5-b]pyrazin-2(3H)-one;
(S,Z)-1-(1-phenylethyl)-6-(prop-1-enyl)-1H-imidazo[4,5-b]pyrazin-2(3H)-one;
(S,Z)-6-(hex-2-enyl)-1-(1-phenylethyl)-1H-imidazo[4,5-b]pyrazin-2(3H)-one;
(Z)-1-(pentan-3-yl)-6-(prop-1-enyl)-1H-imidazo[4,5-b]pyrazin-2(3H)-one;
(Z)-1-cyclohexyl-6-(prop-1-enyl)-1H-imidazo[4,5-b]pyrazin-2(3H)-one;
(Z)-1-cyclopropyl-6-(prop-1-enyl)-1H-imidazo[4,5-b]pyrazin-2(3H)-one;
(Z)-1-isopropyl-6-(prop-1-enyl)-1H-imidazo[4,5-b]pyrazin-2(3H)-one;
(Z)-6-(prop-1-enyl)-1-(tetrahydro-2H-pyran-4-yl)-1H-imidazo[4,5-b]pyrazin-2(3H)-one;
1-(1-aminobutan-2-yl)-6-bromo-1H-imidazo[4,5-b]pyrazin-2(3H)-one;
1-(1-morpholinobutan-2-yl)-1H-imidazo[4,5-b]pyrazin-2(3H)-one;
1-(pentan-3-yl)-1H-imidazo[4,5-b]pyrazin-2(3H)-one;
1-(pentan-3-yl)-1H-imidazo[4,5-b]quinoxalin-2(3H)-one;
1-(pentan-3-yl)-5-vinyl-1H-imidazo[4,5-b]pyrazin-2(3H)-one;
1-(pentan-3-yl)-6-(prop-1-ynyl)-1H-imidazo[4,5-b]pyrazin-2(3H)-one;
1-(pentan-3-yl)-6-(trifluoromethyl)-1H-imidazo[4,5-b]pyrazin-2(3H)-one;
1-benzyl-6-(methylthio)-1H-imidazo[4,5-b]pyrazin-2(3H)-one;
1-benzyl-6-bromo-1H-imidazo[4,5-b]pyrazin-2(3H)-one;
1-cyclohexyl-6-(methylthio)-1H-imidazo[4,5-b]pyrazin-2(3H)-one;
1-cyclopropyl-6-(methylthio)-1H-imidazo[4,5-b]pyrazin-2(3H)-one;
1-isopropyl-6-(methylthio)-1H-imidazo[4,5-b]pyrazin-2(3H)-one;
2-(6-bromo-2-oxo-2,3-dihydro-1H-imidazo[4,5-b]pyrazin-1-yl)butanoic acid;
2-oxo-1-(pentan-3-yl)-2,3-dihydro-1H-imidazo[4,5-b]pyrazine-5-carboxylic acid;
2-oxo-3-(pentan-3-yl)-2,3-dihydro-1H-imidazo[4,5-b]pyrazine-5-carbonitrile;
5-(methylthio)-1-(pentan-3-yl)-1H-imidazo[4,5-b]pyrazin-2(3H)-one;
5-acetyl-1-(pentan-3-yl)-1H-imidazo[4,5-b]pyrazin-2(3H)-one;
5-bromo-1-(pentan-3-yl)-1H-imidazo[4,5-b]pyrazin-2(3H)-one;
5-ethyl-1-(pentan-3-yl)-1H-imidazo[4,5-b]pyrazin-2(3H)-one;
6-(methylsulfinyl)-1-((S)-1-phenylethyl)-1H-imidazo[4,5-b]pyrazin-2(3H)-one;
6-(methylthio)-1-(pentan-3-yl)-1H-imidazo[4,5-b]pyrazin-2(3H)-one;
6-(methylthio)-1-(tetrahydro-2H-pyran-4-yl)-1H-imidazo[4,5-b]pyrazin-2(3H)-one;
6-bromo-1-(1-(4-(methylsulfonyl)piperazin-1-yl)butan-2-yl)-1H-imidazo[4,5-b]pyrazin-2(3H)-one;
6-bromo-1-(1-(4-methylpiperazin-1-yl)butan-2-yl)-1H-imidazo[4,5-b]pyrazin-2(3H)-one;
6-bromo-1-(1-(dimethylamino)butan-2-yl)-1H-imidazo[4,5-b]pyrazin-2(3H)-one;
6-bromo-1-(1-(methylamino)butan-2-yl)-1H-imidazo[4,5-b]pyrazin-2(3H)-one;
6-bromo-1-(1,3-dihydroxypropan-2-yl)-1H-imidazo[4,5-b]pyrazin-2(3H)-one;
6-bromo-1-(1-methoxybutan-2-yl)-1H-imidazo[4,5-b]pyrazin-2(3H)-one;
6-bromo-1-(1-morpholino-1-oxobutan-2-yl)-1H-imidazo[4,5-b]pyrazin-2(3H)-one;
6-bromo-1-(2-methyl-1-morpholinopropan-2-yl)-1H-imidazo[4,5-b]pyrazin-2(3H)-one;
6-bromo-1-(2-morpholinoethyl)-1H-imidazo[4,5-b]pyrazin-2(3H)-one;
6-bromo-1-(pentan-3-yl)-1H-imidazo[4,5-b]pyrazin-2(3H)-one;
6-bromo-1-(tetrahydro-2H-pyran-4-yl)-1H-imidazo[4,5-b]pyrazin-2(3H)-one;
6-bromo-1-cyclohexyl-1H-imidazo[4,5-b]pyrazin-2(3H)-one;
6-bromo-1-cyclopropyl-1H-imidazo[4,5-b]pyrazin-2(3H)-one;
6-bromo-1-isopropyl-1H-imidazo[4,5-b]pyrazin-2(3H)-one;
6-bromo-1-tert-butyl-1H-imidazo[4,5-b]pyrazin-2(3H)-one;
6-cyclopropyl-1-(pentan-3-yl)-1H-imidazo[4,5-b]pyrazin-2(3H)-one;
6-ethynyl-1-(pentan-3-yl)-1H-imidazo[4,5-b]pyrazin-2(3H)-one;
6-hydroxy-1-(pentan-3-yl)-1H-imidazo[4,5-b]pyrazin-2(3H)-one;
6-methoxy-1-(pentan-3-yl)-1H-imidazo[4,5-b]pyrazin-2(3H)-one;
6-methyl-1-(pentan-3-yl)-1H-imidazo[4,5-b]pyrazin-2(3H)-one;
methyl 2-oxo-1-(pentan-3-yl)-2,3-dihydro-1H-imidazo[4,5-b]pyrazine-5-carboxylate;
methyl 4-(2-(6-bromo-2-oxo-2,3-dihydro-1H-imidazo[4,5-b]pyrazin-1-yl)butyl)piperazine-1-carboxylate;
N,N-dimethyl-2-oxo-1-(pentan-3-yl)-2,3-dihydro-1H-imidazo[4,5-b]pyrazine-5-carboxamide;
N-methyl-2-oxo-1-(pentan-3-yl)-2,3-dihydro-1H-imidazo[4,5-b]pyrazine-5-carboxamide;
6-(1-methyl-1H-pyrazol-4-yl)-1-(pentan-3-yl)-1H-imidazo[4,5-b]pyrazin-2(3H)-one;
6-bromo-1-(heptan-4-yl)-1H-imidazo[4,5-b]pyrazin-2(3H)-one;
(R)-6-bromo-1-(4-methyl-1-morpholinopentan-2-yl)-1H-imidazo[4,5-b]pyrazin-2(3H)-one;
1-(pentan-3-yl)-6-vinyl-1H-imidazo[4,5-b]pyrazin-2(3H)-one;
1-(pentan-3-yl)-6-(prop-1-en-2-yl)-1H-imidazo[4,5-b]pyrazin-2(3H)-one;
6-isopropyl-1-(pentan-3-yl)-1H-imidazo[4,5-b]pyrazin-2(3H)-one;
6-chloro-1-(pentan-3-yl)-1H-imidazo[4,5-b]pyrazin-2(3H)-one; and
6-(dimethylamino)-1-(pentan-3-yl)-1H-imidazo[4,5-b]pyrazin-2(3H)-one.

The compounds of Formula I can be named and numbered (e.g., using NamExpert™ available from Cheminnovation or the automatic naming feature of Chem Draw Ultra version 10.0 from Cambridge Soft Corporation) as described below. For example, the compound:

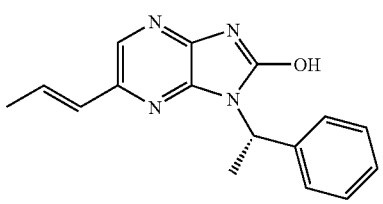

i.e., the compound according to Formula I where $R_1$ is (E)-propen-1y1, $R_2$ is (S)-sec-phenethyl, and $R_4$ is H, can be named (S,E)-1-(1-phenylethyl)-6-(prop-1-enyl)-1H-imidazo[4,5-b]pyrazin-2-ol.

Likewise the compound:

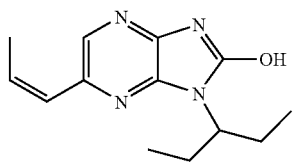

i.e., the compound according to Formula I where $R_1$ is (Z)-propen-1-yl, $R_2$ is 3-pentyl, and $R_4$ is H, can be named (Z)-1-(pentan-3-yl)-6-(prop-1-enyl)-1H-imidazo[4,5-b]pyrazin-2-ol.

Similarly, the compounds of Formula II can be named and numbered (e.g., using NamExpertTM available from Cheminnovation or the automatic naming feature of Chem Draw Ultra version 10.0 from Cambridge Soft Corporation) as described below. For example, the compound:

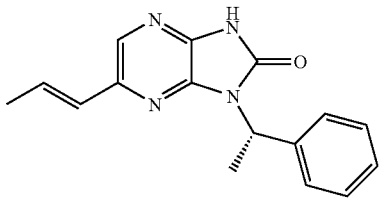

i.e., the compound according to Formula II where $R_1$ is (E)-propen-1-yl, $R_2$ is (S)-sec-phenethyl, and $R_4$ is H, can be named (S,E)-1-(1-phenylethyl)-6-(prop-1-enyl)-1H-imidazo[4,5-b]pyrazin-2(3H)-one.

Likewise the compound:

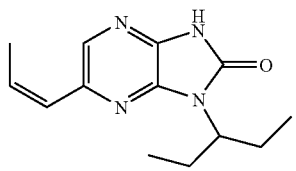

i.e., the compound according to Formula II where $R_1$ is (Z)-propen-1-yl, $R_2$ is 3-pentyl, and $R_4$ is H, can be named (Z)-1-(pentan-3-yl)-6-(prop-1-enyl)-1H-imidazo[4,5-b]pyrazin-2(3H)-one.

The chemical entities described herein can be synthesized utilizing techniques well known in the art, e.g., as illustrated below with reference to the Reaction Schemes.

Unless specified to the contrary, the reactions described herein take place at atmospheric pressure, generally within a temperature range from −10° C. to 200° C. Further, except as employed in the Examples or as otherwise specified, reaction times and conditions are intended to be approximate, e.g., taking place at about atmospheric pressure within a temperature range of about −10° C. to about 110° C. over a period of about 1 to about 24 hours; reactions left to run overnight average a period of about 16 hours.

The terms "solvent," "organic solvent," and "inert solvent" each mean a solvent inert under the conditions of the reaction being described in conjunction therewith [including, for example, benzene, toluene, acetonitrile, tetrahydrofuran ("THF"), dimethylformamide ("DMF"), chloroform, methylene chloride (or dichloromethane), diethyl ether, methanol, N-methylpyrrolidone ("NMP"), pyridine and the like]. Unless specified to the contrary, the solvents used in the reactions described herein are inert organic solvents. Unless specified to the contrary, for each gram of the limiting reagent, one cc (or mL) of solvent constitutes a volume equivalent Isolation and purification of the chemical entities and intermediates described herein can be effected, if desired, by any suitable separation or purification procedure such as, for example, filtration, extraction, crystallization, column chromatography, thin-layer chromatography or thick-layer chromatography, or a combination of these procedures. Specific illustrations of suitable separation and isolation procedures can be had by reference to the examples hereinbelow. However, other equivalent separation or isolation procedures can also be used.

When desired, the (R)- and (S)-isomers may be resolved by methods known to those skilled in the art, for example by formation of diastereoisomeric salts or complexes which may be separated, for example, by crystallization; via formation of diastereoisomeric derivatives which may be separated, for example, by crystallization, gas-liquid or liquid chromatography; selective reaction of one enantiomer with an enantiomer-specific reagent, for example enzymatic oxidation or reduction, followed by separation of the modified and unmodified enantiomers; or gas-liquid or liquid chromatography in a chiral environment, for example on a chiral support, such as silica with a bound chiral ligand or in the presence of a chiral solvent. Alternatively, a specific enantiomer may be synthesized by asymmetric synthesis using optically active reagents, substrates, catalysts or solvents, or by converting one enantiomer to the other by asymmetric transformation.

Many of the optionally substituted starting compounds and other reactants are commercially available, e.g., from Aldrich Chemical Company (Milwaukee, Wis.) or can be readily prepared by those skilled in the art using commonly employed synthetic methodology.

REACTION SCHEME 1

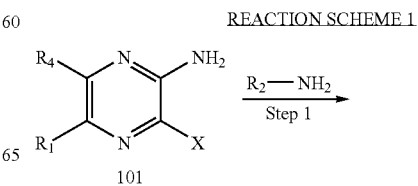

101

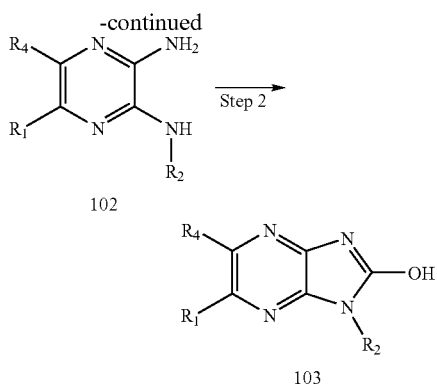

Referring to Reaction Scheme 1, Step 1, to a compound of Formula 101, wherein X is halo, is added an excess (such as about 2 to 20 equivalents) of a compound of formula $R_2$-$NH_2$. The reaction vessel is heated to about 110° C. to 190° C. over about 20 to 40 minutes, optionally with microwave irradiation. The product, a compound of Formula 102, is isolated and optionally purified.

Referring to Reaction Scheme 1, Step 2, to a solution of a compound of Formula 102 in a suitable solvent (such as THF) is added a di-activated carbonyl equivalent such as carbonyl diimidazole (CDI), phospgene, or triphosgene. The product, a compound of Formula 103, is isolated and optionally purified.

REACTION SCHEME 2

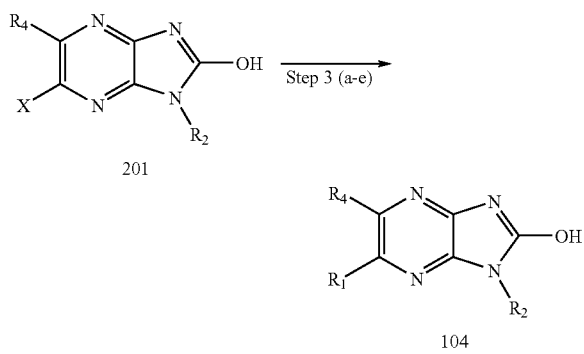

Reaction Scheme 2 illustrates reactions for further converting compounds of Formula 201, wherein X is a leaving group, to compounds of Formula 104 through one of Steps 3(a-e). In some embodiments, X is halo, for example, bromo.

Referring to Reaction Scheme 2, Step 3(a), a compound of Formula 201 and about 0.05 to 0.15 equivalents of a suitable catalyst such as $(Ph_3P)_4Pd$ in a suitable solvent such as NMP or dioxane, a suitable base, and an excess (such as about 1.5 to 32 molar equivalents) of a suitable tin reagent such as $R_1Sn(butyl)_3$ is mixed at from about 0 to about 200° C. for about 6 to 48 hours. The product, a compound of Formula 104 wherein $R_1$ is selected from optionally substituted alkyl, optionally substituted alkenyl, optionally substituted alkynyl, and optionally substituted cycloalkyl, is isolated and optionally purified.

Referring to Reaction Scheme 2, Step 3(b), a compound of Formula 201 and an excess (such as about 4 to 5 equivalents) of a compound of the formula $NaSR_x$ where $SR_x$ is $R_1$, and a suitable solvent (such as NMP) is heated to about 50° C. to 200° C. over about 10 min to 24 h, optionally with microwave irradiation. The product, a compound of Formula 104 wherein $R_1$ is sulfanyl, is isolated and optionally purified.

Referring to Reaction Scheme 2, Step 3(c), a compound of Formula 201, an excess (such as about 1.9 to 2.3 equivalents) of a compound of the formula $R_1B(OH)_2$, about 0.10 to 0.15 equivalents of $(DPPF)PdCl_2$, a suitable solvent (such as dioxane) and about 2 to 3 equivalents of a suitable base (such as 2N $K_2CO_3$) is heated to about 90° C. for about 6 to 24 hours. The product, a compound of Formula 104 wherein $R_1$ is selected from optionally substituted alkyl, optionally substituted alkenyl, optionally substituted alkynyl, and optionally substituted cycloalkyl, is isolated and optionally purified.

Referring to Reaction Scheme 2, Step 3(d), about 2 equivalents of $R_xOH$ where $OR_x$ is $R_1$ and a suitable solvent (such as NMP), and about 2 equivalents of suitable base (such as NaH) is added followed by a compound of Formula 201. The mixture is heated to about 50 to about 200° C. for about 10 minutes to about 48 hours. In some embodiments, the reaction is heated for about 30 minutes, optionally with microwave irradiation. The product, a compound of Formula 104 wherein $R_1$ is optionally substituted alkoxy, is isolated and optionally purified.

Referring to Reaction Scheme 2, Step(e), a compound of Formula 201, an excess (such as about 2.0 equivalents) of a compound of the formula $KR_1BF_3$, an excess (such as about 3 equivalents) of a suitable base (such as $Cs_2CO_3$), a suitable amount of $(DPPF)PdCl_2$ (such as about 0.2 equivalents), a suitable solvent (such as dioxane and water) is mixed at about room termperature to about 100° C. for about 8 to 48 hours and the product, a compound of Formula 104 wherein $R_1$ is selected from optionally substituted alkyl, optionally substituted alkenyl, optionally substituted alkynyl, and optionally substituted cycloalkyl, is isolated and optionally purified.

A racemic mixture is optionally placed on a chromatography column and separated into (R)- and (S)-enantiomers.

The compounds described herein are optionally contacted with a pharmaceutically acceptable acid to form the corresponding acid addition salts.

Pharmaceutically acceptable acid addition salts of compounds of Formula I or compounds of Formula II are optionally contacted with a base to form the corresponding free base.

The chemical entities described herein modulate one or more of skeletal myosin, skeletal actin, skeletal tropomyosin, skeletal troponin C, skeletal troponin I, skeletal troponin T, and skeletal muscle, including fragments and isoforms thereof, as well as the skeletal sarcomere, and are useful to bind to, inhibit and/or potentiate the activity thereof. As used in this context, "modulate" means either increasing or decreasing myosin activity, whereas "potentiate" means to increase activity and "inhibit" means to decrease activity.

The chemical entities, pharmaceutical compositions and methods described herein are used to treat obesity, sarcopenia, wasting syndrome, frailty, cachexia, muscle spasm, post-surgical and post-traumatic muscle weakness, neuromuscular disease, and other indications in a mammal.

Methods to identify the chemcial entities as binding to a protein or as a modulator of the binding characteristics or biological activity of a protein are described in, for example, U.S. Pat. No. 6,410,254 and U.S. patent application Ser. No. 10/987,165.

For example, test compounds can be assayed in a highly parallel fashion by using multiwell plates by placing the compounds either individually in wells or testing them in mixtures. Assay components including the target protein complex, coupling enzymes and substrates, and ATP can then be added to the wells and the absorbance or fluorescence of each well of the plate can be measured with a plate reader.

In some embodiments, the method uses a 384 well plate format and a 25 μL reaction volume. A pyruvate kinase/lactate dehydrogenase coupled enzyme system (Huang T G and Hackney D D. (1994) J Biol Chem 269(23):16493-501) can be used to measure the rate of ATP hydrolysis in each well. As will be appreciated by those in the art, the assay components are added in buffers and reagents. The incubation periods can be optimized to give adequate detection signals over the background. The assay can be done in real time giving the kinetics of ATP hydrolysis which increases the signal to noise ratio of the assay.

The compounds can be further tested using skinned muscle fiber preparations. Such assays are known in the art. See, e.g., Cheung et al. (2002) Nature Cell Biol. 4:83 and U.S. Patent Publication No. 20020006962.

The chemical entities described herein are administered at a therapeutically effective dosage, e.g., a dosage sufficient to provide treatment for the disease states previously described. While human dosage levels have yet to be optimized for the chemical entities described herein, generally, a daily dose ranges from about 0.05 to 100 mg/kg of body weight; in certain embodiments, from about 0.10 to 10.0 mg/kg of body weight, and in certain embodiments, from about 0.15 to 1.0 mg/kg of body weight. Thus, for administration to a 70 kg person, in certain embodiments, the dosage range would be about from 3.5 to 7000 mg per day; in certain embodiments, about from 7.0 to 700.0 mg per day, and in certain embodiments, about from 10.0 to 100.0 mg per day. The amount of the chemical entity administered will, of course, be dependent on the subject and disease state being treated, the severity of the affliction, the manner and schedule of administration and the judgment of the prescribing physician; for example, a likely dose range for oral administration would be from about 70 to 700 mg per day, whereas for intravenous administration a likely dose range would be from about 70 to 700 mg per day depending on compound pharmacokinetics.

Administration of the chemical entities described herein can be via any of the accepted modes of administration for agents that serve similar utilities including, but not limited to, orally, sublingually, subcutaneously, intravenously, intranasally, topically, transdermally, intraperitoneally, intramuscularly, intrapulmonarilly, vaginally, rectally, or intraocularly. In some embodiments, oral or parenteral administration is used.

Pharmaceutically acceptable compositions include solid, semi-solid, liquid and aerosol dosage forms, such as, e.g., tablets, capsules, powders, liquids, suspensions, suppositories, aerosols or the like. The chemical entities can also be administered in sustained or controlled release dosage forms, including depot injections, osmotic pumps, pills, transdermal (including electrotransport) patches, and the like, for prolonged and/or timed, pulsed administration at a predetermined rate. In certain embodiments, the compositions are provided in unit dosage forms suitable for single administration of a precise dose.

The chemical entities described herein can be administered either alone or more typically in combination with a conventional pharmaceutical carrier, excipient or the like (e.g., mannitol, lactose, starch, magnesium stearate, sodium saccharine, talcum, cellulose, sodium crosscarmellose, glucose, gelatin, sucrose, magnesium carbonate, and the like). If desired, the pharmaceutical composition can also contain minor amounts of nontoxic auxiliary substances such as wetting agents, emulsifying agents, solubilizing agents, pH buffering agents and the like (e.g., sodium acetate, sodium citrate, cyclodextrine derivatives, sorbitan monolaurate, triethanolamine acetate, triethanolamine oleate, and the like). Generally, depending on the intended mode of administration, the pharmaceutical composition will contain about 0.005% to 95%; in certain embodiments, about 0.5% to 50% by weight of a chemical entity. Actual methods of preparing such dosage forms are known, or will be apparent, to those skilled in this art; for example, see *Remington's Pharmaceutical Sciences*, Mack Publishing Company, Easton, Pa.

In addition, the chemical entities described herein can be co-administered with, and the pharmaceutical compositions can include, other medicinal agents, pharmaceutical agents, adjuvants, and the like. Suitable medicinal and pharmaceutical agents include modulators of one or more of skeletal myosin, skeletal actin, skeletal tropomyosin, skeletal troponin C, skeletal troponin I, skeletal troponin T, and skeletal muscle, including fragments and isoforms thereof, and the skeletal sarcomere and other suitable therapeutic agents useful in the treatment of the aforementioned disorders including: anti-obesity agents, anti-sarcopenia agents, anti-wasting syndrome agents, anti-frailty agents, anti-cachexia agents, anti-muscle spasm agents, agents against post-surgical and post-traumatic muscle weakness, and anti-neuromuscular disease agents, as well as the agents described in U.S. Patent Application No. 2005/0197367.

Suitable additional medicinal and pharmaceutical agents include, for example: orlistat, sibramine, diethylpropion, phentermine, benzaphetamine, phendimetrazine, estrogen, estradiol, levonorgestrel, norethindrone acetate, estradiol valerate, ethinyl estradiol, norgestimate, conjugated estrogens, esterified estrogens, medroxyprogesterone acetate, testosterone, insulin-derived growth factor, human growth hormone, riluzole, cannabidiol, prednisone, albuterol, non-steroidal anti-inflammatory drugs, and botulinum toxin.

Other suitable medicinal and pharmaceutical agents include TRH, diethylstilbesterol, theophylline, enkephalins, E series prostaglandins, compounds disclosed in U.S. Pat. No. 3,239,345 (e.g., zeranol), compounds disclosed in U.S. Pat. No. 4,036,979 (e.g., sulbenox), peptides disclosed in U.S. Pat. No. 4,411,890 growth hormone secretagogues such as GHRP-6, GHRP-1 (disclosed in U.S. Pat. No. 4,411,890 and publications WO 89/07110 and WO 89/07111), GHRP-2 (disclosed in WO 93/04081), NN703 (Novo Nordisk), LY444711 (Lilly), MK-677 (Merck), CP424391 (Pfizer) and B-HT920, growth hormone releasing factor and its analogs, growth hormone and its analogs and somatomedins including IGF-1 and IGF-2, alpha-adrenergic agonists, such as clonidine or serotonin 5-$HT_D$ agonists, such as sumatriptan, agents which inhibit somatostatin or its release, such as physostigmine, pyridostigmine, parathyroid hormone, PTH(1-34), and bisphosphonates, such as MK-217 (alendronate).

Still other suitable medicinal and pharmaceutical agents include estrogen, testosterone, selective estrogen receptor modulators, such as tamoxifen or raloxifene, other androgen receptor modulators, such as those disclosed in Edwards, J. P. et. al., Bio. Med. Chem. Let., 9, 1003-1008 (1999) and Hamann, L. G. et. al., J. Med. Chem., 42, 210-212 (1999), and progesterone receptor agonists ("PRA"), such as levonorgestrel, medroxyprogesterone acetate (MPA).

Still other suitable medicinal and pharmaceutical agents include aP2 inhibitors, such as those disclosed in U.S. Ser. No. 09/519,079 filed Mar. 6, 2000, PPAR gamma antagonists, PPAR delta agonists, beta 3 adrenergic agonists, such as AJ9677 (Takeda/Dainippon), L750355 (Merck), or CP331648 (Pfizer), other beta 3 agonists as disclosed in U.S. Pat. Nos. 5,541,204, 5,770,615, 5,491,134, 5,776,983 and 5,488,064, a lipase inhibitor, such as orlistat or ATL-962

(Alizyme), a serotonin (and dopamine) reuptake inhibitor, such as sibutramine, topiramate (Johnson & Johnson) or axokine (Regeneron), a thyroid receptor beta drug, such as a thyroid receptor ligand as disclosed in WO 97/21993, WO 99/00353, and GB98/284425, and anorectic agents, such as dexamphetamine, phentermine, phenylpropanolamine or mazindol.

Still other suitable medicinal and pharmaceutical agents include HIV and AIDS therapies, such as indinavir sulfate, saquinavir, saquinavir mesylate, ritonavir, lamivudine, zidovudine, lamivudine/zidovudine combinations, zalcitabine, didanosine, stavudine, and megestrol acetate.

Still other suitable medicinal and pharmaceutical agents include antiresorptive agents, hormone replacement therapies, vitamin D analogues, elemental calcium and calcium supplements, cathepsin K inhibitors, MMP inhibitors, vitronectin receptor antagonists, Src SH.sub.2 antagonists, vacular —H$^+$-ATPase inhibitors, ipriflavone, fluoride, Tibolone, pro stanoids, 17-beta hydroxysteroid dehydrogenase inhibitors and Src kinase inhibitors.

The above other therapeutic agents, when employed in combination with the chemical entities described herein, may be used, for example, in those amounts indicated in the Physicians' Desk Reference (PDR) or as otherwise determined by one of ordinary skill in the art.

In certain embodiments, the compositions will take the form of a pill or tablet and thus the composition will contain, along with the active ingredient, a diluent such as lactose, sucrose, dicalcium phosphate, or the like; a lubricant such as magnesium stearate or the like; and a binder such as starch, gum acacia, polyvinylpyrrolidine, gelatin, cellulose, cellulose derivatives or the like. In another solid dosage form, a powder, marume, solution or suspension (e.g., in propylene carbonate, vegetable oils or triglycerides) is encapsulated in a gelatin capsule.

Liquid pharmaceutically administrable compositions can, for example, be prepared by dissolving, dispersing, etc. at least one chemical entity and optional pharmaceutical adjuvants in a carrier (e.g., water, saline, aqueous dextrose, glycerol, glycols, ethanol or the like) to form a solution or suspension. Injectables can be prepared in conventional forms, either as liquid solutions or suspensions, as emulsions, or in solid forms suitable for dissolution or suspension in liquid prior to injection. The percentage of chemical entities contained in such parenteral compositions is highly dependent on the specific nature thereof, as well as the activity of the chemical entities and the needs of the subject. However, percentages of active ingredient of 0.01% to 10% in solution are employable, and will be higher if the composition is a solid which will be subsequently diluted to the above percentages. In certain embodiments, the composition will comprise from about 0.2 to 2% of the active agent in solution.

Pharmaceutical compositions of the chemical entities described herein may also be administered to the respiratory tract as an aerosol or solution for a nebulizer, or as a microfine powder for insufflation, alone or in combination with an inert carrier such as lactose. In such a case, the particles of the pharmaceutical composition have diameters of less than 50 microns, in certain embodiments, less than 10 microns.

The following examples serve to more fully describe the manner of using the above-described invention. It is understood that these examples in no way serve to limit the true scope of this invention, but rather are presented for illustrative purposes.

EXAMPLE 1

Synthesis of (S)-6-bromo-1-(1-phenylethyl)-1H-imidazo[4,5-b]pyrazin-2-ol

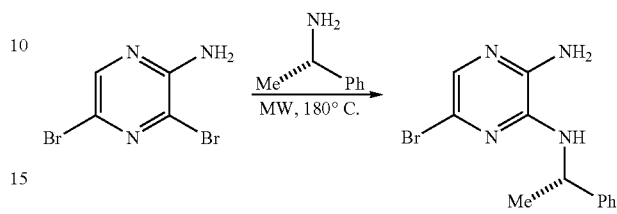

Step 1: (S)-6-bromo-N$^2$-(1-phenylethyl)pyrazine-2,3-diamine. A thick-walled microwave bottle equipped with a stirbar was charged with 1.0 equiv of 3,5-dibromopyrazin-2-amine and 6.6 equiv of (S)-sec-phenethylamine. The bottle was fitted with a septum and cap and heated to 180° C. in a microwave for 30 min. The resulting solution was adsorbed onto 20 g of silica; flash chromatography (10%-50% EtOAc/Hexanes) provided the title compound (60%) as an off-white foam. LCMS m/z (APCI)=293.0, 295.0 (M+H).

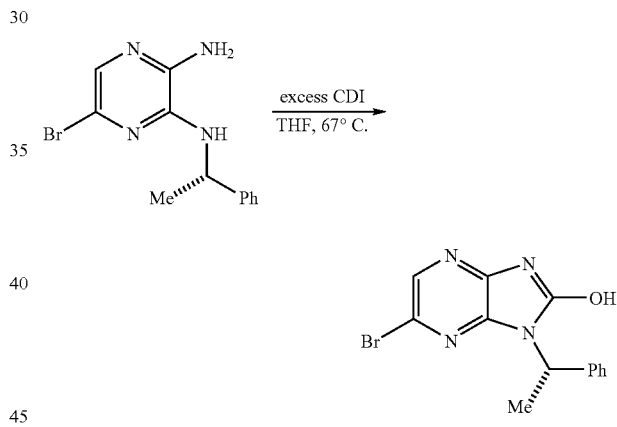

Step 2: (S)-6-bromo-1-(1-phenylethyl)-1H-imidazo[4,5-b]pyrazin-2-ol. To a solution of (S)-6-bromo-N$^2$-(1-phenylethyl)pyrazine-2,3-diamine (1.0 equiv) in refluxing anhydrous THF (5 volume equivalents) was added carbonyldiimidazole (CDI). Successive portions of CDI were added until the starting material was consumed (approx. 3.6 equiv total) as judged by TLC (50% EtOAc/Hexanes). After complete reaction, the mixture was cooled to room temperature and quenched by the careful addition of water until gas evolution had ceased. The mixture was diluted with 25 volume equivalents of EtOAc and washed with 3×7.5 volume equivalents of water and 1×7.5 volume equivalents of brine. The organic layer was dried over anhydrous sodium sulfate, filtered and concentrated in vacuo. Flash chromatography (Biotage MPLC 5%-40% EtOAc/Hexanes) provided the title compound (66%) as a white solid. LCMS m/z (APCI)=319.0, 321.0 (M+H).

EXAMPLE 1(a)

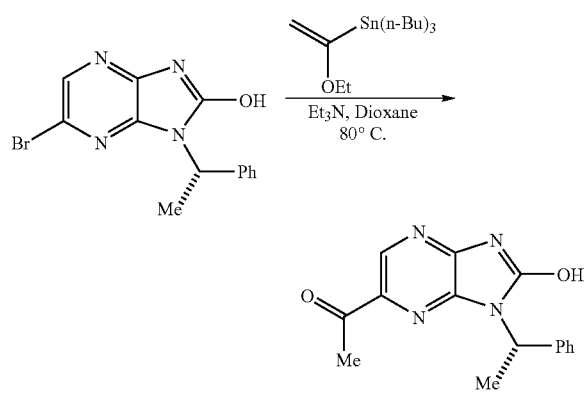

(S)-1-(2-hydroxy-1-(1-phenylethyl)-1H-imidazo[4,5-b]pyrazin-6-yl)ethanone. An oven-dried scintillation vial equipped with a stirbar was charged with (S)-6-bromo-1-(1-phenylethyl)-1H-imidazo[4,5-b]pyrazin-2-ol (1.0 equiv), and (Ph$_3$P)$_4$Pd (0.07 equiv). The bottle was covered with a sheet of Parafilm and purged with nitrogen for 5 min, and anhydous dioxane (13 volume equivalents), triethylamine (3.0 equiv), and tributyl(1-ethoxyvinyl)stannane (1.5 equiv) were added by syringe. The resulting mixture was heated to 80° C. overnight. The reaction was quenched with 1 N KHSO$_4$ and stirred for 30 min. The mixture was then diluted with EtOAc, washed twice with NaHCO$_3$ and once with brine. The organic layer was dried over sodium sulfate, filtered, and concentrated in vacuo. Flash chromatography (Biotage MPLC 10%-66% EtOAc/Hexanes) provided the title compound (33%) as a white solid. LCMS m/z (APCI) =283.1 (M+H).

EXAMPLE 1(b)

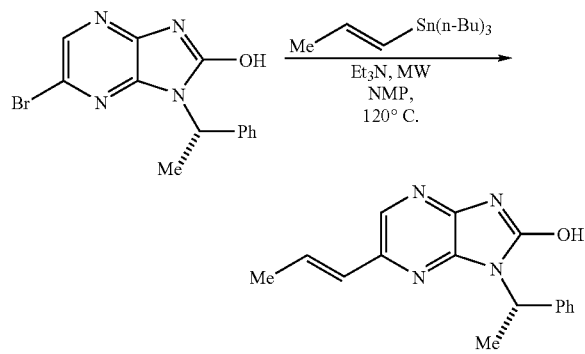

(S,E)-1-(1-phenylethyl)-6-(prop-1-enyl)-1H-imidazo[4,5-b]pyrazin-2-ol. A thick-walled microwave bottle equipped with a stirbar was charged with (S)-6-bromo-1-(1-phenylethyl)-1H-imidazo[4,5-b]pyrazin-2-ol (1.0 equiv), and (Ph$_3$P)$_4$Pd (0.12 equiv). The bottle was covered with a sheet of Parafilm and purged with nitrogen for 5 min, and N-methylpyrrolidone (14 volume equivalents), triethyl amine (2.0 equiv), and (E)-tributyl(prop-1-enyl)stannane (3.0 equiv) were added by syringe. The resulting mixture was immediately fitted with a septum and cap and heated to 120° C. in a microwave for 20 min. The reaction was then diluted with EtOAc, washed four times with saturated aq. NaHCO$_3$ and once with brine. The organic layer was dried over sodium sulfate, filtered, and concentrated in vacuo. Reverse-phase preparative HPLC provided the title compound (54%) as a foam. LCMS m/z (APCI)=281.1 (M+H).

EXAMPLE 1(c)

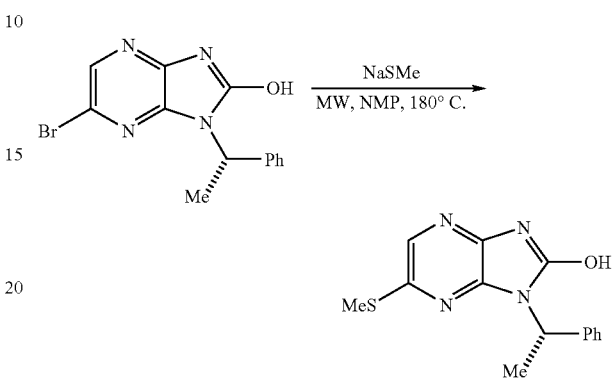

(S)-6-(methylthio)-1-(1-phenylethyl)-1H-imidazo[4,5-b]pyrazin-2-ol. A thick-walled microwave bottle equipped with a stirbar was charged with (S)-6-bromo-1-(1-phenylethyl)-1H-imidazo[4,5-b]pyrazin-2-ol (1.0 equiv), sodium thiomethoxide (4.5 equiv), and N-methylpyrrolidone (10 volume equivalents). The bottle was fitted with a septum and cap and heated to 180° C. in a microwave for 30 min. The reaction mixture was then diluted with 100 volume equivalents of EtOAc and washed with 4×100 volume equivalents of water and 1×100 volume equivalents of brine. The organic layer was dried over anhydrous sodium sulfate, filtered, and concentrated in vacuo. Reverse-phase preparative HPLC (20%-80% MeCN/H$_2$O) provided the title compound (24%) as a white solid. LCMS m/z (APCI)=287.1 (M+H).

EXAMPLE 1(d)

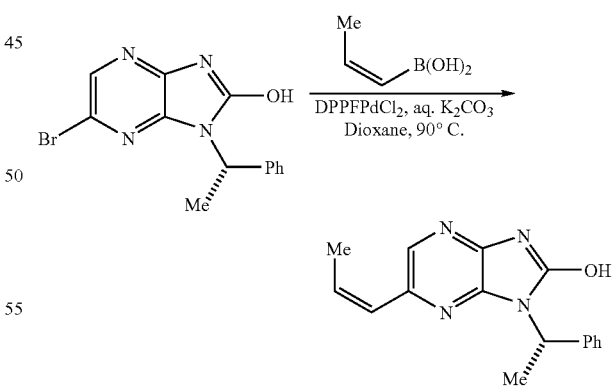

(S,Z)-1-(1-phenylethyl)-6-(prop-1-enyl)-1H-imidazo[4,5-b]pyrazin-2-ol. A scintillation vial equipped with a stirbar was charged with (S)-6-bromo-1-(1-phenylethyl)-1H-imidazo[4,5-b]pyrazin-2-ol (1.0 equiv), (Z)-prop-1-enyl boronic acid (2.0 equiv) and (DPPF)PdCl$_2$ (0.10 equiv). The vial was fitted with a septum-lined cap and purged with nitrogen for 5-10 min. To this mixture was added dioxane (16.6 volume equivalents) and degassed 2 N K$_2$CO$_3$ (4.2 volume equivalents) by syringe. The resulting mixture was heated to 90° C. overnight. The mixture was cooled to room temperature, diluted with EtOAc, washed with twice with saturated aq. NaHCO3, and once with brine. The organic layer was dried over sodium sulfate, filtered, and concentrated in vacuo. Flash chromatography (Biotage MPLC 5%-40% EtOAc/Hexanes) provided the title compound (63%) as an off-white foam. LCMS m/z (APCI)=281.1 (M+H).

EXAMPLE 1(e)

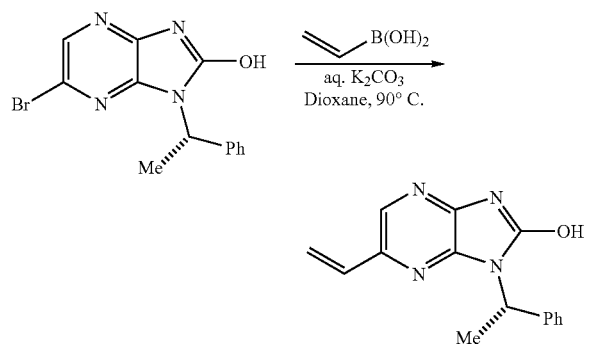

(S)-1-(1-phenylethyl)-6-vinyl-1H-imidazo[4,5-b]pyrazin-2-ol. A scintillation vial equipped with a stirbar was charged with (S)-6-bromo-1-(1-phenylethyl)-1H-imidazo[4,5-b]pyrazin-2-ol (1.0 equiv), vinyl boronic acid (2.2 equiv), and (DPPF)PdCl$_2$ (0.10 equiv). The vial was fitted with a septum-lined cap and purged with nitrogen for 5-10 min. To this mixture was added dioxane (16.6 volume equivalents) and degassed 2 N K$_2$CO$_3$ (4.2 volume equivalents) by syringe. The resulting mixture was heated to 90° C. overnight. The mixture was cooled to room temperature, diluted with 12 volume equivalents EtOAc, washed with twice with saturated aq. NaHCO$_3$, and once with brine. The organic layer was dried over sodium sulfate, filtered, and concentrated in vacuo. Flash chromatography (Biotage MPLC 5%-40% EtOAc/Hexanes) provided the title compound as an off-white solid (54%). LCMS m/z (APCI)=267.0 (M+H).

EXAMPLE 1(f)

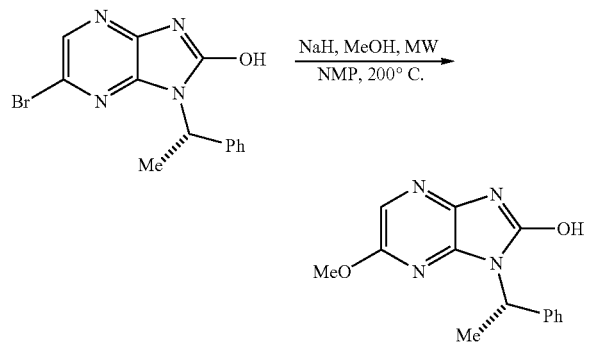

(S)-6-methoxy-1-(1-phenylethyl)-1H-imidazo[4,5-b]pyrazin-2-ol. A thick-walled microwave bottle equipped with a stirbar was charged with MeOH (2.0 equiv) and NMP (20 volume equivalents). To the resulting solution was added NaH (2.0 equiv), resulting in gas evolution. (S)-6-Bromo-1-(1-phenylethyl)-1H-imidazo[4,5-b]pyrazin-2-ol (1.0 equiv) was then added to the reaction, and the resulting mixture was immediately fitted with a septum and cap and heated to 200° C. in a microwave for 30 min. The reaction was then diluted with EtOAc, washed twice with saturated aq. NaHCO$_3$ and once with brine. The organic layer was dried over sodium sulfate, filtered, and concentrated in vacuo. Reverse-phase preparative HPLC provided the title compound (29%) as a white solid. LCMS m/z (APCI)=271.1 (M+H).

EXAMPLE 1(g)

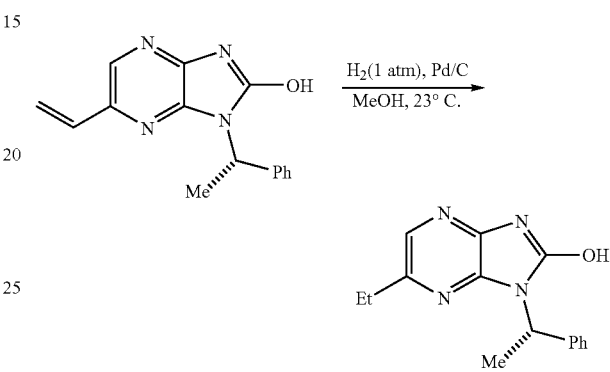

(S)-1-(1-phenylethyl)-6-ethyl-1H-imidazo[4,5-b]pyrazin-2-ol. A scintillation vial equipped with a stirbar was charged with (S)-6-vinyl-1-(1-phenylethyl)-1H-imidazo[4,5-b]pyrazin-2-ol (1.0 equiv), methanol (280 volume equivalents), and catalytic Pd/C. The resulting mixture was purged with hydrogen for 45 minutes; the reaction was complete as judged my LCMS. The mixture was then filtered through a pad of diatomaceous earth and the pad of diatomaceous earth was washed twice with MeOH. The solution was concentrated in vacuo. Flash chromatography (Biotage MPLC 5%-40% EtOAc/Hexanes) provided the title compound (86%) as a foam. LCMS m/z (APCI)=269.1 (M+H).

EXAMPLE 2

Synthesis of 6-bromo-1-(pentan-3-yl)-1H-imidazo[4,5-b]pyrazin-2-ol

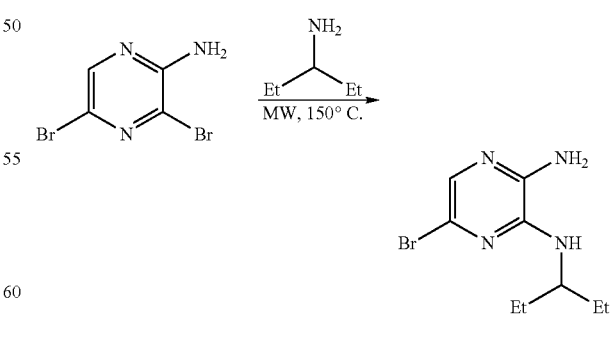

Step 1: 6-bromo-N$^2$-(pentan-3-yl)pyrazine-2,3-diamine. The title compound was prepared in a manner analogous to Example 1 Step 1 except that 3-aminopentane (2.6 volume equivalents) was substituted for (S)-sec-phenethylamine. LCMS m/z (APCI)=259.0, 260.0 (M+H).

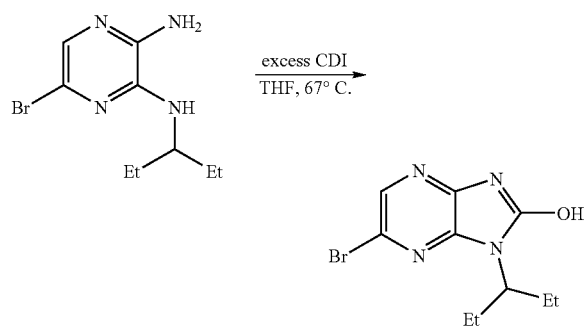

Step 2: 6-bromo-1-(pentan-3-yl)-1H-imidazo[4,5-b]pyrazin-2-ol. The title compound was prepared by treating 6-bromo-$N^2$-(pentan-3-yl)pyrazine-2,3-diamine in a manner analogous to Example 1 Step 2 LCMS m/z (APCI)=285.0, 287.0 (M+H).

EXAMPLE 2(a)

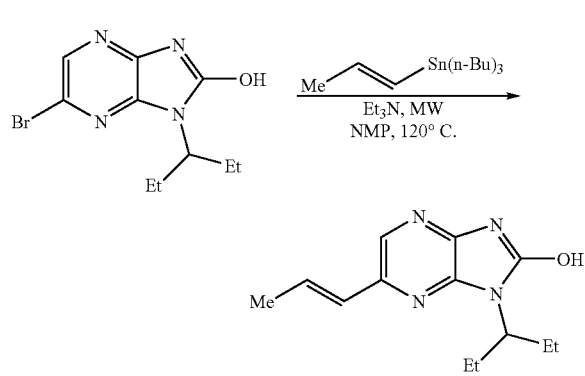

(E)-1-(pentan-3-yl)-6-(prop-1-enyl)-1H-imidazo[4,5-b]pyrazin-2-ol. A thick-walled microwave bottle equipped with a stirbar was charged with 6-bromo-1-(pentan-3-yl)-1H-imidazo[4,5-b]pyrazin-2-ol (1.0 equiv) and (Ph$_3$P)$_4$Pd (0.15 equiv). The bottle was covered with a sheet of Parafilm and purged with nitrogen for 5-10 min, and N-methylpyrrolidone (11.7 volume equivalents), triethyl amine (2.0 equiv), and (E)-tributyl(prop-1-enyl)stannane (2.0 equiv) were added by syringe. The resulting mixture was immediately fitted with a septum and cap and heated to 120° C. in a microwave for 20 min. The reaction was then diluted with EtOAc, washed with three times with water and once with brine. The organic layer was dried over sodium sulfate, filtered, and concentrated in vacuo. Reverse-phase preparative HPLC provided the title compound (15%) as a foam. LCMS m/z (APCI)=247.1 (M+H).

Example 2(b)

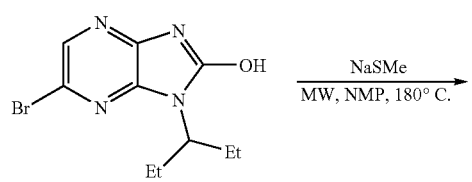

-continued

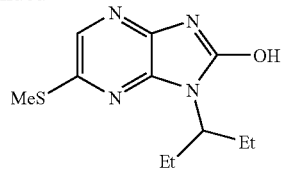

6-(methylthio)-1-(pentan-3-yl)-1H-imidazo[4,5-b]pyrazin-2-ol. The title compound was prepared by reacting 6-bromo-1-(pentan-3-yl)-1H-imidazo[4,5-b]pyrazin-2-ol (1.0 equiv), sodium thiomethoxide (1.4 equiv), and N-methylpyrrolidone (5.9 volume equivalents) in a manner analagous to Example 1(c). LCMS m/z (APCI)=253.0 (M+H).

EXAMPLE 2(c)

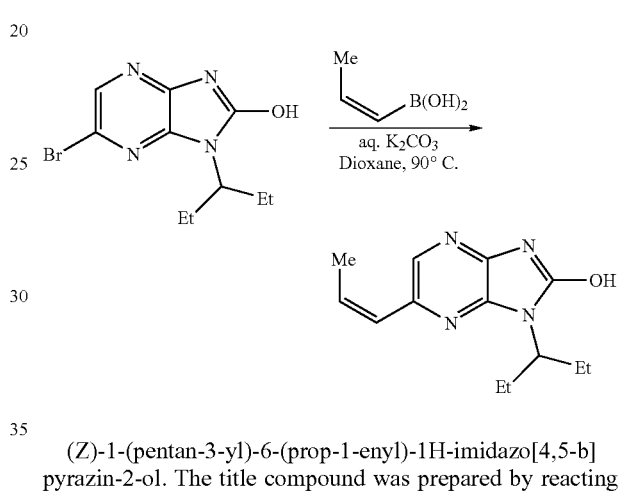

(Z)-1-(pentan-3-yl)-6-(prop-1-enyl)-1H-imidazo[4,5-b]pyrazin-2-ol. The title compound was prepared by reacting 6-bromo-1-(pentan-3-yl)-1H-imidazo[4,5-b]pyrazin-2-ol (1.0 equiv), (Z)-prop-1-enyl boronic acid (1.5 equiv) and (DPPF)PdCl$_2$ (0.15 equiv) in a manner analagous to Exmple 1(d). LCMS m/z (APCI)=247.0 (M+H).

EXAMPLE 3

Synthesis of 1-(pentan-3-yl)-1H-imidazo[4,5-b]quinoxalin-2-ol

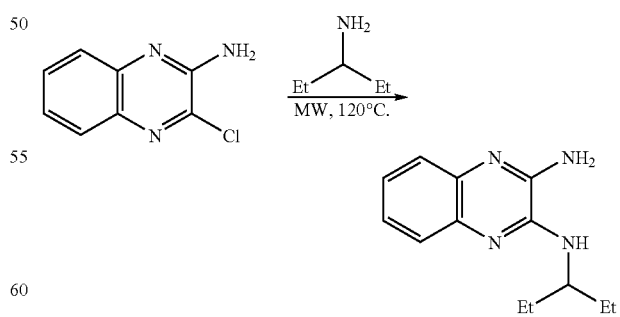

Step 1: $N^2$-(pentan-3-yl)quinoxaline-2,3-diamine. A thick-walled microwave bottle equipped with a stirbar was charged with 3-chloroquinoxalin-2-amine (1.0 equiv) and 20 volume equivalents of 3-aminopentane. The bottle was fitted with a septum and cap and heated to 120° C. in a microwave for 30 min. The resulting solution was concentrated in vacuo. Flash chromatography (20%-60% EtOAc/Hexanes) provided the title compound (78%) as a yellow solid. LCMS m/z (APCI)= 231.1 (M+H).

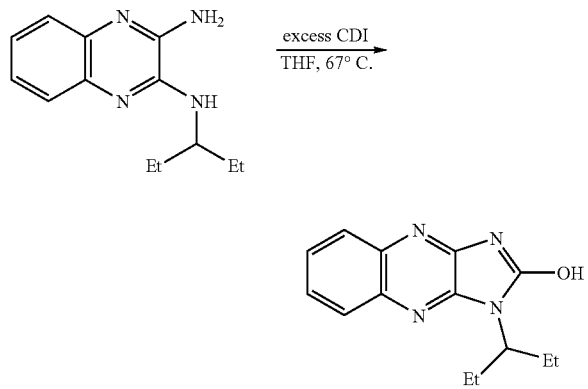

Step 2: 1-(pentan-3-yl)-1H-imidazo[4,5-b]quinoxalin-2-ol. The title compound was prepared by treating $N^2$-(pentan-3-yl)quinoxaline-2,3-diamine in a manner analogous to Example 1 Step 2 LCMS m/z (APCI)=257.2 (M+H).

EXAMPLE 3(a)

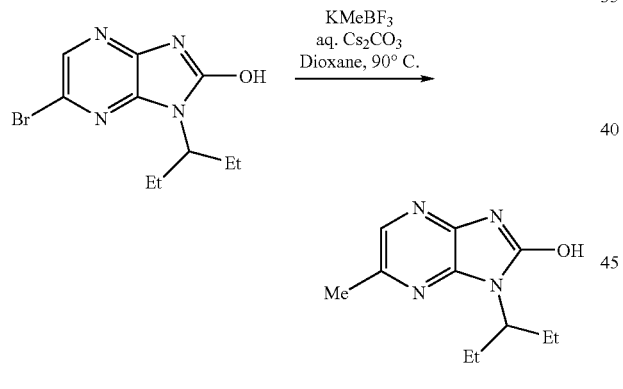

Synthesis of (Z)-1-(pentan-3-yl)-6-(prop-1-enyl)-1H-imidazo[4,5-b]pyrazin-2-ol. A scintillation vial equipped with a stirbar was charged with 6-bromo-1-(pentan-3-yl)-1H-imidazo[4,5-b]pyrazin-2-ol (1.0 equiv), $KF_3BMe$ (2.0 equiv), $Cs_2CO_3$ (3.0 eqiv) and (DPPF)PdCl$_2$ (0.20 equiv). The vial was fitted with a septum-lined cap and purged with nitrogen for 5-10 min. To this mixture was added dioxane (25 volume equivalents) and degassed water (5 volume equivalents) by syringe. The resulting mixture was heated to 90° C. overnight. The mixture was cooled to room temperature, diluted with 15 mL EtOAc, washed twice with saturated aq. NaHCO$_3$ and once with brine. The organic layer was dried over sodium sulfate, filtered, and concentrated in vacuo. Flash chromatography (Biotage MPLC 5%-40% EtOAc/Hexanes) provided the title compound (53%) as a white solid. LCMS m/z (APCI)= 221.1 (M+H).

EXAMPLE 4

Synthesis of 6-ethynyl-1-(pentan-3-yl)-1 H-imidazo[4,5-b]pyrazin-2-ol

EXAMPLE 4(a)

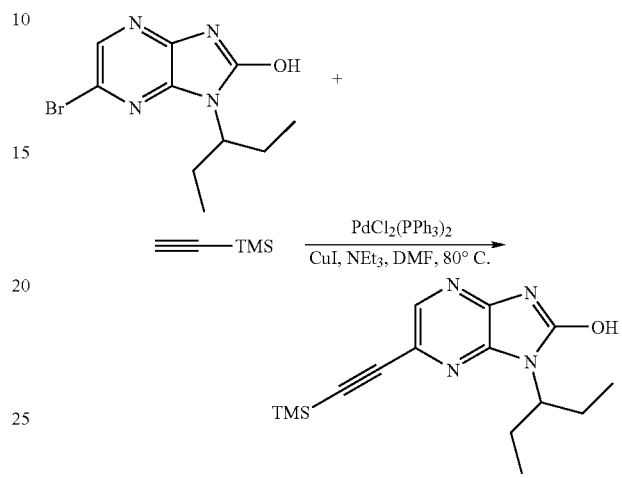

1-(pentan-3-yl)-6-((trimethylsilyl)ethynyl)-1H-imidazo[4,5-b]pyrazin-2-ol. A mixture of 6-bromo-1-(pentan-3-yl)-1H-imidazo[4,5-b]pyrazin-2-ol (3.75 g, 13.2 mmol)), trimethylsilylacetylene (2.8 mL, 19.8 mmol), PdCl$_2$(PPh)$_2$ (0.93g, 1.32 mmol), CuI (0.5 g, 2.64 mmol) and triethylamine (5.5 mL, 39.5 mmol) in DMF (50 mL) was purged with N$_2$ for 30 seconds followed by stirring at 80° C. After 3 hours the reaction mixture was diluted with EtOAc, washed with NH$_4$Cl solution, dried over Na$_2$SO$_4$, and concentrated in vacuo. Purification with over silica gel (Biotage MPLC 10-80% EtOAc/hexanes) provided the title compound (3.2 g, 80%) as a brown solid.

EXAMPLE 4(b)

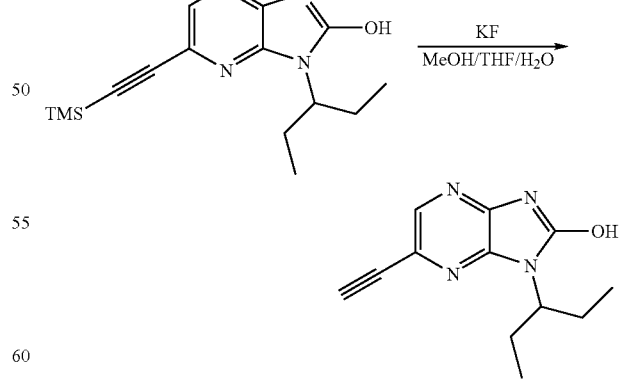

6-ethynyl-1-(pentan-3-yl)-1H-imidazo[4,5-b]pyrazin-2-ol. A mixture of 1-(pentan-3-yl)-6-((trimethylsilyl)ethynyl)-1H-imidazo[4,5-b]pyrazin-2-ol (3.2 g, 10.6 mmol), KF (1.6 g, 27.5 mmol) in MeOH/THF/H$_2$O (50 mL, 2/2/1) was stirred at room temperature. Upon complete conversion by LCMS, the solution was concentrated in vacuo, diluted with EtOAc, washed with NH₄Cl solution, dried over Na₂SO₄, and concentrated in vacuo. Purification over silica gel (Biotage MPLC 10-80% EtOAc/Heaxanes) gave a brown solid, which was washed with 15% EtOAc/hexanes to give product the title compound as a white solid (0.9 g, 37%).

EXAMPLE 5

Synthesis of 6-(dimethylamino)-1-(pentan-3-yl)-1H-imidazo[4,5-b]pyrazin-2-ol

EXAMPLE 5(a)

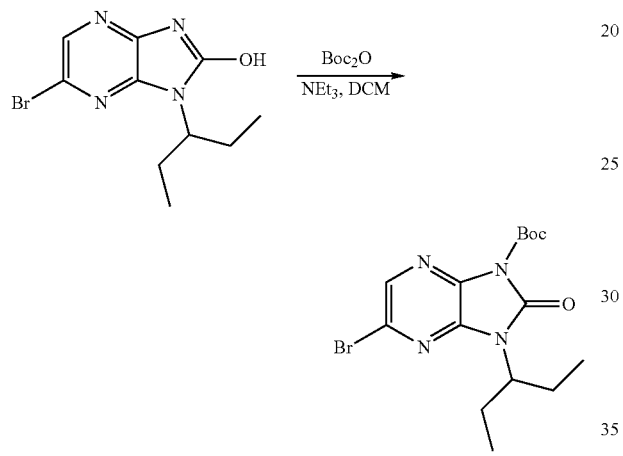

tert-butyl 5-bromo-2-oxo-3-(pentan-3-yl)-2,3-dihydroimidazo[4,5-b]pyrazine-1-carboxylate. To a solution of 6-bromo-1-(pentan-3-yl)-1H-imidazo[4,5-b]pyrazin-2-ol (5.0 g, 17.6 mmol) in DCM (80 mL) containing triethylamine (7.34 mL, 52.8 mmol) was added Boc₂O (7.0 g, 35 mmol). The reaction mixture was stirred at room temperature overnight, washed with NaHCO₃ solution, dried over Na₂SO₄ and concentrated in vacuo. Purification over silica gel (Biotage MPLC 10-50% EtOAc/hexanes) gave the desired product as a white solid (1.7 g, 25%).

EXAMPLE 5(b)

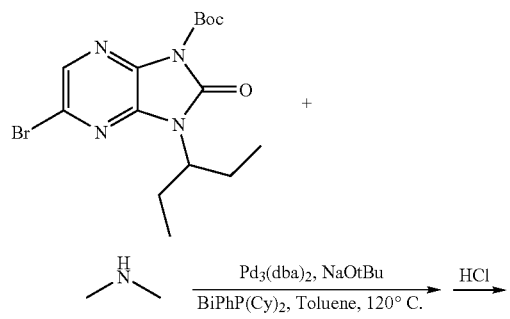

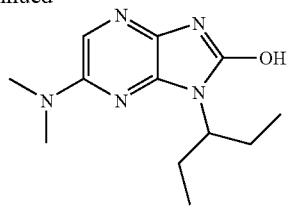

6-(dimethylamino)-1-(pentan-3-yl)-1H-imidazo[4,5-b]pyrazin-2-ol. A mixture of tert-butyl 5-bromo-2-oxo-3-(pentan-3-yl)-2,3-dihydroimidazo[4,5-b]pyrazine-1-carboxylate (200 mg, 0.52 mmol), dimethylamine (0.5 mL, 2M in THF, 1.0 mmol), Pd₃(dba)₂ (48 mg, 0.052 mmol), BiPhP(Cy)₂ (37 mg, 0.10 mmol) and NaOtBu (150 mg, 1.56 mmol) in anhydrous toluene (4 mL) was purged with N₂ for 15 second and then stirred at 120° C. for 20 minutes in microwave. The mixture was diluted with EtOAc, washed with NaHCO₃ solution, dried over Na₂SO₄, and then concentrated in vacuo to give a dark muddy residue. The residue was dissolved in MeOH (10 mL) and treated with 1 mL 4M HCl in dioxane. After one hour, the reaction was concentrated, diluted with EtOAc, washed with NaHCO₃, dried over Na₂SO₄, and concentrated in vacuo. Purification over silica gel (Biotage MPLC 10-70% EtOAc/hexanes) gave the title compound as a light yellow solid (42 mg, 32%).

EXAMPLE 6

Preparation of Sarcomeric Proteins from Skeletal Muscle

Actin was purified by first preparing an ether powder of cardiac muscle (Zot H G and Potter J D. (1981) Preparative Biochemistry 11:381-395) as described below. Subsequently, actin was cycled between the filamentous and soluble state through rounds of centrifugation and dialysis (Spudich J A and Watt S. (1971) J. Biol. Chem. 246:4866-4871). It was stored in the filamentous state at 4° C.

Tropomyosin was extracted from the ether powder and separated from the other proteins based on pH dependent precipitations followed by successive ammonium sulfate cuts at 53% and 65% (Smillie L B. (1981) Methods Enzymol 85 Pt B:234-41). The troponins were isolated as an intact complex of TnC, TnT, and TnI. Ether powder is extracted in a high salt buffer. Successive ammonium sulfate cuts of 30% and 45% were done; the precipitate was solubilized by dialysis into a low salt buffer and then further purified on a DEAE Toyopearl column with a 25-350 mM KCl gradient. There was no measurable ATPase in any of the components except for myosin which naturally had a very low basal ATPase in the absence of actin.

Just prior to screening, the actin, tropomyosin, and troponin complex are mixed together in the desired ratio (e.g., 7:1:1) to achieve maximal calcium regulation of the actin filament. The screen is conducted at a pCa=6.5. This calcium concentration is in the physiological range during muscle contraction.

To measure the generation of ADP during the reaction, a pyruvate kinase/lactate dehydrogenase/NADH coupled enzyme system (PK/LDH) is added to the actin. The myosin is kept separately. The plates are read in real time so that kinetic curves are obtained. These compounds are in DMSO and were already spotted onto the bottoms of 384 well plates at 10 to 40 µg/ml final concentration.

EXAMPLE 7

Actin Preparation

1. Extract powder (as prepared in Example 6 or 7 below) with 20 ml buffer A (see below, add BME and ATP just prior to use in each of the following steps) per gram of powder (200 ml per 10 g). Use a large 4 L beaker for 150 g of powder. Mix vigorously to dissolve powder. Stir at 4° C. for 30 min.
2. Separate extract from the hydrated powder by squeezing through several layers of cheesecloth. Cheesecloth should be pre-sterilized by microwaving damp for 1-2 min.
3. Re-extract the residue with the same volume of buffer A and combine extracts.
4. Spin in JLA10 rotor(s) for 1 hr at 10K rpm (4° C.). Collect supernatant through 2 layers of cheesecloth.
5. Add ATP to 0.2 mM and $MgCl_2$ to 50 mM. Stir on stir plate at 4° C. for 60 minutes to allow actin to polymerize/form para-crystals.
6. Slowly add solid KCl to 0.6 M (45 g/l). Stir at 4° C. for 30 min.
7. Spin in JLA10 rotor(s) at 10K rpm for 1 hr.
8. Depolymerization: Quickly rinse surface of pellets with buffer A and dispose of wash. Soften the pellets by pre-incubation on ice with small amount of buffer A in each tube (use less than half of final resuspension volume total in all tubes). Resuspend by hand first with cell scraper and combine pellets. Wash tubes with extra buffer using a 25 ml pipette and motorized pipettor, aggressively removing actin from sides of tubes. Homogenize in large dounce in cold buffer A on ice. Use 3 ml per gram of powder originally extracted.
9. Dialyze against buffer A with 4 changes over 48 hour period.
10. Collect dialyzed actin and spin in the 45Ti rotor at 40K rpm for 1.5 hr (4° C.).
11. Collect supernatant (G-Actin). Save a sample for gel analysis and determination of protein concentration.

To polymerize G-actin for storage add KCl to 50 mM (from 3 M stock), $MgCl_2$ to 1 mM, and $NaN_3$ to 0.02% (from 10% stock). Store at 4° C. Do not freeze.

Buffer A: 2 mM tris/HCl, 0.2 mM $CaCl_2$, 0.5 mM (36 µl/L) 2-mercaptoethanol, 0.2 mM $Na_2$ ATP (added fresh), and 0.005% Na-azide; pH 8.0.

EXAMPLE 8

Powder Preparation

1. Volumes are given per about 1000 g of the minced muscle.
2. Pre-cut and boil cheesecloth for 10 min in water. Drain and dry.
3. Mince chicken breast in a prechilled meat grinder.
4. Extract with stirring in 2 L of 0.1 M KCl, 0.15 M K-phosphate, pH 6.5 for 10 min at 4° C. Spin 5000 rpm, 10 min, 4° C. in JLA. Collect the pellet.
5. Extract pellets with stirring with 2 L of 0.05 M $NaHCO_3$ for 5 min. Spin 5000 rpm, 10 min, 4° C. in JLA. Collect the pellet. Repeat the extraction once more.
6. Extract the filtered residue with 2 L of 1 mM EDTA, pH 7.0 for 10 min with stirring.
7. Extract with 2 L of $H_2O$ for 5 min with stirring. Spin 10000 rpm, 15 min, 4° C. in JLA. Carefully collect the pellet, part of which will be loose and gelatinous.
8. Extract 5 times with acetone (2 L of acetone for 10 min each with stirring). Squeeze through cheesecloth gently. All acetone extractions are performed at room temperature. Acetone should be prechilled to 4° C.
9. Drying: Place the filtered residue spread on a cheesecloth in a large glass tray and leave in a hood overnight. When the residue is dry, put in a wide mouth plastic bottle and store at 20° C.

EXAMPLE 9

Alternate Powder Preparation

Based on Zot & Potter (1981) Prep. Biochem. 11(4) pp.381-395.

1. Dissect left ventricles of the cardiac muscle. Remove as much of the pericardial tissue and fat as possible. Grind in a prechilled meat grinder. Weigh.
2. Prepare 5 volumes of Extract buffer (see below). Be sure the pH=8.0. Then, homogenize the meat in a blender, 4 times 15 sec on blend with 15 secs in between. Do this with 1 volume weight/volume) of buffer taken from the 5 volumes already prepared. Add the homogenate back to the extract buffer and stir until well mixed (5 minutes).
3. Filter through one layer of cheesecloth in large polypropylene strainer. Resuspend back into 5 volumes of extract buffer as above.
4. Repeat Step 3 four more times. At the end, do not resuspend in extraction buffer but proceed to Step 5. The pellets should be yellow white.
5. Resuspend in 3 volumes (according to original weight) of 95% cold ethanol. Stir for 5 min and squeeze through cheesecloth as above, repeat two more times.
6. Weigh squeezed residue and then resuspend in 3 volumes (new weight/volume) of cold diethyl ether.
7. Repeat Step 6 a total of three times.
8. Leave overnight in a single layer on a cheesecloth in a glass tray.
9. When dry, collect the powder, weigh and store in a wide-mouth jar at 4° C.

EXTRACT BUFFER: 50 mM KCl, 5 mM Tris pH 8.0
Prepare as 50 times concentrate:
For 2L
 250 mM Tris pH 8.0. Tris Base (121.14 g/mol, 60.6 g)
 pH to 8.0 with conc. HCl, then add:
 2.5 M KCl (74.55 g/mol, 372 g)

EXAMPLE 10

Purification of Skeletal Muscle Myosin

See, Margossian, S. S. and Lowey, S. (1982) Methods Enzymol. 85, 55-123 and Goldmann, W. H. and Geeves, M. A. (1991) Anal. Biochem. 192, 55-58.

Solution A: 0.3 M KCl, 0.15 M potassium phosphate, 0.02 M EDTA, 0.005 M $MgCl_2$, 0.001 M ATP, pH 6.5.
Solution B: 1 M KCl, 0.025 M EDTA, 0.06 M potassium phosphate, pH 6.5.
Solution C: 0.6 M KCl, 0.025 M potassium phosphate, pH 6.5.
Solution D: 0.6 M KCl, 0.05 M potassium phosphate, pH 6.5.
Solution E: 0.15 M potassium phosphate, 0.01 M EDTA, pH 7.5.
Solution F: 0.04 M KCl, 0.01 M potassium phosphate, 0.001 M DTT, pH 6.5.
Solution G: 3 M KCl, 0.01 M potassium phosphate, pH 6.5.
All procedures are carried out at 4° C.

1. Obtain ~1000 g skeletal muscle, such as rabbit skeletal muscle.
2. Grind twice; extract with 2 L solution A for 15 min while stirring; add 4 L cold H₂O, filter through gauze; dilute with cold H₂O to ionic strength of 0.04, (about 10-fold); let settle for 3 h; collect precipitate at 7,000 rpm in GSA rotor for 15 min.
3. Disperse pellet in 220 ml solution B; dialyze overnight against 6 L solution C; slowly add ~400 ml equal volume cold distilled H₂O; stir for 30 min; centrifuge at 10,000 rpm for 10 min in GSA rotor.
4. Centrifuge supernatant at 19,000 rpm for 1 h.
5. Dilute supernatant to ionic strength of 0.04 (~8-fold); let myosin settle overnight; collect about 5-6 L fluffy myosin precipitate by centrifuging at 10,000 rpm for 10 min in GSA rotor.
6. Resuspend pellet in minimal volume of solution G; dialyze overnight against 2 L solution D; centrifuge at 19,000 rpm for 2 h, in cellulose nitrate tubes; puncture tubes and separate myosin from fat and insoluble pellet.
7. Dilute supernatant to 5-10 mg/ml and dialyze against solution E extensively, load onto DEAE-sephadex column.
8. Preequilibrate with solution E; apply 500-600 g myosin at 30 ml/h; wash with 350 ml solution E; elute with linear gradient of 0-0.5 M KCl in solution E (2×1 liter); collect 10 ml fractions; pool myosin fractions (>0.1 M KCl); concentrate by overnight dialysis against solution F; centrifuge at 25,000 rpm for 30 min; store as above.
9. The myosin is then cut with chymotrypsin or papain in the presence of EDTA to generate the S1 fragment which is soluble at the low salt conditions optimal for ATPase activity (Margossian supra).

EXAMPLE 11

Using procedures similar to those described herein, the compounds in the following table were synthesized and tested.

| Name | m/z | Ion | SKM MF AC1.4 (µM) |
|---|---|---|---|
| (S)-6-bromo-1-(1-phenylethyl)-1H-imidazo[4,5-b]pyrazin-2-ol | 319.0; 321.0 | [M + H]⁺; [M + H]⁺ | 0.45 |
| (S)-6-bromo-1-(1-phenylethyl)-1H-imidazo[4,5-b]pyrazin-2(3H)-one | 319.0; 321.0 | [M + H]⁺; [M + H]⁺ | 0.45 |
| (R)-6-bromo-1-(1-phenylethyl)-1H-imidazo[4,5-b]pyrazin-2-ol | 319.0; 321.0 | [M + H]⁺; [M + H]⁺ | 2.4 |
| (R)-6-bromo-1-(1-phenylethyl)-1H-imidazo[4,5-b]pyrazin-2(3H)-one | 319.0; 321.0 | [M + H]⁺; [M + H]⁺ | 2.4 |
| 1-benzyl-6-bromo-1H-imidazo[4,5-b]pyrazin-2-ol | 305.1; 307.1 | [M + H]⁺; [M + H]⁺ | 23.5 |
| 1-benzyl-6-bromo-1H-imidazo[4,5-b]pyrazin-2(3H)-one | 305.1; 307.1 | [M + H]⁺; [M + H]⁺ | 23.5 |
| (S)-6-(methylthio)-1-(1-phenylethyl)-1H-imidazo[4,5-b]pyrazin-2-ol | 287.1 | [M + H]⁺ | 1.1 |
| (S)-6-(methylthio)-1-(1-phenylethyl)-1H-imidazo[4,5-b]pyrazin-2(3H)-one | 287.1 | [M + H]⁺ | 1.1 |
| 1-benzyl-6-(methylthio)-1H-imidazo[4,5-b]pyrazin-2-ol | 273.0 | [M + H]⁺ | 22.6 |
| 1-benzyl-6-(methylthio)-1H-imidazo[4,5-b]pyrazin-2(3H)-one | 273.0 | [M + H]⁺ | 22.6 |
| (R)-6-(methylthio)-1-(1-phenylethyl)-1H-imidazo[4,5-b]pyrazin-2-ol | 287.0 | [M + H]⁺ | 2.9 |
| (R)-6-(methylthio)-1-(1-phenylethyl)-1H-imidazo[4,5-b]pyrazin-2(3H)-one | 287.0 | [M + H]⁺ | 2.9 |
| (S)-6-(2-methylprop-1-enyl)-1-(1-phenylethyl)-1H-imidazo[4,5-b]pyrazin-2-ol | 295.1 | [M + H]⁺ | 2.7 |
| (S)-6-(2-methylprop-1-enyl)-1-(1-phenylethyl)-1H-imidazo[4,5-b]pyrazin-2(3H)-one | 295.1 | [M + H]⁺ | 2.7 |
| (S)-6-cyclohexenyl-1-(1-phenylethyl)-1H-imidazo[4,5-b]pyrazin-2-ol | 321.1 | [M + H]⁺ | 31.0 |
| (S)-6-cyclohexenyl-1-(1-phenylethyl)-1H-imidazo[4,5-b]pyrazin-2(3H)-one | 321.1 | [M + H]⁺ | 31.0 |
| (S,Z)-1-(1-phenylethyl)-6-(prop-1-enyl)-1H-imidazo[4,5-b]pyrazin-2-ol | 281.1 | [M + H]⁺ | 1.0 |
| (S,Z)-1-(1-phenylethyl)-6-(prop-1-enyl)-1H-imidazo[4,5-b]pyrazin-2(3H)-one | 281.1 | [M + H]⁺ | 1.0 |
| (S)-1-(1-phenylethyl)-6-vinyl-1H-imidazo[4,5-b]pyrazin-2-ol | 267.0 | [M + H]⁺ | 2.4 |
| (S)-1-(1-phenylethyl)-6-vinyl-1H-imidazo[4,5-b]pyrazin-2(3H)-one | 267.0 | [M + H]⁺ | 2.4 |
| (S)-6-ethyl-1-(1-phenylethyl)-1H-imidazo[4,5-b]pyrazin-2-ol | 269.1 | [M + H]⁺ | 17.4 |
| (S)-6-ethyl-1-(1-phenylethyl)-1H-imidazo[4,5-b]pyrazin-2(3H)-one | 269.1 | [M + H]⁺ | 17.4 |
| (S)-1-(1-phenylethyl)-6-propyl-1H-imidazo[4,5-b]pyrazin-2-ol | 283.1 | [M + H]⁺ | 29.7 |
| (S)-1-(1-phenylethyl)-6-propyl-1H-imidazo[4,5-b]pyrazin-2(3H)-one | 283.1 | [M + H]⁺ | 29.7 |
| (S)-6-methoxy-1-(1-phenylethyl)-1H-imidazo[4,5-b]pyrazin-2-ol | 271.1 | [M + H]⁺ | 8.8 |

-continued

| Name | m/z | Ion | SKM MF AC1.4 (μM) |
|---|---|---|---|
| (S)-6-methoxy-1-(1-phenylethyl)-1H-imidazo[4,5-b]pyrazin-2(3H)-one | 271.1 | [M + H]⁺ | 8.8 |
| 6-bromo-1-cyclohexyl-1H-imidazo[4,5-b]pyrazin-2-ol | 296.9; 298.9 | [M + H]⁺; [M + H]⁺ | 10.4 |
| 6-bromo-1-cyclohexyl-1H-imidazo[4,5-b]pyrazin-2(3H)-one | 296.9; 298.9 | [M + H]⁺; [M + H]⁺ | 10.4 |
| 1-cyclohexyl-6-(methylthio)-1H-imidazo[4,5-b]pyrazin-2-ol | 265.1 | [M + H]⁺ | 13.9 |
| 1-cyclohexyl-6-(methylthio)-1H-imidazo[4,5-b]pyrazin-2(3H)-one | 265.1 | [M + H]⁺ | 13.9 |
| (Z)-1-cyclohexyl-6-(prop-1-enyl)-1H-imidazo[4,5-b]pyrazin-2-ol | 259.1 | [M + H]⁺ | 6.0 |
| (Z)-1-cyclohexyl-6-(prop-1-enyl)-1H-imidazo[4,5-b]pyrazin-2(3H)-one | 259.1 | [M + H]⁺ | 6.0 |
| (E)-1-cyclohexyl-6-(prop-1-enyl)-1H-imidazo[4,5-b]pyrazin-2-ol | 259.1 | [M + H]⁺ | 6.1 |
| (E)-1-cyclohexyl-6-(prop-1-enyl)-1H-imidazo[4,5-b]pyrazin-2(3H)-one | 259.1 | [M + H]⁺ | 6.1 |
| (S,E)-1-(1-phenylethyl)-6-(prop-1-enyl)-1H-imidazo[4,5-b]pyrazin-2-ol | 281.1 | [M + H]⁺ | 1.6 |
| (S,E)-1-(1-phenylethyl)-6-(prop-1-enyl)-1H-imidazo[4,5-b]pyrazin-2(3H)-one | 281.1 | [M + H]⁺ | 1.6 |
| 6-bromo-1-isopropyl-1H-imidazo[4,5-b]pyrazin-2-ol | 259.0 | [M + H]⁺ | 6.0 |
| 6-bromo-1-isopropyl-1H-imidazo[4,5-b]pyrazin-2(3H)-one | 259.0 | [M + H]⁺ | 6.0 |
| 1-isopropyl-6-(methylthio)-1H-imidazo[4,5-b]pyrazin-2-ol | 225.1 | [M + H]⁺ | 6.7 |
| 1-isopropyl-6-(methylthio)-1H-imidazo[4,5-b]pyrazin-2(3H)-one | 225.1 | [M + H]⁺ | 6.7 |
| (Z)-1-isopropyl-6-(prop-1-enyl)-1H-imidazo[4,5-b]pyrazin-2-ol | 219.2 | [M + H]⁺ | 4.6 |
| (Z)-1-isopropyl-6-(prop-1-enyl)-1H-imidazo[4,5-b]pyrazin-2(3H)-one | 219.2 | [M + H]⁺ | 4.6 |
| (S)-6-ethoxy-1-(1-phenylethyl)-1H-imidazo[4,5-b]pyrazin-2-ol | 285.2 | [M + H]⁺ | 10.6 |
| (S)-6-ethoxy-1-(1-phenylethyl)-1H-imidazo[4,5-b]pyrazin-2(3H)-one | 285.2 | [M + H]⁺ | 10.6 |
| 6-bromo-1-(pentan-3-yl)-1H-imidazo[4,5-b]pyrazin-2-ol | 286.0; 288.0 | [M + 2H]²⁺; [M + 2H]²⁺ | 0.25 |
| 6-bromo-1-(pentan-3-yl)-1H-imidazo[4,5-b]pyrazin-2(3H)-one | 286.0; 288.0 | [M + 2H]²⁺; [M + 2H]²⁺ | 0.25 |
| 6-(methylthio)-1-(pentan-3-yl)-1H-imidazo[4,5-b]pyrazin-2-ol | 253.1 | [M + H]⁺ | 0.4 |
| 6-(methylthio)-1-(pentan-3-yl)-1H-imidazo[4,5-b]pyrazin-2(3H)-one | 253.1 | [M + H]⁺ | 0.4 |
| (E)-1-(pentan-3-yl)-6-(prop-1-enyl)-1H-imidazo[4,5-b]pyrazin-2-ol | 247.1 | [M + H]⁺ | 0.4 |
| (E)-1-(pentan-3-yl)-6-(prop-1-enyl)-1H-imidazo[4,5-b]pyrazin-2(3H)-one | 247.1 | [M + H]⁺ | 0.4 |
| (Z)-1-(pentan-3-yl)-6-(prop-1-enyl)-1H-imidazo[4,5-b]pyrazin-2-ol | 247.1 | [M + H]⁺ | 0.6 |
| (Z)-1-(pentan-3-yl)-6-(prop-1-enyl)-1H-imidazo[4,5-b]pyrazin-2(3H)-one | 247.1 | [M + H]⁺ | 0.6 |
| 6-methyl-1-(pentan-3-yl)-1H-imidazo[4,5-b]pyrazin-2-ol | 221.1 | [M + H]⁺ | 0.53 |
| 6-methyl-1-(pentan-3-yl)-1H-imidazo[4,5-b]pyrazin-2(3H)-one | 221.1 | [M + H]⁺ | 0.53 |
| (S,Z)-6-(hex-2-enyl)-1-(1-phenylethyl)-1H-imidazo[4,5-b]pyrazin-2-ol | | | 3.1 |
| 2-hydroxy-1-(pentan-3-yl)-1H-imidazo[4,5-b]pyrazine-6-carbonitrile | 232.1 | [M + H]⁺ | 36.4 |
| 2-oxo-3-(pentan-3-yl)-2,3-dihydro-1H-imidazo[4,5-b]pyrazine-5-carbonitrile | 232.1 | [M + H]⁺ | 36.4 |
| (R)-6-bromo-1-sec-butyl-1H-imidazo[4,5-b]pyrazin-2-ol | 273.0 | [M + H]⁺ | 1.5 |
| (R)-6-bromo-1-sec-butyl-1H-imidazo[4,5-b]pyrazin-2(3H)-one | 273.0 | [M + H]⁺ | 1.5 |
| (S)-6-bromo-1-sec-butyl-1H-imidazo[4,5-b]pyrazin-2-ol | 272.0 | [M + 2H]²⁺ | 0.8 |
| (S)-6-bromo-1-sec-butyl-1H-imidazo[4,5-b]pyrazin-2(3H)-one | 272.0 | [M + 2H]²⁺ | 0.8 |
| 6-bromo-1-tert-butyl-1H-imidazo[4,5-b]pyrazin-2-ol | 272.0 | [M + 2H]²⁺ | 0.8 |
| 6-bromo-1-tert-butyl-1H-imidazo[4,5-b]pyrazin-2(3H)-one | 272.0 | [M + 2H]²⁺ | 0.8 |
| 2-(6-bromo-2-hydroxy-1H-imidazo[4,5-b]pyrazin-1-yl)butanoic acid | 299.0 | [M − H]⁻ | >49 |

-continued

| Name | m/z | Ion | SKM MF AC1.4 (μM) |
|---|---|---|---|
| 2-(6-bromo-2-oxo-2,3-dihydro-1H-imidazo[4,5-b]pyrazin-1-yl)butanoic acid | 299.0 | [M − H]− | >49 |
| 2-(6-bromo-2-hydroxy-1H-imidazo[4,5-b]pyrazin-1-yl)-1-morpholinobutan-1-one | 370.0 | [M + H]+ | >49 |
| 6-bromo-1-(1-morpholino-1-oxobutan-2-yl)-1H-imidazo[4,5-b]pyrazin-2(3H)-one | 370.0 | [M + H]+ | >49 |
| (R)-6-bromo-1-(1-hydroxybutan-2-yl)-1H-imidazo[4,5-b]pyrazin-2-ol | 285.0 | [M − H]− | 1.1 |
| (R)-6-bromo-1-(1-hydroxybutan-2-yl)-1H-imidazo[4,5-b]pyrazin-2(3H)-one | 285.0 | [M − H]− | 1.1 |
| (S)-6-bromo-1-(1-hydroxybutan-2-yl)-1H-imidazo[4,5-b]pyrazin-2-ol | 285.0 | [M − H]− | 19.1 |
| (S)-6-bromo-1-(1-hydroxybutan-2-yl)-1H-imidazo[4,5-b]pyrazin-2(3H)-one | 285.0 | [M − H]− | 19.1 |
| 6-bromo-1-(1-methoxybutan-2-yl)-1H-imidazo[4,5-b]pyrazin-2-ol | 301.0 | [M + H]+ | 4.9 |
| 6-bromo-1-(1-methoxybutan-2-yl)-1H-imidazo[4,5-b]pyrazin-2(3H)-one | 301.0 | [M + H]+ | 4.9 |
| 1-(1-aminobutan-2-yl)-6-bromo-1H-imidazo[4,5-b]pyrazin-2-ol | 287.0 | [M + 2H]2+ | 1.1 |
| 1-(1-aminobutan-2-yl)-6-bromo-1H-imidazo[4,5-b]pyrazin-2(3H)-one | 287.0 | [M + 2H]2+ | 1.1 |
| 6-bromo-1-(1-(methylamino)butan-2-yl)-1H-imidazo[4,5-b]pyrazin-2-ol | 300.0 | [M + H]+ | 45.7 |
| 6-bromo-1-(1-(methylamino)butan-2-yl)-1H-imidazo[4,5-b]pyrazin-2(3H)-one | 300.0 | [M + H]+ | 45.7 |
| 6-bromo-1-(1-(dimethylamino)butan-2-yl)-1H-imidazo[4,5-b]pyrazin-2-ol | 315.0 | [M + 2H]2+ | 43.8 |
| 6-bromo-1-(1-(dimethylamino)butan-2-yl)-1H-imidazo[4,5-b]pyrazin-2(3H)-one | 315.0 | [M + 2H]2+ | 43.8 |
| 6-bromo-1-(1-(4-methylpiperazin-1-yl)butan-2-yl)-1H-imidazo[4,5-b]pyrazin-2-ol | 369.0 | [M + H]+ | 14.9 |
| 6-bromo-1-(1-(4-methylpiperazin-1-yl)butan-2-yl)-1H-imidazo[4,5-b]pyrazin-2(3H)-one | 369.0 | [M + H]+ | 14.9 |
| (R)-6-bromo-1-(1-morpholinobutan-2-yl)-1H-imidazo[4,5-b]pyrazin-2-ol | 356.0; 358.0 | [M + H]+; [M + H]+ | 0.3 |
| (R)-6-bromo-1-(1-morpholinobutan-2-yl)-1H-imidazo[4,5-b]pyrazin-2(3H)-one | 356.0; 358.0 | [M + H]+; [M + H]+ | 0.3 |
| (S)-6-bromo-1-(1-morpholinobutan-2-yl)-1H-imidazo[4,5-b]pyrazin-2-ol | 356.0; 358.0 | [M + H]+; [M + H]+ | >49 |
| (S)-6-bromo-1-(1-morpholinobutan-2-yl)-1H-imidazo[4,5-b]pyrazin-2(3H)-one | 356.0; 358.0 | [M + H]+; [M + H]+ | >49 |
| (E)-1-isopropyl-6-(prop-1-enyl)-1H-imidazo[4,5-b]pyrazin-2-ol | 219.1 | [M + H]+ | 7.1 |
| (E)-1-isopropyl-6-(prop-1-enyl)-1H-imidazo[4,5-b]pyrazin-2(3H)-one | 219.1 | [M + H]+ | 7.1 |
| 1-(pentan-3-yl)-1H-imidazo[4,5-b]pyrazin-2-ol | 207.1 | [M + H]+ | 16.0† |
| 1-(pentan-3-yl)-1H-imidazo[4,5-b]pyrazin-2(3H)-one | 207.1 | [M + H]+ | 16.0† |
| methyl 4-(2-(6-bromo-2-hydroxy-1H-imidazo[4,5-b]pyrazin-1-yl)butyl)piperazine-1-carboxylate | 414.0 | [M + 2H]2+ | 0.9† |
| methyl 4-(2-(6-bromo-2-oxo-2,3-dihydro-1H-imidazo[4,5-b]pyrazin-1-yl)butyl)piperazine-1-carboxylate | 414.0 | [M + 2H]2+ | 0.9† |
| 6-bromo-1-(1-(4-(methylsulfonyl)piperazin-1-yl)butan-2-yl)-1H-imidazo[4,5-b]pyrazin-2-ol | 434.0 | [M + 2H]2+ | 3.2† |
| 6-bromo-1-(1-(4-(methylsulfonyl)piperazin-1-yl)butan-2-yl)-1H-imidazo[4,5-b]pyrazin-2(3H)-one | 434.0 | [M + 2H]2+ | 3.2† |
| 5-bromo-1-(pentan-3-yl)-1H-imidazo[4,5-b]pyrazin-2-ol | 285.0; 287.0 | [M + H]+; [M + H]+ | 11.5 |
| 5-bromo-1-(pentan-3-yl)-1H-imidazo[4,5-b]pyrazin-2(3H)-one | 285.0; 287.0 | [M + H]+; [M + H]+ | 11.5 |
| 1-(pentan-3-yl)-1H-imidazo[4,5-b]quinoxalin-2-ol | 257.1 | [M + H]+ | 19.8 |
| 1-(pentan-3-yl)-1H-imidazo[4,5-b]quinoxalin-2(3H)-one | 257.1 | [M + H]+ | 19.8 |
| 6-ethynyl-1-(pentan-3-yl)-1H-imidazo[4,5-b]pyrazin-2-ol | 231.2 | [M + H]+ | 0.1‡ |
| 6-ethynyl-1-(pentan-3-yl)-1H-imidazo[4,5-b]pyrazin-2(3H)-one | 231.2 | [M + H]+ | 0.1‡ |
| 1-(pentan-3-yl)-6-(trifluoromethyl)-1H-imidazo[4,5-b]pyrazin-2-ol | 275.2 | [M + H]+ | 10.4‡ |
| 1-(pentan-3-yl)-6-(trifluoromethyl)-1H-imidazo[4,5-b]pyrazin-2(3H)-one | 275.2 | [M + H]+ | 10.4‡ |
| 6-bromo-1-(2-methyl-1-morpholinopropan-2-yl)-1H-imidazo[4,5-b]pyrazin-2-ol | 356.0; 358.0 | [M + H]+; [M + H]+ | 16.4‡ |
| 6-bromo-1-(2-methyl-1-morpholinopropan-2-yl)- | 356.0; | [M + H]+; | 16.4‡ |

-continued

| Name | m/z | Ion | SKM MF AC1.4 (μM) |
|---|---|---|---|
| 1H-imidazo[4,5-b]pyrazin-2(3H)-one | 358.0 | [M + H]+ | |
| (S)-6-bromo-1-(1-morpholinopropan-2-yl)-1H-imidazo[4,5-b]pyrazin-2-ol | 342.0; 344.0 | [M + H]+; [M + H]+ | >49 |
| (S)-6-bromo-1-(1-morpholinopropan-2-yl)-1H-imidazo[4,5-b]pyrazin-2(3H)-one | 342.0; 344.0 | [M + H]+; [M + H]+ | >49 |
| 6-methoxy-1-(pentan-3-yl)-1H-imidazo[4,5-b]pyrazin-2-ol | 237.1 | [M + H]+ | 2.2‡ |
| 6-methoxy-1-(pentan-3-yl)-1H-imidazo[4,5-b]pyrazin-2(3H)-one | 237.1 | [M + H]+ | 2.2‡ |
| (R)-6-bromo-1-(1-morpholinopropan-2-yl)-1H-imidazo[4,5-b]pyrazin-2-ol | 342.0; 344.0 | [M + H]+; [M + H]+ | 5.2‡ |
| (R)-6-bromo-1-(1-morpholinopropan-2-yl)-1H-imidazo[4,5-b]pyrazin-2(3H)-one | 342.0; 344.0 | [M + H]+; [M + H]+ | 5.2‡ |
| 1-(pentan-3-yl)-1H-imidazo[4,5-b]pyrazine-2,6-diol | 223.2 | [M + H]+ | >49 |
| 6-hydroxy-1-(pentan-3-yl)-1H-imidazo[4,5-b]pyrazin-2(3H)-one | 223.2 | [M + H]+ | >49 |
| 1-(pentan-3-yl)-6-(prop-1-ynyl)-1H-imidazo[4,5-b]pyrazin-2-ol | 245.2 | [M + H]+ | >49 |
| 1-(pentan-3-yl)-6-(prop-1-ynyl)-1H-imidazo[4,5-b]pyrazin-2(3H)-one | 245.2 | [M + H]+ | >49 |
| 1-(1-morpholinobutan-2-yl)-1H-imidazo[4,5-b]pyrazin-2-ol | 278.0 | [M + H]+ | >49 |
| 1-(1-morpholinobutan-2-yl)-1H-imidazo[4,5-b]pyrazin-2(3H)-one | 278.0 | | >49 |
| 1-(ethylpropyl)-6-(1-methylpyrazol-4-yl)imidazo[4,5-b]pyrazin-2-ol | 287.1 | [M + H]+ | 15 |
| 6-bromo-1-(propylbutyl)imidazo[4,5-b]pyrazin-2-ol | 313.1 | [M + H]+ | 0.7 |
| 1-[(1R)-3-methyl-1-(morpholin-4-ylmethyl)butyl]-6-bromoimidazo[4,5-b]pyrazin-2-ol | 384 | [M + H]+ | 0.5 |
| 1-(ethylpropyl)-6-vinylimidazo[4,5-b]pyrazin-2-ol | 233.1 | [M + H]+ | 2.3 |
| 1-(ethylpropyl)-6-(1-methylvinyl)imidazo[4,5-b]pyrazin-2-ol | 247 | [M + H]+ | 0.6 |
| 1-(ethylpropyl)-6-(methylethyl)imidazo[4,5-b]pyrazin-2-ol | 249 | [M + H]+ | 29.6 |
| 6-chloro-1-(ethylpropyl)imidazo[4,5-b]pyrazin-2-ol | 239.1 | [M + H]+ | 0.7 |
| 6-(dimethylamino)-1-(ethylpropyl)imidazo[4,5-b]pyrazin-2-ol | 250.1 | [M + H]+ | 2.2 |
| 1-((1R)-1-methyl-2-morpholin-4-ylethyl)-6-bromoimidazo[4,5-b]pyrazin-2-ol | 342, 344 | (M + H), (M + 2 + H) | 5.19 |
| 1-(ethylpropyl)-6-ethynylimidazo[4,5-b]pyrazin-2-ol | 229 | (M − H) | 0.15 |
| 1-(ethylpropyl)-6-methoxylmidazo[4,5-b]pyrazin-2-ol | 237 | (M − H) | 2.20 |
| 1-(1,1-dimethyl-2-morpholin-4-ylethyl)-6-bromoimidazo[4,5-b]pyrazin-2-ol | 356, 358 | (M + 1), (M + 2 + H) | 19.11 |
| 6-(1H-1,2,3-triazol-4-yl)-1-(ethylpropyl)imidazo[4,5-b]pyrazin-2-ol | 274 | (M + H)+ | 46.64 |
| 1-(ethylpropyl)-6-(trifluoromethyl)imidazo[4,5-b]pyrazin-2-ol | 275 | (M + H) | 10.37 |
| 1-[(1R)-1-(morpholin-4-ylmethyl)propyl]-6-ethynylimidazo[4,5-b]pyrazin-2-ol | 302 | (M + H) | 0.13 |
| 1-(ethylpropyl)-6-{2-[1-(ethylpropyl)-2-hydroxyimidazo[4,5-e]pyrazin-6-yl]ethynyl}imidazo[4,5-b]pyrazin-2-ol | 435 | (M + H) | 19.32 |
| 6-(dimethylamino)-1-(ethylpropyl)imidazo[4,5-b]pyrazin-2-ol | 250 | (M + H) | 2.79 |
| 6-ethyl-1-(ethylpropyl)imidazo[4,5-b]pyrazin-2-ol | 235 | [M + H] | 8.58 |

†Mean value.
‡Median value.

Using procedures similar to those described herein, the compounds in the following table were also synthesized and tested.

| Name |
|---|
| (S)-1-(2-hydroxy-1-(1-phenylethyl)-1H-imidazo[4,5-b]pyrazin-6-yl)ethanone |
| (S)-6-acetyl-1-(1-phenylethyl)-1H-imidazo[4,5-b]pyrazin-2(3H)-one |
| (S)-6-isobutyl-1-(1-phenylethyl)-1H-imidazo[4,5-b]pyrazin-2-ol |
| (S)-6-isobutyl-1-(1-phenylethyl)-1H-imidazo[4,5-b]pyrazin-2(3H)-one |
| (S)-6-hexyl-1-(1-phenylethyl)-1H-imidazo[4,5-b]pyrazin-2-ol |
| (S)-6-hexyl-1-(1-phenylethyl)-1H-imidazo[4,5-b]pyrazin-2(3H)-one |
| (S)-6-cyclohexyl-1-(1-phenylethyl)-1H-imidazo[4,5-b]pyrazin-2-ol |

| Name |
| --- |
| (S)-6-cyclohexyl-1-(1-phenylethyl)-1H-imidazo[4,5-b]pyrazin-2(3H)-one |
| (S)-1-(1-phenylethyl)-1H-imidazo[4,5-b]pyrazin-2-ol |
| (S)-1-(1-phenylethyl)-1H-imidazo[4,5-b]pyrazin-2(3H)-one |
| (S)-2-hydroxy-1-(1-phenylethyl)-1H-imidazo[4,5-b]pyrazine-6-carboxylic acid |
| (S)-2-oxo-3-(1-phenylethyl)-2,3-dihydro-1H-imidazo[4,5-b]pyrazine-5-carboxylic acid |
| (S)-methyl 2-hydroxy-1-(1-phenylethyl)-1H-imidazo[4,5-b]pyrazine-6-carboxylate |
| (S)-methyl 2-oxo-3-(1-phenylethyl)-2,3-dihydro-1H-imidazo[4,5-b]pyrazine-5-carboxylate |
| (S)-2-hydroxy-1-(1-phenylethyl)-1H-imidazo[4,5-b]pyrazine-6-carbonitrile |
| (S)-2-oxo-3-(1-phenylethyl)-2,3-dihydro-1H-imidazo[4,5-b]pyrazine-5-carbonitrile |
| (S)-2-hydroxy-1-(1-phenylethyl)-1H-imidazo[4,5-b]pyrazine-6-carboxamide |
| (S)-2-oxo-3-(1-phenylethyl)-2,3-dihydro-1H-imidazo[4,5-b]pyrazine-5-carboxamide |
| (S)-2-hydroxy-N-methyl-1-(1-phenylethyl)-1H-imidazo[4,5-b]pyrazine-6-carboxamide |
| (S)—N-methyl-2-oxo-3-(1-phenylethyl)-2,3-dihydro-1H-imidazo[4,5-b]pyrazine-5-carboxamide |
| (S)-2-hydroxy-N,N-dimethyl-1-(1-phenylethyl)-1H-imidazo[4,5-b]pyrazine-6-carboxamide |
| (S)—N,N-dimethyl-2-oxo-3-(1-phenylethyl)-2,3-dihydro-1H-imidazo[4,5-b]pyrazine-5-carboxamide |
| (S)—N,N-diethyl-2-hydroxy-1-(1-phenylethyl)-1H-imidazo[4,5-b]pyrazine-6-carboxamide |
| (S)—N,N-diethyl-2-oxo-3-(1-phenylethyl)-2,3-dihydro-1H-imidazo[4,5-b]pyrazine-5-carboxamide |
| (S)-(2-hydroxy-1-(1-phenylethyl)-1H-imidazo[4,5-b]pyrazin-6-yl)(morpholino)methanone |
| (S)-6-(morpholine-4-carbonyl)-1-(1-phenylethyl)-1H-imidazo[4,5-b]pyrazin-2(3H)-one |
| (S)-(2-hydroxy-1-(1-phenylethyl)-1H-imidazo[4,5-b]pyrazin-6-yl)(piperidin-1-yl)methanone |
| (S)-1-(1-phenylethyl)-6-(piperidine-1-carbonyl)-1H-imidazo[4,5-b]pyrazin-2(3H)-one |
| (S)-(2-hydroxy-1-(1-phenylethyl)-1H-imidazo[4,5-b]pyrazin-6-yl)(4-methylpiperazin-1-yl)methanone |
| (S)-6-(4-methylpiperazine-1-carbonyl)-1-(1-phenylethyl)-1H-imidazo[4,5-b]pyrazin-2(3H)-one |
| (S)—N-benzyl-2-hydroxy-1-(1-phenylethyl)-1H-imidazo[4,5-b]pyrazine-6-carboxamide |
| (S)—N-benzyl-2-oxo-3-(1-phenylethyl)-2,3-dihydro-1H-imidazo[4,5-b]pyrazine-5-carboxamide |
| (S)-6-((dimethylamino)methyl)-1-(1-phenylethyl)-1H-imidazo[4,5-b]pyrazin-2-ol |
| (S)-6-((dimethylamino)methyl)-1-(1-phenylethyl)-1H-imidazo[4,5-b]pyrazin-2(3H)-one |
| (S)-6-(morpholinomethyl)-1-(1-phenylethyl)-1H-imidazo[4,5-b]pyrazin-2-ol |
| (S)-6-(morpholinomethyl)-1-(1-phenylethyl)-1H-imidazo[4,5-b]pyrazin-2(3H)-one |
| (S)-1-(1-phenylethyl)-6-(piperidin-1-ylmethyl)-1H-imidazo[4,5-b]pyrazin-2-ol |
| (S)-1-(1-phenylethyl)-6-(piperidin-1-ylmethyl)-1H-imidazo[4,5-b]pyrazin-2(3H)-one |
| (S)-6-((4-methylpiperazin-1-yl)methyl)-1-(1-phenylethyl)-1H-imidazo[4,5-b]pyrazin-2-ol |
| (S)-6-((4-methylpiperazin-1-yl)methyl)-1-(1-phenylethyl)-1H-imidazo[4,5-b]pyrazin-2(3H)-one |
| (S)-6-(2-hydroxypropan-2-yl)-1-(1-phenylethyl)-1H-imidazo[4,5-b]pyrazin-2-ol |
| (S)-6-(2-hydroxypropan-2-yl)-1-(1-phenylethyl)-1H-imidazo[4,5-b]pyrazin-2(3H)-one |
| 6-(methylsulfinyl)-1-((S)-1-phenylethyl)-1H-imidazo[4,5-b]pyrazin-2-ol |
| 6-(methylsulfinyl)-1-((S)-1-phenylethyl)-1H-imidazo[4,5-b]pyrazin-2(3H)-one |
| (S)-6-(methylsulfonyl)-1-(1-phenylethyl)-1H-imidazo[4,5-b]pyrazin-2-ol |
| (S)-6-(methylsulfonyl)-1-(1-phenylethyl)-1H-imidazo[4,5-b]pyrazin-2(3H)-one |
| 6-cyclopropyl-1-(pentan-3-yl)-1H-imidazo[4,5-b]pyrazin-2-ol |
| 6-cyclopropyl-1-(pentan-3-yl)-1H-imidazo[4,5-b]pyrazin-2(3H)-one |
| 6-bromo-1-(tetrahydro-2H-pyran-4-yl)-1H-imidazo[4,5-b]pyrazin-2-ol |
| 6-bromo-1-(tetrahydro-2H-pyran-4-yl)-1H-imidazo[4,5-b]pyrazin-2(3H)-one |
| 1-cyclopropyl-6-(methylthio)-1H-imidazo[4,5-b]pyrazin-2-ol |
| 1-cyclopropyl-6-(methylthio)-1H-imidazo[4,5-b]pyrazin-2(3H)-one |
| 6-(methylthio)-1-(tetrahydro-2H-pyran-4-yl)-1H-imidazo[4,5-b]pyrazin-2-ol |
| 6-(methylthio)-1-(tetrahydro-2H-pyran-4-yl)-1H-imidazo[4,5-b]pyrazin-2(3H)-one |
| (E)-1-cyclopropyl-6-(prop-1-enyl)-1H-imidazo[4,5-b]pyrazin-2-ol |
| (E)-1-cyclopropyl-6-(prop-1-enyl)-1H-imidazo[4,5-b]pyrazin-2(3H)-one |
| (E)-6-(prop-1-enyl)-1-(tetrahydro-2H-pyran-4-yl)-1H-imidazo[4,5-b]pyrazin-2-ol |
| (E)-6-(prop-1-enyl)-1-(tetrahydro-2H-pyran-4-yl)-1H-imidazo[4,5-b]pyrazin-2(3H)-one |
| (Z)-1-cyclopropyl-6-(prop-1-enyl)-1H-imidazo[4,5-b]pyrazin-2-ol |
| (Z)-1-cyclopropyl-6-(prop-1-enyl)-1H-imidazo[4,5-b]pyrazin-2(3H)-one |
| (Z)-6-(prop-1-enyl)-1-(tetrahydro-2H-pyran-4-yl)-1H-imidazo[4,5-b]pyrazin-2-ol |
| (Z)-6-(prop-1-enyl)-1-(tetrahydro-2H-pyran-4-yl)-1H-imidazo[4,5-b]pyrazin-2(3H)-one |
| 6-bromo-1-cyclopropyl-1H-imidazo[4,5-b]pyrazin-2-ol |
| 6-bromo-1-cyclopropyl-1H-imidazo[4,5-b]pyrazin-2(3H)-one |
| 5-(methylthio)-1-(pentan-3-yl)-1H-imidazo[4,5-b]pyrazin-2-ol |
| 5-(methylthio)-1-(pentan-3-yl)-1H-imidazo[4,5-b]pyrazin-2(3H)-one |
| 5-ethyl-1-(pentan-3-yl)-1H-imidazo[4,5-b]pyrazin-2-ol |
| 5-ethyl-1-(pentan-3-yl)-1H-imidazo[4,5-b]pyrazin-2(3H)-one |
| 1-(pentan-3-yl)-5-vinyl-1H-imidazo[4,5-b]pyrazin-2-ol |
| 1-(pentan-3-yl)-5-vinyl-1H-imidazo[4,5-b]pyrazin-2(3H)-one |
| methyl 2-hydroxy-1-(pentan-3-yl)-1H-imidazo[4,5-b]pyrazine-5-carboxylate |
| methyl 2-oxo-1-(pentan-3-yl)-2,3-dihydro-1H-imidazo[4,5-b]pyrazine-5-carboxylate |
| 2-hydroxy-N,N-dimethyl-1-(pentan-3-yl)-1H-imidazo[4,5-b]pyrazine-5-carboxamide |
| N,N-dimethyl-2-oxo-1-(pentan-3-yl)-2,3-dihydro-1H-imidazo[4,5-b]pyrazine-5-carboxamide |
| 2-hydroxy-N-methyl-1-(pentan-3-yl)-1H-imidazo[4,5-b]pyrazine-5-carboxamide |
| N-methyl-2-oxo-1-(pentan-3-yl)-2,3-dihydro-1H-imidazo[4,5-b]pyrazine-5-carboxamide |

-continued

| Name |
|---|
| 1-(2-hydroxy-1-(pentan-3-yl)-1H-imidazo[4,5-b]pyrazin-5-yl)ethanone |
| 5-acetyl-1-(pentan-3-yl)-1H-imidazo[4,5-b]pyrazin-2(3H)-one |
| (S)-1-(1-phenylethyl)-1H-imidazo[4,5-b]quinoxalin-2-ol |
| (S)-1-(1-phenylethyl)-1H-imidazo[4,5-b]quinoxalin-2(3H)-one |
| 2-(6-bromo-2-hydroxy-1H-imidazo[4,5-b]pyrazin-1-yl)propane-1,3-diol |
| 6-bromo-1-(1,3-dihydroxypropan-2-yl)-1H-imidazo[4,5-b]pyrazin-2(3H)-one |
| 6-bromo-1-(2-morpholinoethyl)-1H-imidazo[4,5-b]pyrazin-2-ol |
| 6-bromo-1-(2-morpholinoethyl)-1H-imidazo[4,5-b]pyrazin-2(3H)-one |
| 2-hydroxy-1-(pentan-3-yl)-1H-imidazo[4,5-b]pyrazine-5-carboxylic acid |
| 2-oxo-1-(pentan-3-yl)-2,3-dihydro-1H-imidazo[4,5-b]pyrazine-5-carboxylic acid |

While some embodiments have been shown and described, various modifications and substitutions may be made thereto without departing from the spirit and scope of the invention. For example, for claim construction purposes, it is not intended that the claims set forth hereinafter be construed in any way narrower than the literal language thereof, and it is thus not intended that exemplary embodiments from the specification be read into the claims. Accordingly, it is to be understood that the present invention has been described by way of illustration and not limitations on the scope of the claims.

What is claimed is:

1. A method for treating amyotrophic lateral sclerosis in a patient, comprising administering to the patient an effective amount of at least one chemical entity chosen from compounds of Formula I and compounds of Formula II:

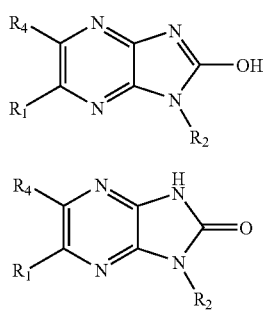

and pharmaceutically acceptable salts thereof, wherein
$R_1$ is selected from alkenyl and alkynyl;
$R_4$ is hydrogen; and
$R_2$ is selected from 3-pentyl, 4-heptyl, 4-methyl-1-morpholinopentan-2-yl isobutyl, cyclohexyl, cyclopropyl, sec-butyl, tert-butyl, isopropyl, 1-hydroxybutan-2-yl, tetrahydro-2H-pyran-4-yl, 1-methoxybutan-2-yl, 1-aminobutan-2-yl, and 1-morpholinobutan-2-yl;
provided that R1 is not hex-1-enyl.

2. The method of claim 1 wherein $R_1$ is selected from butenyl, propenyl, vinyl, and ethynyl.

3. The method of claim 2 wherein $R_1$ is selected from isobuten-1-yl, (Z)-propen-1-yl, (E)-propen-1-yl, propen-2-yl, vinyl, and ethynyl.

4. The method of claim 1 wherein $R_2$ is selected from 3-pentyl, 4-heptyl, 4-methyl-1-morpholinopentan-2-yl, isobutyl, sec-butyl, tert-butyl, isopropyl, 1-hydroxybutan-2-yl, tetrahydro-2H-pyran-4-yl, 1-methoxybutan-2-yl, 1-aminobutan-2-yl, and 1-morpholinobutan-2-yl.

5. The method of claim 1 wherein $R_2$ is selected from 3-pentyl, 4-heptyl, isobutyl, sec-butyl, tert-butyl, isopropyl, and 1-hydroxybutan-2-yl.

6. The method of claim 1 wherein $R_2$ is selected from 3-pentyl, 4-heptyl, isobutyl, sec-butyl, tert-butyl, and isopropyl.

7. The method of claim 6 wherein $R_1$ is ethynyl.

8. The method of claim 1, wherein the compound of Formula I is chosen from
1-[(1R)-1-(morpholin-4-ylmethyl)propyl]-6-ethynylimidazo[4,5-b]pyrazin-2-ol;
(E)-1-(pentan-3-yl)-6-(prop-1-enyl)-1H-imidazo[4,5-b]pyrazin-2-ol;
(E)-1-(pentan-3-yl)-6-(prop-1-enyl)-1H-imidazo[4,5-b]pyrazin-2-ol;
(E)-1-cyclohexyl-6-(prop-1-enyl)-1H-imidazo[4,5-b]pyrazin-2-ol;
(E)-1-cyclopropyl-6-(prop-1-enyl)-1H-imidazo[4,5-b]pyrazin-2-ol;
(E)-1-isopropyl-6-(prop-1-enyl)-1H-imidazo[4,5-b]pyrazin-2-ol;
(E)-6-(prop-1-enyl)-1-(tetrahydro-2H-pyran-4-yl)-1H-imidazo[4,5-b]pyrazin-2-ol;
(Z)-1-(pentan-3-yl)-6-(prop-1-enyl)-1H-imidazo[4,5-b]pyrazin-2-ol,
(Z)-1-cyclohexyl-6-(prop-1-enyl)-1H-imidazo[4,5-b]pyrazin-2-ol;
(Z)-1-cyclopropyl-6-(prop-1-enyl)-1H-imidazo[4,5-b]pyrazin-2-ol;
(Z)-1-isopropyl-6-(prop-1-enyl)-1H-imidazo[4,5-b]pyrazin-2-ol;
(Z)-6-(prop-1-enyl)-1-(tetrahydro-2H-pyran-4-yl)-1H-imidazo[4,5-b]pyrazin-2-ol;
1-(pentan-3-yl)-6-(prop-1-ynyl)-1H-imidazo[4,5-b]pyrazin-2-ol;
6-ethynyl-1-(pentan-3-yl)-1H-imidazo[4,5-b]pyrazin-2-ol;
1-(ethylpropyl)-6-vinylimidazo[4,5-b]pyrazin-2-ol; and
1-(ethylpropyl)-6-(1-methylvinyl)imidazo[4,5-b]pyrazin-2-ol;
and pharmaceutically acceptable salts thereof.

9. The method of claim 1, wherein the compound of Formula II is chosen from
6-ethynyl-1-(pentan-3-yl)-1H-imidazo[4,5-b]pyrazin-2(3H)-one;
(R)-6-ethynyl-1-(1-morpholinobutan-2-yl)-1H-imidazo[4,5-b]pyrazin-2(3H)-one;
(E)-1-(pentan-3-yl)-6-(prop-1-enyl)-1H-imidazo[4,5-b]pyrazin-2(3H)-one;
(E)-1-cyclohexyl-6-(prop-1-enyl)-1H-imidazo[4,5-b]pyrazin-2(3H)-one;
(E)-1-cyclopropyl-6-(prop-1-enyl)-1H-imidazo[4,5-b]pyrazin-2(3H)-one;

(E)-1-isopropyl-6-(prop-1-enyl)-1H-imidazo[4,5-b]pyrazin-2(3H)-one;
(E)-6-(prop-1-enyl)-1-(tetrahydro-2H-pyran-4-yl)-1H-imidazo[4,5-b]pyrazin-2(3H)-one;
(Z)-1-(pentan-3-yl)-6-(prop-1-enyl)-1H-imidazo[4,5-b]pyrazin-2(3H)-one;
(Z)-1-cyclohexyl-6-(prop-1-enyl)-1H-imidazo[4,5-b]pyrazin-2(3H)-one;
(Z)-1-cyclopropyl-6-(prop-1-enyl)-1H-imidazo[4,5-b]pyrazin-2(3H)-one;
(Z)-1-isopropyl-6-(prop-1-enyl)-1H-imidazo[4,5-b]pyrazin-2(3H)-one;
(Z)-6-(prop-1-enyl)-1-(tetrahydro-2H-pyran-4-yl)-1H-imidazo[4,5-b]pyrazin-2(3H)-one;
1-(pentan-3-yl)-6-(prop-1-ynyl)-1H-imidazo[4,5-b]pyrazin-2(3H)-one;
1-(pentan-3-yl)-6-vinyl-1H-imidazo[4,5-b]pyrazin-2(3H)-one; and
1-(pentan-3-yl)-6-(prop-1-en-2-yl)-1H-imidazo[4,5-b]pyrazin-2(3H)-one;
and pharmaceutically acceptable salts thereof.

10. A method for treating amyotrophic lateral sclerosis in a patient, comprising administering to the patient an effective amount of a pharmaceutical composition comprising a pharmaceutically acceptable carrier and at least one chemical entity chosen from compounds of Formula I and compounds of Formula II:

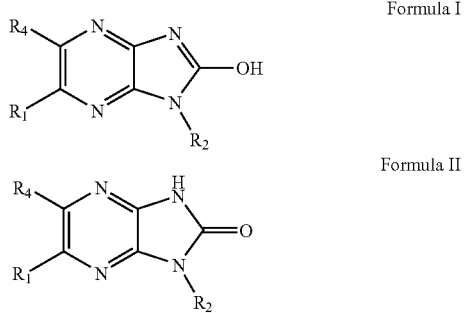

Formula I

Formula II and pharmaceutically acceptable salts thereof, wherein
$R_1$ is selected from alkenyl and alkynyl;
$R_4$ is hydrogen; and
$R_2$ is selected from 3-pentyl, 4-heptyl, 4-methyl-1-morpholinopentan-2-yl isobutyl, cyclohexyl, cyclopropyl, sec-butyl, tert-butyl, isopropyl, 1-hydroxybutan-2-yl, tetrahydro-2H-pyran-4-yl, 1-methoxybutan-2-yl, 1-aminobutan-2-yl, and 1-morpholinobutan-2-yl;
provided that R1 is not hex-1-enyl.

11. The method of claim 10, wherein the pharmaceutical composition is formulated in a form chosen from tablets, capsules, powders, liquids, suspensions, suppositories and aerosols.

12. The method of claim 10, wherein the pharmaceutical composition is formulated in a form chosen from tablets, capsules, powders and suspensions.

13. The method of claim 10 wherein $R_1$ is selected from butenyl, propenyl, vinyl, and ethynyl.

14. The method of claim 13 wherein $R_1$ is selected from isobuten-1-yl, (Z)- propen-1-yl, (E)-propen-1-yl, propen-2-yl, vinyl, and ethynyl.

15. The method of claim 10 wherein $R_2$ is selected from 3-pentyl, 4-heptyl, 4-methyl-1-morpholinopentan-2-yl, isobutyl, sec-butyl, tert-butyl, isopropyl, 1-hydroxybutan-2-yl, tetrahydro-2H-pyran-4-yl, 1-methoxybutan-2-yl, 1-aminobutan-2-yl, and 1-morpholinobutan-2-yl.

16. The method of claim 10 wherein $R_2$ is selected from 3-pentyl, 4-heptyl, isobutyl, sec-butyl, tert-butyl, isopropyl, and 1-hydroxybutan-2-yl.

17. The method of claim 10 wherein $R_2$ is selected from 3-pentyl, 4-heptyl, isobutyl, sec-butyl, tert-butyl, and isopropyl.

18. The method of claim 17 wherein $R_1$ is ethynyl.

19. The method of claim 10, wherein the compound of Formula I is chosen from
1-[(1R)-1-(morpholin-4-ylmethyl)propyl]-6-ethynylimidazo[4,5-b]pyrazin-2-ol;
(E)-1-(pentan-3-yl)-6-(prop-1-enyl)-1H-imidazo[4,5-b]pyrazin-2-ol;
(E)-1-(pentan-3-yl)-6-(prop-1-enyl)-1H-imidazo[4,5-b]pyrazin-2-ol;
(E)-1-cyclohexyl-6-(prop-1-enyl)-1H-imidazo[4,5-b]pyrazin-2-ol;
(E)-1-cyclopropyl-6-(prop-1-enyl)-1H-imidazo[4,5-b]pyrazin-2-ol;
(E)-1-isopropyl-6-(prop-1-enyl)-1H-imidazo[4,5-b]pyrazin-2-ol,
(E)-6-(prop-1-enyl)-1-(tetrahydro-2H-pyran-4-yl)-1H-imidazo[4,5-b]pyrazin-2-ol;
(Z)-1-(pentan-3-yl)-6-(prop-1-enyl)-1H-imidazo[4,5-b]pyrazin-2-ol;
(Z)-1-cyclohexyl-6-(prop-1-enyl)-1H-imidazo[4,5-b]pyrazin-2-ol;
(Z)-1-cyclopropyl-6-(prop-1-enyl)-1H-imidazo[4,5-b]pyrazin-2-ol;
(Z)-1-isopropyl-6-(prop-1-enyl)-1H-imidazo[4,5-b]pyrazin-2-ol;
(Z)-6-(prop-1-enyl)-1-(tetrahydro-2H-pyran-4-yl)-1H-imidazo[4,5-b]pyrazin-2-ol;
1-(pentan-3-yl)-6-(prop-1-ynyl)-1H-imidazo[4,5-b]pyrazin-2-ol;
6-ethynyl-1-(pentan-3-yl)-1H-imidazo[4,5-b]pyrazin-2-ol;
1-(ethylpropyl)-6-vinylimidazo[4,5-b]pyrazin-2-ol; and
1-(ethylpropyl)-6-(1-methylvinyl)imidazo[4,5-b]pyrazin-2-ol;
and pharmaceutically acceptable salts thereof.

20. The method of claim 10, wherein the compound of Formula II is chosen from
6-ethynyl-1-(pentan-3-yl)-1H-imidazo[4,5-b]pyrazin-2(3H)-one;
(R)-6-ethynyl-1-(1-morpholinobutan-2-yl)-1H-imidazo[4,5-b]pyrazin-2(3H)-one;
(E)-1-(pentan-3-yl)-6-(prop-1-enyl)-1H-imidazo[4,5-b]pyrazin-2(3H)-one;
(E)-1-cyclohexyl-6-(prop-1-enyl)-1H-imidazo[4,5-b]pyrazin-2(3H)-one;
(E)-1-cyclopropyl-6-(prop-1-enyl)-1H-imidazo[4,5-b]pyrazin-2(3H)-one;
(E)-1-isopropyl-6-(prop-1-enyl)-1H-imidazo[4,5-b]pyrazin-2(3H)-one;
(E)-6-(prop-1-enyl)-1-(tetrahydro-2H-pyran-4-yl)-1H-imidazo[4,5-b]pyrazin-2(3H)-one;
(Z)-1-(pentan-3-yl)-6-(prop-1-enyl)-1H-imidazo[4,5-b]pyrazin-2(3H)-one;
(Z)-1-cyclohexyl-6-(prop-1-enyl)-1H-imidazo[4,5-b]pyrazin-2(3H)-one;
(Z)-1-cyclopropyl-6-(prop-1-enyl)-1H-imidazo[4,5-b]pyrazin-2(3H)-one;
(Z)-1-isopropyl-6-(prop-1-enyl)-1H-imidazo[4,5-b]pyrazin-2(3H)-one;

(Z)-6-(prop-1-enyl)-1-(tetrahydro-2H-pyran-4-yl)-1H-imidazo[4,5-b]pyrazin-2(3H)-one;
1-(pentan-3-yl)-6-(prop-1-ynyl)-1H-imidazo[4,5-b]pyrazin-2(3H)-one;
1-(pentan-3-yl)-6-vinyl-1H-imidazo[4,5-b]pyrazin-2(3H)-one; and
1-(pentan-3-yl)-6-(prop-1-en-2-yl)-1H-imidazo[4,5-b]pyrazin-2(3H)-one;
and pharmaceutically acceptable salts thereof.

* * * * *